United States Patent
Wang et al.

(10) Patent No.: US 11,008,304 B2
(45) Date of Patent: *May 18, 2021

(54) TETRAZOLE CONTAINING APOPTOSIS SIGNAL-REGULATING KINASE 1 INHIBITORS AND METHODS OF USE THEREOF

(71) Applicant: ENANTA PHARMACEUTICALS, INC., Watertown, MA (US)

(72) Inventors: Guoqiang Wang, Belmont, MA (US); Ruichao Shen, Belmont, MA (US); Brett Granger, Sudbury, MA (US); Jing He, Somerville, MA (US); Xuechao Xing, Wilmington, MA (US); Yong He, Lexington, MA (US); Jiang Long, Wayland, MA (US); Jun Ma, Belmont, MA (US); Bin Wang, Brighton, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/400,529

(22) Filed: May 1, 2019

(65) Prior Publication Data
US 2019/0337923 A1    Nov. 7, 2019

Related U.S. Application Data

(60) Provisional application No. 62/665,789, filed on May 2, 2018.

(51) Int. Cl.
| | | |
|---|---|---|
| *C07D 401/14* | (2006.01) | |
| *C07D 413/14* | (2006.01) | |
| *C07D 405/14* | (2006.01) | |
| *C07D 409/14* | (2006.01) | |
| *C07D 417/14* | (2006.01) | |

(52) U.S. Cl.
CPC ......... *C07D 401/14* (2013.01); *C07D 405/14* (2013.01); *C07D 409/14* (2013.01); *C07D 413/14* (2013.01); *C07D 417/14* (2013.01)

(58) Field of Classification Search
CPC .................................................. C07D 401/14
USPC ........................................................ 546/256
See application file for complete search history.

(56) References Cited

U.S. PATENT DOCUMENTS

| | | | | |
|---|---|---|---|---|
| 6,140,347 A * | 10/2000 | Castro Pineiro | ..... | C07D 231/12 514/323 |
| 6,534,651 B2 | 3/2003 | Jagtap et al. | | |
| 7,678,792 B2 | 3/2010 | Chianelli et al. | | |
| 8,378,108 B2 * | 2/2013 | Corkey | .............. | A61K 31/4439 546/256 |
| 8,653,075 B2 | 2/2014 | Grundl et al. | | |
| 8,895,745 B2 * | 11/2014 | Berdini | .................... | A61P 11/02 546/121 |
| 9,067,933 B2 * | 6/2015 | Corkey | ................ | C07D 401/12 |
| 9,132,140 B2 * | 9/2015 | Reddy | .................... | A61K 45/06 |
| 9,254,284 B2 | 2/2016 | Notte | | |
| 9,751,885 B2 | 9/2017 | Tomita et al. | | |
| 10,246,439 B2 | 4/2019 | Granger et al. | | |
| 10,253,018 B2 | 4/2019 | Wang et al. | | |
| 10,450,301 B2 | 10/2019 | Granger et al. | | |
| 10,597,382 B2 | 3/2020 | Wang et al. | | |

(Continued)

FOREIGN PATENT DOCUMENTS

| | | |
|---|---|---|
| CN | 107793400 A | 3/2018 |
| WO | 2004018428 A1 | 3/2004 |

(Continued)

OTHER PUBLICATIONS

Silverman, "The Organic Chemistry of Drug Design and Drug Action," 2004, Elsevier, pp. 29-32.*

(Continued)

*Primary Examiner* — Nizal S Chandrakumar
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts and esters thereof:

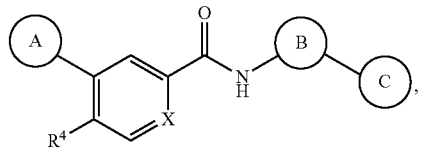

which inhibit the Apoptosis signal-regulating kinase 1 (ASK-1), which is associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcoholic steatohepatitis (NASH).

6 Claims, No Drawings

(56) References Cited

U.S. PATENT DOCUMENTS

| | | | |
|---|---|---|---|
| 10,683,279 | B2 | 6/2020 | Wang et al. |
| 10,683,289 | B2 | 6/2020 | Granger et al. |
| 2005/0113450 | A1 | 5/2005 | Thorarensen et al. |
| 2009/0318425 | A1 | 12/2009 | Chang et al. |
| 2010/0029619 | A1 | 2/2010 | Uchikawa et al. |
| 2011/0009410 | A1 | 1/2011 | Corkey et al. |
| 2012/0004267 | A1 | 1/2012 | Corkey et al. |
| 2013/0203731 | A1 | 8/2013 | Chang et al. |
| 2013/0210810 | A1 | 8/2013 | Singh et al. |
| 2014/0018370 | A1 | 1/2014 | Corkey et al. |
| 2014/0249135 | A1 | 9/2014 | Burger et al. |
| 2014/0329850 | A1 | 11/2014 | Chang |
| 2015/0005280 | A1 | 1/2015 | Sasmal et al. |
| 2017/0210748 | A1 | 7/2017 | Witty et al. |
| 2018/0327388 | A1 | 11/2018 | Wang et al. |
| 2018/0362501 | A1 | 12/2018 | Wang et al. |
| 2018/0362502 | A1 | 12/2018 | Granger et al. |
| 2018/0362503 | A1 | 12/2018 | Granger et al. |
| 2019/0062310 | A1 | 2/2019 | Wang et al. |
| 2019/0337935 | A1 | 11/2019 | Granger et al. |
| 2020/0062727 | A1 | 2/2020 | He et al. |
| 2020/0157095 | A1 | 5/2020 | Granger et al. |
| 2020/0308193 | A1 | 10/2020 | Granger et al. |
| 2020/0331890 | A1 | 10/2020 | Wang et al. |

FOREIGN PATENT DOCUMENTS

| | | | |
|---|---|---|---|
| WO | 2005009470 | A1 | 2/2005 |
| WO | 2005103288 | A1 | 11/2005 |
| WO | 2007000339 | A1 | 1/2007 |
| WO | 2008082579 | A1 | 7/2008 |
| WO | 2009011850 | A2 | 1/2009 |
| WO | 2009027283 | A1 | 3/2009 |
| WO | 2009123986 | A1 | 10/2009 |
| WO | 2010008843 | A1 | 1/2010 |
| WO | 2011008709 | A1 | 1/2011 |
| WO | 2011041293 | A1 | 4/2011 |
| WO | 2011097079 | A1 | 8/2011 |
| WO | 2012003387 | A1 | 1/2012 |
| WO | 2012011548 | A1 | 1/2012 |
| WO | 2012080735 | A1 | 6/2012 |
| WO | 2013112741 | A1 | 8/2013 |
| WO | 2014100541 | A1 | 6/2014 |
| WO | 2014106019 | A2 | 7/2014 |
| WO | 2014137728 | A1 | 9/2014 |
| WO | 2015095059 | A1 | 6/2015 |
| WO | 2015187499 | A1 | 12/2015 |
| WO | 2016049069 | A1 | 3/2016 |
| WO | 2016049070 | A1 | 3/2016 |
| WO | 2016105453 | A1 | 6/2016 |
| WO | 2016106384 | A1 | 6/2016 |
| WO | 2018090869 | A1 | 5/2018 |
| WO | 2018133856 | A1 | 7/2018 |
| WO | 2018133865 | A1 | 7/2018 |
| WO | 2018133866 | A1 | 7/2018 |
| WO | 2018148204 | A1 | 8/2018 |
| WO | 2018149284 | A1 | 8/2018 |
| WO | 2018151830 | A1 | 8/2018 |
| WO | 2018157277 | A1 | 9/2018 |
| WO | 2018157856 | A1 | 9/2018 |
| WO | 2018157857 | A1 | 9/2018 |
| WO | 2018160406 | A1 | 9/2018 |
| WO | 2018169742 | A1 | 9/2018 |
| WO | 2018183122 | A1 | 10/2018 |
| WO | 2018187506 | A1 | 10/2018 |
| WO | 2018218051 | A1 | 11/2018 |
| WO | 2018233553 | A1 | 12/2018 |
| WO | 2019034096 | A1 | 2/2019 |
| WO | 2019050794 | A1 | 3/2019 |
| WO | 2019051265 | A1 | 3/2019 |
| WO | 2019070742 | A1 | 4/2019 |

OTHER PUBLICATIONS

Dudkin,Chemistry of Heterocyclic Compounds, vol. 48, No. 1, Apr. 2012.*
Burger, J. Am. Chem. Soc. 1938, 60, 11, 2628-2630.*
Loomba, Hepatology, vol. 67, No. 2, 2018.*
Lanier, ACS Med. Chem. Lett. 2017, 8, 316-320.*
Pubmed Compound Summary for CID 53276841, '2-Methyl-1,1,3-trioxo-N-pyridin-2-yl-1,2-benzolhiazole-6-carboxamide', U.S. National library of Medicine, Aug. 1, 2011 (Aug. 1, 2011), p. 1-7; p. 2 (https:/lpubchem.ncbi.nlm.nih.gov/compound/53276841).
Gibson, et al., "Structure-based drug design of novel ASK1 inhibitors using an integrated lead optimization strategy", Bioorganic & Medicinal Chemistry Letters, 2017, 1-5.
Lanier, Marion et al., "Structure-Based Design of ASK1 Inhibitors as Potential Agents for Heart Failure", ACS Medicinal Chemistry Letters 2017, vol. 8, 2017, 316-320.
Loomba, et al., "The ASK1 Inhibitor Selonsertib in Patients with Nonalcoholic Steatohepatitis: A Randomized, Phase 2 Trial", Hepatology 67(2), 2018, 549-559.
Lovering, et al., "Rational approach to highly potent and selective apoptosis signal regulating kinase 1 (ASK1) inhibitors", European Journal of Medicinal Chemistry, 145, 2018, 606-621.
Monastyrsky, et al., "Discovery of 2-arylquinazoline derivatives as a new class of ASK1 inhibitors", Bioorganic & Medicinal Chemistry Letters, 28, 2018, 400-404.
Patani, George A. et al., "Bioisosterism: A Rational Approach in Drug Design", Chem. Rev. 1996, 96, 1996, 3147-3176.
Sheridan, Robert P., "The Most Common Chemical Replacements in Drug-Like Compounds", J. Chem. Info. Comput. Sci. 2002, vol. 42, 2002, 103-108.
Terao et al., "Design and biological evaluation of imidazo[1,2-a]pyridines as novel and potent ASK1 inhibitors", Bioorganic & Medicinal Chemistry Letters, 22, 2012, 7326-7329.
Volynets, et al., "Identification of 3H-Naphtho[1,2,3-de]quinoline-2,7-diones as Inhibitors of Apoptosis Signal-Regulating Kinase 1 (ASK1)", Journal of Medicinal Chemistry, 54, 2011, 2680-2686.
Volynets, et al., "Rational design of apoptosis signal-regulating kinase 1 inhibitors: Discovering novel structural scaffold", European Journal of Medicinal Chemistry 61, 2013, 104-115.
Wermuth, C. G., "Molecular Variations Based on Isosteric Replacements", in "The Practice of Medicinal Chemistry", Academic Press Limited, 1996, 203-237.
Kawarazaki, et al., "Apoptosis signal-regulating kinase 1 as a therapeutic target", Expert Opinion on Therapeutic Targets, 18(6), 2014, 651-664.
Starosyla, S. et al., "ASK1 Pharmacophore Model Derived from Diverse Classes of Inhibitors", Bioorganic & Medicinal Chemistry Letters, 24, 2014, 4418-4423.
Okamoto, M., "Identification of novel ASK1 inhibitors using virtual screening", Bioorganic & Medicinal Chemistry, vol. 19, 2011, 486-489.
Starosyla, S. et al., "Identification of apoptosis signal-regulating kinase 1 (ASK1) inhibitors among the derivatives of benzothiazol-2-yl-3-hydroxy-5-phenyl-1,5-dihydro-pyrrol-2-one", Bioorganic & Medicinal Chemistry, vol. 23., 2015, 2489-2497.

* cited by examiner

TETRAZOLE CONTAINING APOPTOSIS SIGNAL-REGULATING KINASE 1 INHIBITORS AND METHODS OF USE THEREOF

RELATED APPLICATIONS

This application claims the benefit of U.S. Provisional Application No. 62/665,789, filed on May 2, 2018. The entire teachings of the above application are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (NK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcoholic steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med. Chem.* 2011, 54, 2680-2686, WO 2012/003387, WO 2012/011548, WO 2012/080735, Y. Terao, et al., *Bioorg. Med. Chem. Lett.* 2012, 22, 7326-7329, WO 2013/112741, G. P. Volynets, et al., *Eur. J. Med. Chem.* 2013, 16, 104-115, US 2014/0018370, WO 2014/100541, WO 2015/095059, WO 2016/049069, WO 2016/049070, WO 2018/090869, WO 2018/133865, WO 2018/133866, WO 2018/148204, WO 2018/149284, WO 2018/151830, WO/2018/157856, WO 2018/157857, WO 2018/160406, WO 2018/169742, WO 2018/183122, WO 2018/187506, WO 2018/209354, WO 2018/218042, WO 2018/218044, WO 2018/218051, WO 2018/233553, US 2019/0062310, WO 2019/070742, WO 2019/050794, WO 2019/051265, and WO 2019/034096.

There is a need for the development of ASK-1 inhibitors for the treatment and prevention of disease.

SUMMARY OF THE INVENTION

The present invention relates to compounds and pharmaceutical compositions useful as ASK-1 inhibitors. Specifically, the present invention relates to compounds useful as inhibitors of ASK-1 and methods for their preparation and use. In addition, the present invention includes the process for the preparation of the said compounds.

In its principal aspect, the present invention provides a compound of Formula (I), or a pharmaceutically acceptable salt or ester thereof:

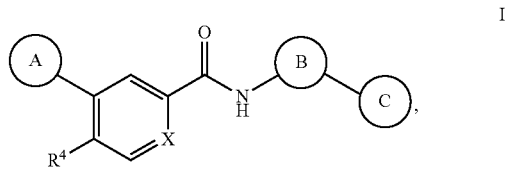

wherein

is optionally substituted aryl or optionally substituted heteroaryl containing 1, 2 or 3 heteroatoms selected from N, O and S, provided that

is not

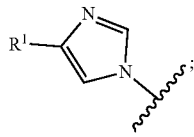

In certain embodiments,

Ⓐ is selected from:

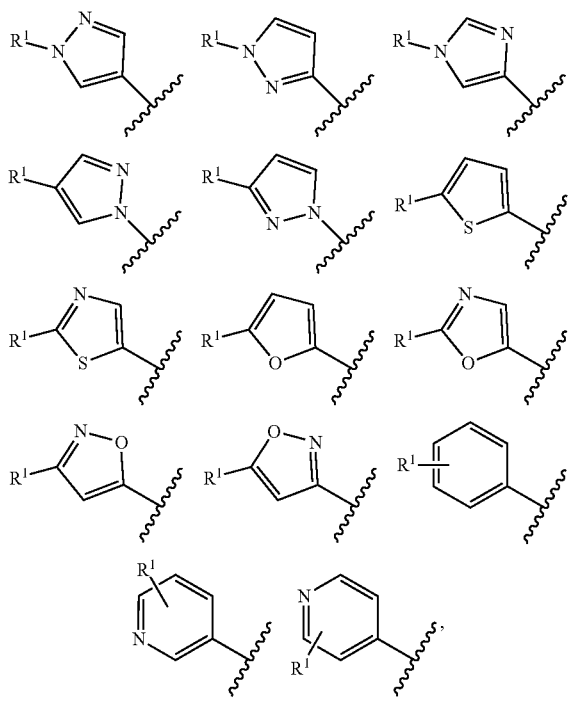

Ⓑ is

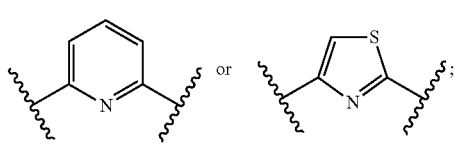 [SMILES: *c1cccc(*)n1 ; *c1csc(*)n1]

Ⓒ is

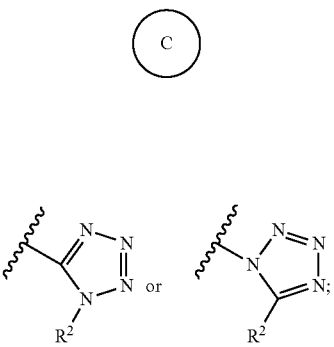

$R^1$ and $R^2$ are each independently selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted aryl;
7) Optionally substituted arylalkyl;
8) Optionally substituted 3- to 8-membered heterocycloalkyl;
9) Optionally substituted heteroaryl; and
10) Optionally substituted heteroarylalkyl;
X is N or C—$R^3$;
$R^3$ is selected from the group consisting of:
1) Hydrogen;
2) Halogen;
3) Optionally substituted —$C_1$-$C_8$ alkyl; and
4) Optionally substituted —$C_1$-$C_8$ alkoxyl;
$R^4$ is selected from the group consisting of:
1) Hydrogen;
2) Halogen;
3) Optionally substituted —$C_1$-$C_8$ alkyl;
4) Optionally substituted —$C_2$-$C_8$ alkenyl;
5) Optionally substituted —$C_2$-$C_8$ alkynyl;
6) Optionally substituted —$C_3$-$C_8$ cycloalkyl;
7) Optionally substituted aryl;
8) Optionally substituted arylalkyl;
9) Optionally substituted 3- to 8-membered heterocycloalkyl;
10) Optionally substituted heteroaryl;
11) Optionally substituted heteroarylalkyl; and
12) —$N(R^5)(R^6)$;
wherein $R^5$ and $R^6$ are independently selected from the group consisting of hydrogen, —$C_1$-$C_8$ alkyl, cycloalkyl, heterocycloalkyl, aryl, and heteroaryl, all of which are optionally substituted with 1-3 substituents selected from halo, alkyl, mono- or dialkylamino, alkyl or aryl or heteroaryl amide, —CN, alkoxy, —$CF_3$, aryl, and heteroaryl. Alternatively, $R^5$ and $R^6$ are taken together with the nitrogen atom to which they are attached to form an optionally substituted heterocyclic.

In another embodiment, the present invention provides a pharmaceutical composition comprising a therapeutically effective amount of a compound or combination of compounds of the present invention, or a pharmaceutically acceptable salt, ester or combination thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I). The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula (I) as described above, or a pharmaceutically acceptable salt or ester thereof.

In certain embodiments of the compounds of Formula (I), X is CH.

In certain embodiments of the compounds of Formula (I), X is CF.

In certain embodiments of the compounds of Formula (I), X is N.

In certain embodiments of the compounds of Formula (I), $R^1$ is selected from the groups below,

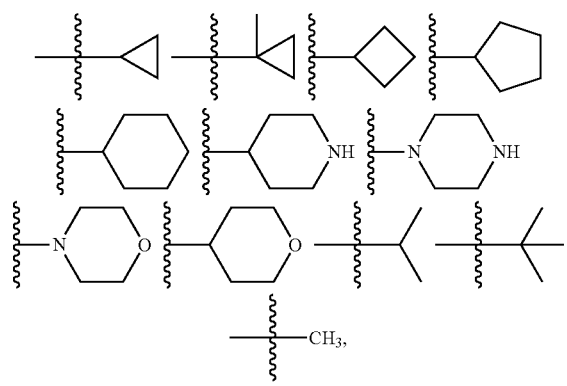

where each of these groups is optionally further substituted.

In certain embodiments, of the compounds of Formula (I), $R^4$ is selected from the groups shown below:

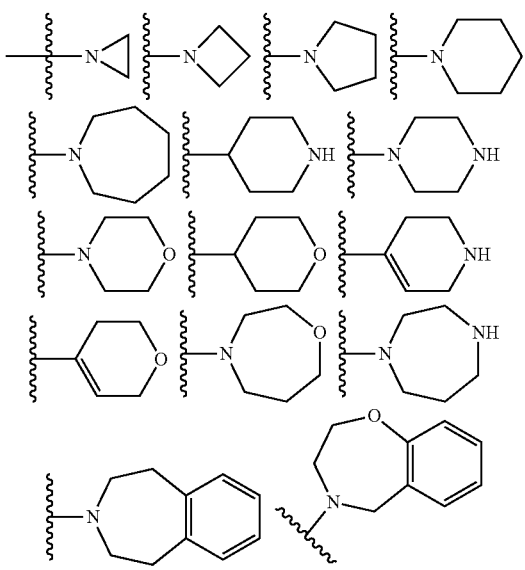

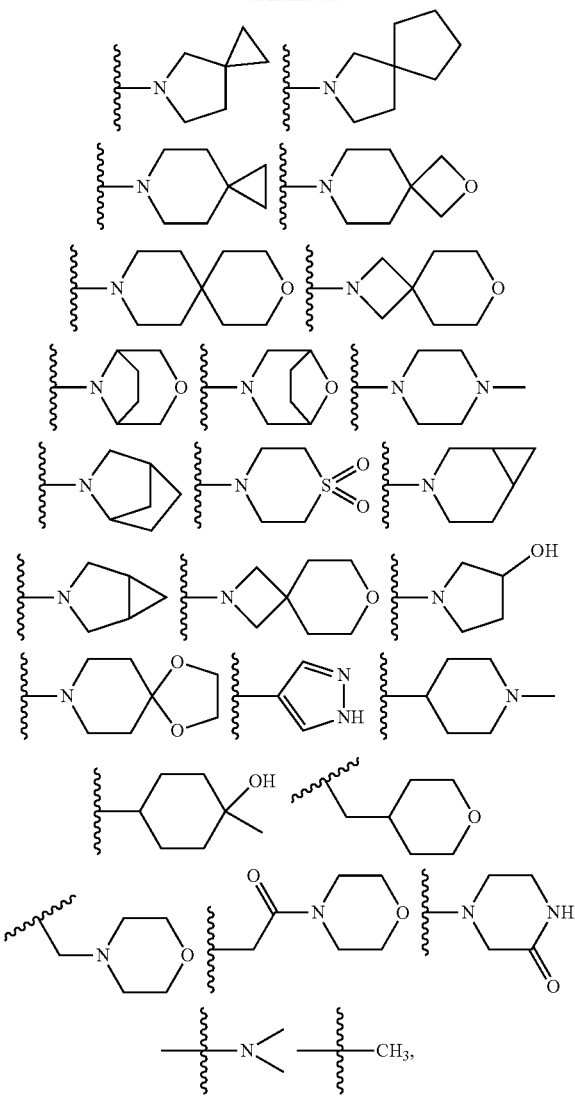

where each of these groups is optionally further substituted.

In certain embodiments of the compounds of Formula (I), $R^2$ is selected from the groups set forth below:

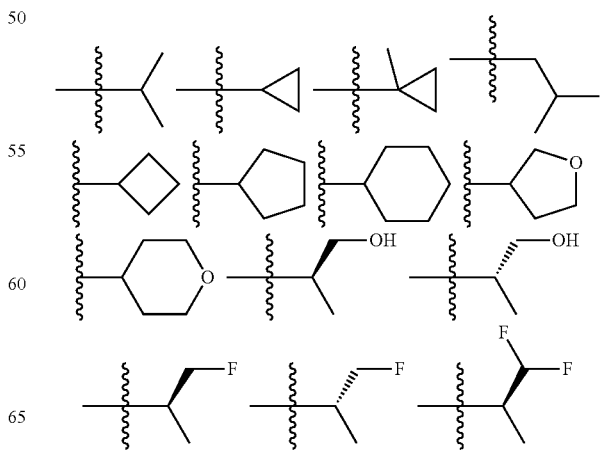

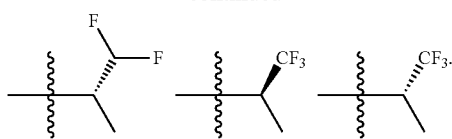

In certain embodiments, the invention provides compounds represented by Formula (II-a~II-h) and pharmaceutically acceptable salts and esters thereof:

II-a
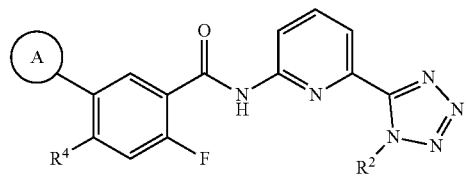

II-b
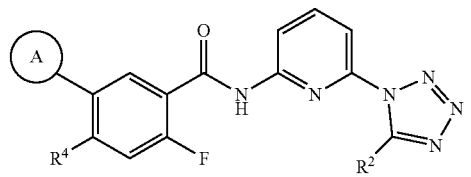

II-c
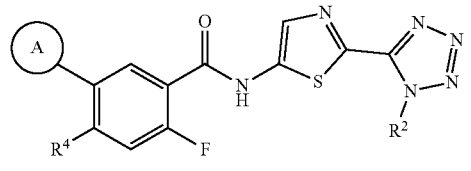

II-d
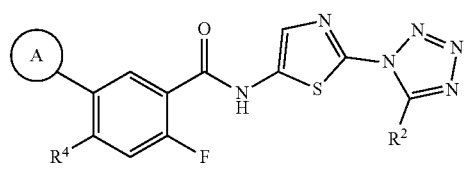

II-e
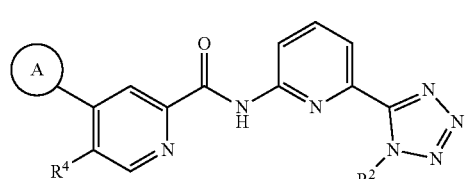

II-f
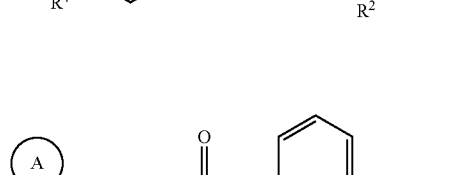

II-g
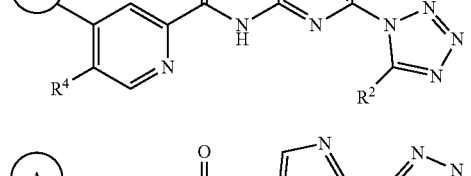

II-h
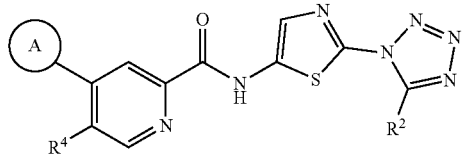

wherein

, $R^2$ and $R^4$ are as previously defined.

In certain embodiments, the invention provides compounds represented by Formula (III-a~III-n) and pharmaceutically acceptable salts and esters thereof, III-a
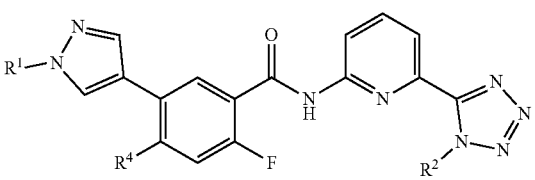

III-b
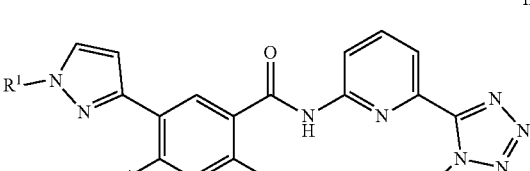

III-c
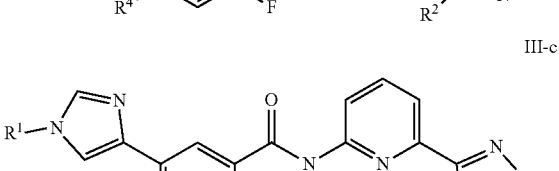

III-d
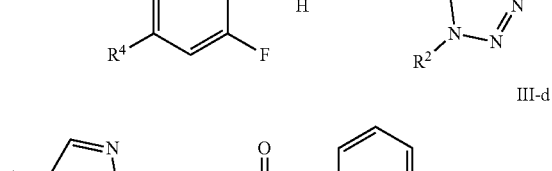

III-e
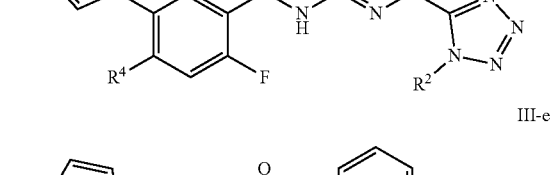

III-f
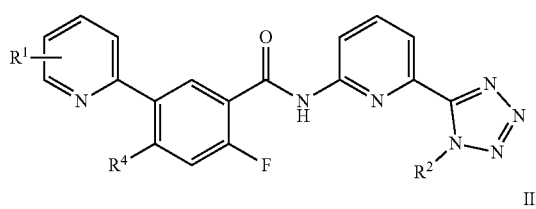
III-g
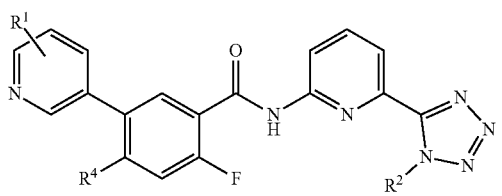
III-h
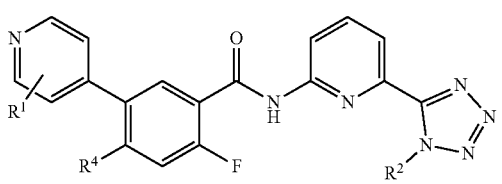
III-i
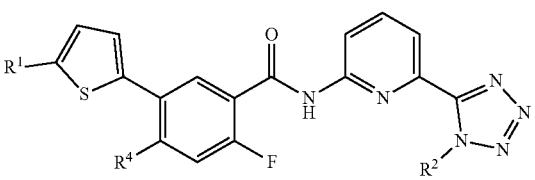
III-j
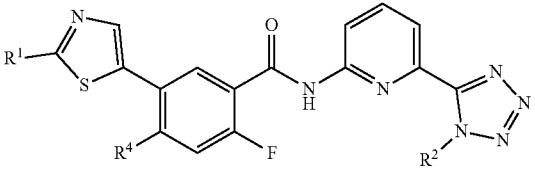
III-k
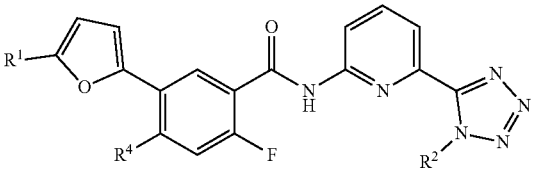
III-l
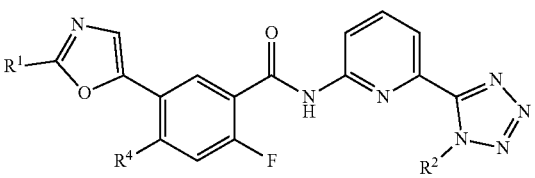
III-m
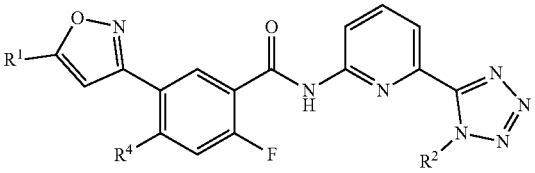
III-n
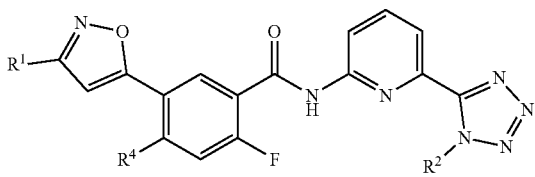
wherein R¹, R² and R⁴ are as previously defined.
In certain embodiments, the invention provides compounds represented by Formula (IV-a~IV-n) and pharmaceutically acceptable salts and esters thereof,
IV-a
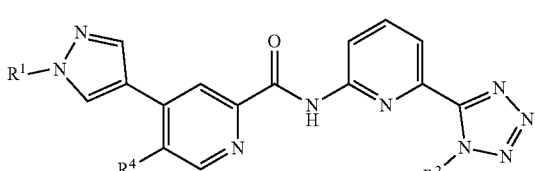
IV-b
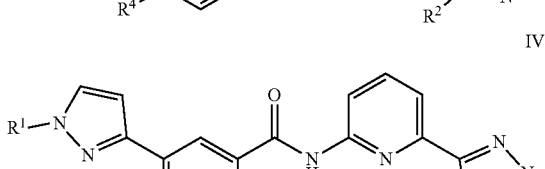
IV-c
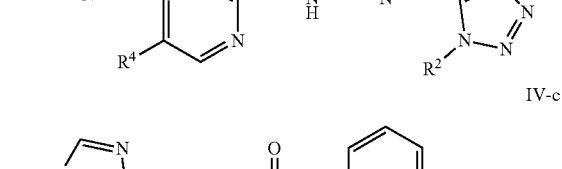
IV-d
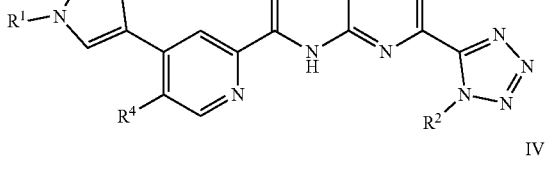
IV-e
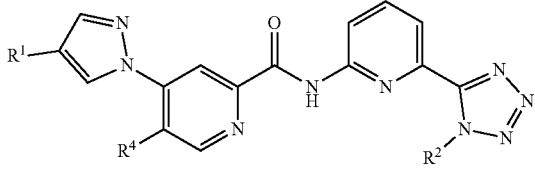
IV-f
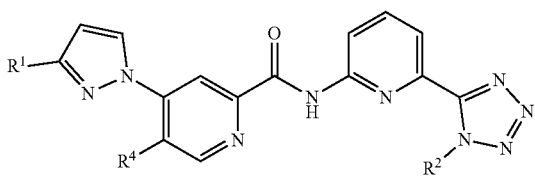
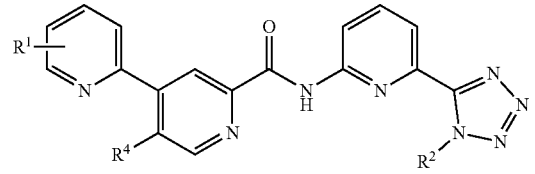

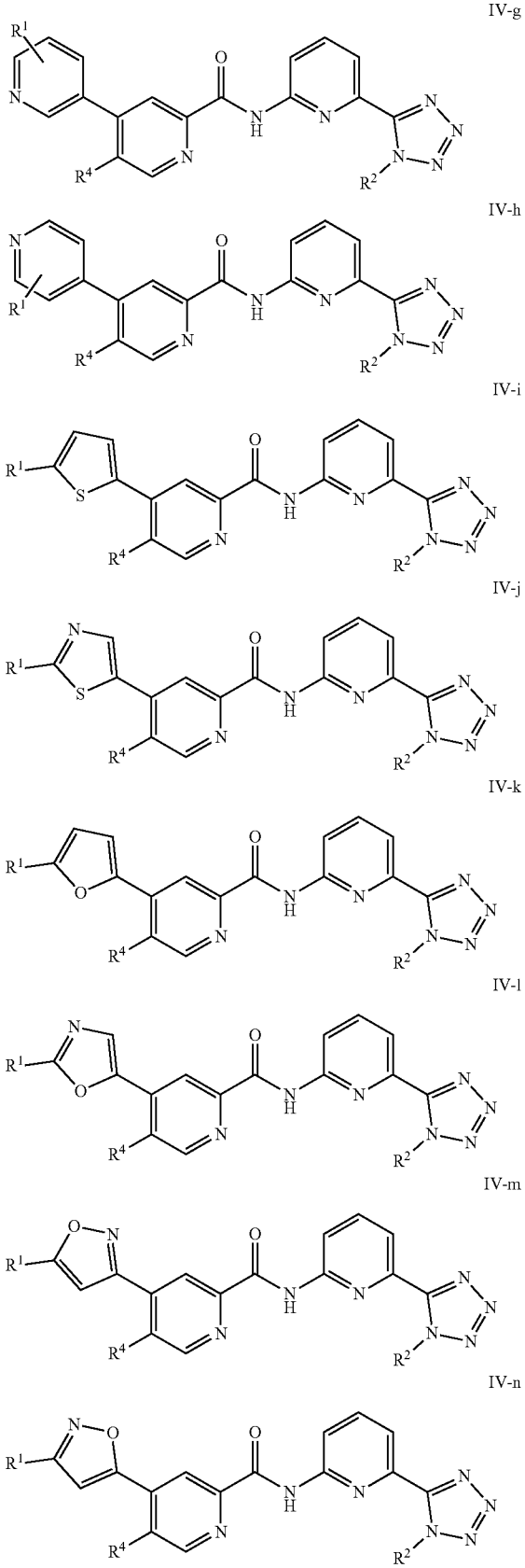

wherein R¹, R² and R⁴ are previously defined.

In certain embodiments, the present invention provides a method for the prevention or treatment of an ASK-1 mediated disease or condition. The method comprises administering a therapeutically effective amount of a compound of Formula (I), or a pharmaceutically acceptable salt thereof, to a subject in need thereof. The present invention also provides the use of a compound of Formula (I), or a pharmaceutically acceptable salt thereof, in the manufacture of a medicament for the treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. Suitable alkyl groups include "$C_1$-$C_3$ alkyl", "$C_1$-$C_6$ alkyl", "$C_1$-$C_{10}$ alkyl", "$C_2$-$C_4$ alkyl", or "$C_3$-$C_6$ alkyl", which refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. Suitable alkenyl groups include "$C_2$-$C_{10}$ alkenyl", "$C_2$-$C_8$ alkenyl", "$C_2$-$C_4$ alkenyl", or "$C_3$-$C_6$ alkenyl", which refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. Suitable alkynyl groups include "$C_2$-$C_{10}$ alkynyl," "$C_2$-$C_8$ alkynyl," "$C_2$-$C_4$ alkynyl," or "$C_3$-$C_6$ alkynyl," which refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like. The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but are not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —$NO_2$, —CN, —$NH_2$, $N_3$, protected amino, alkoxy, thioalkoxy, oxo, $C_1$-$C_{12}$-alkyl, $C_2$-$C_{12}$-alkenyl, $C_2$-$C_{12}$-alkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH— heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH— aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$— aryl, —$NHCO_2$— heteroaryl, —$NHCO_2$—heterocycloalkyl, —NHC(O)$NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH— $C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—

$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$— aryl, —$SO_2NH$— heteroaryl, —$SO_2NH$— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, -S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —$NO_2$, —CN, or —$NH_2$. Preferably, a substituted alkyl group, such as a substituted methyl group, is substituted with one or more halogen atoms, more preferably one or more fluorine or chlorine atoms.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above and includes optionally substituted aryl groups as also defined above. The term "arylthio" refers to the group R—S—, where R is as defined for aryl.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein can contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and 2007, pp 31-99.

The term "amino" as used herein, refers to the group —NH$_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the Techniques of Chemistry Series, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods ofPurification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Or anic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator.

The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional nontoxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
BOP-Cl for bis(2-oxo-3-oxazolidinyl)phosphinic chloride;
CDI for carbonyldiimidazole;
DBU for 1,8-diazabicycloundec-7-ene;
DCC for N,N-dicyclohexylcarbodiimide;
DCM for dichloromethane;
DIPEA for N,N-diisopropylethylamine;
DMAP for N,N-dimethylaminopyridine;
DME for 1,2-dimethoxyethane;
DMF for N,N-dimethyl formamide;
DMPU for 1,3-Dimethyl-3,4,5,6-tetrahydro-2(1H)-pyrimidinone;
EDC for 1-(3-diethylaminopropyl)-3-ethylcarbodiimide hydrochloride;
$Et_3N$ for triethylamine;
EtOAc for ethyl acetate;

HATU for 1-[bis(dimethylamino)methylene]-1H-1,2,3-triazolo[4,5-b]pyridinium 3-oxid hexafluorophosphate;
HCl for hydrochloric acid;
mCPBA for meta-chloroperoxybenzoic acid;
NMO for N-methylmorpholine-N-oxide;
PE for petroleum ether
PhMe for toluene;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, the ester compound of formula (S-4), wherein $R^4$, X, and have been previously defined, can be prepared under Suzuki-Miyaura coupling conditions either from compound of formula (S-1) and corresponding boronic esters or acids; or from compound of formula (S-2) with corresponding halides. Alternatively, compound of formula (S-3), which can be prepared by Suzuki-Miyaura coupling conditions, can be converted to ester compound of formula (S-4) by Pd-catalyzed CO insertion in alcohols. Hydrolysis of compound of formula (S-4) under basic conditions provides carboxylic acid compound of formula (S-5).

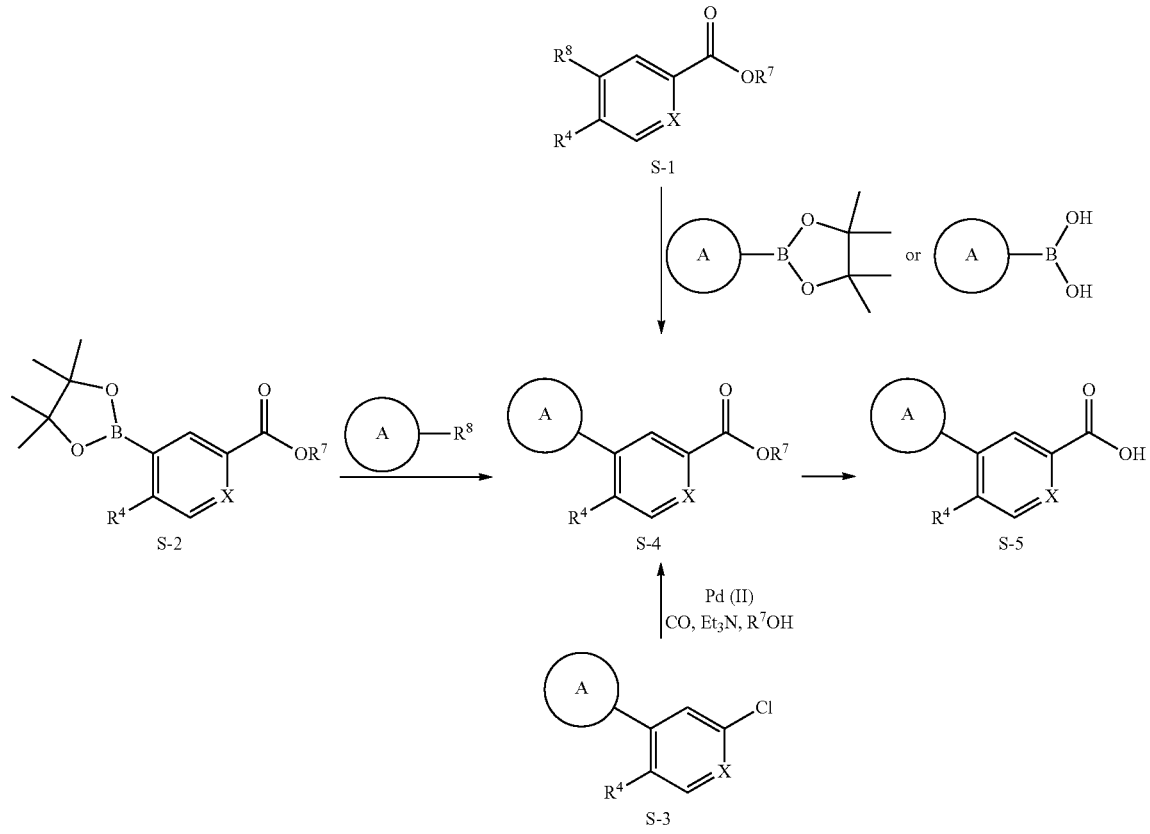

As shown in Scheme 2, treatment of carboxylic acid compound of formula (S-5) and amine compound of formula (S-6) in an aprotic solvent with a suitable coupling reagent in the presence of organic base forms amide compound of Formula (I), wherein

R⁴, X,

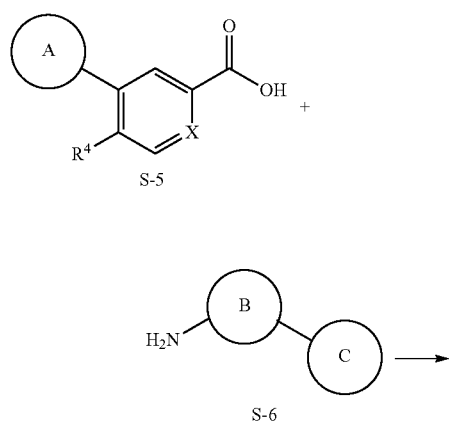

have been previously defined. The suitable coupling reagent can be, such as, but not limited to, BOP-Cl, CDI, DCC, EDC, HATU, PyAOP or PyBOP. The organic base can be, such as, but not limited to, Et₃N, DIPEA, pyridine or N-methyl morpholine. The aprotic solvent can be, such as, but not limited to, THF, DCM and DMF. The reaction temperature is from −20° C. to 80° C.

Scheme 2

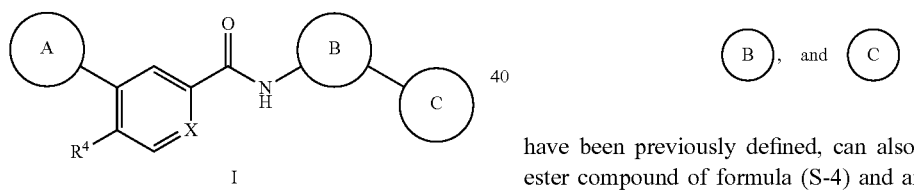

As shown in Scheme 3, the carboxylic acid compound of formula (S-5) can be first converted to acyl chloride compound of formula (S-7), using such as, but not limited to, oxalyl chloride or Ghosez reagent. Treatment of the acyl chloride (S-7) with amine compound of formula (S-6) in the presence of organic base, such as pyridine, provides compound of formula (I), wherein (A),

R⁴, X, (B), and (C)

have been previously defined.

Scheme 3.

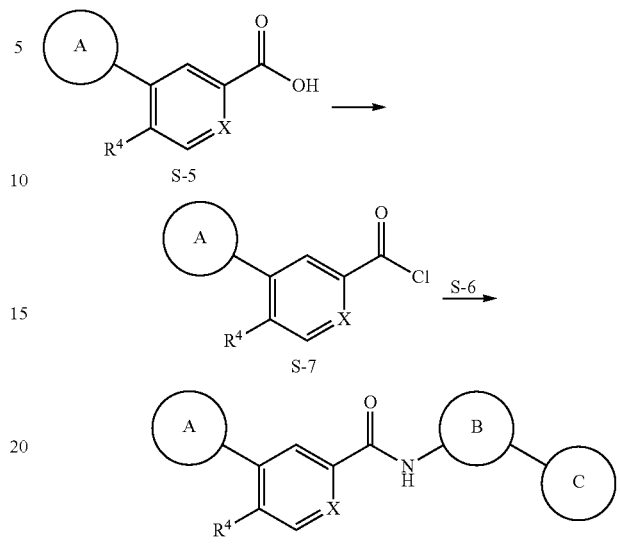

As shown in Scheme 4, amide compound of formula (I), wherein (A),

R⁴, X, (B), and (C)

have been previously defined, can also be prepared from ester compound of formula (S-4) and amine compound of formula (S-6) under ester-amide exchange conditions. These conditions include, but not limited to, Cs₂CO₃ or K₂CO₃ in DMF at elevated temperature; or AlMe₃ in DCM at ambient or elevated temperature.

Scheme 4

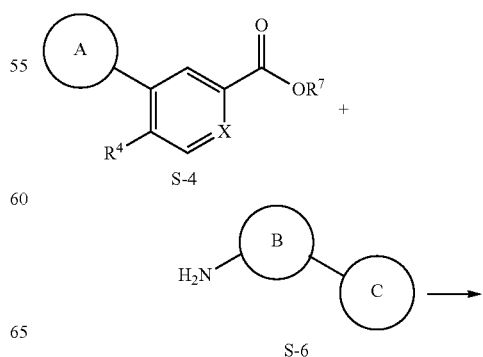

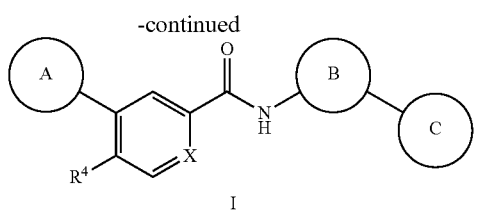

I

EXAMPLES

Example 1

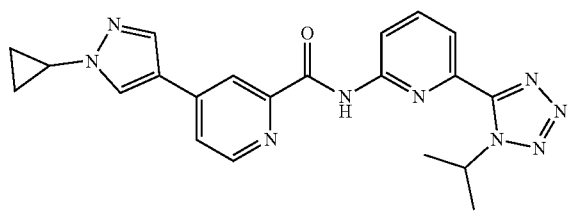 [SMILES: CC(C)n1nnnc1-c1cccc(NC(=O)c2cc(-c3cnn(C4CC4)c3)ccn2)n1]

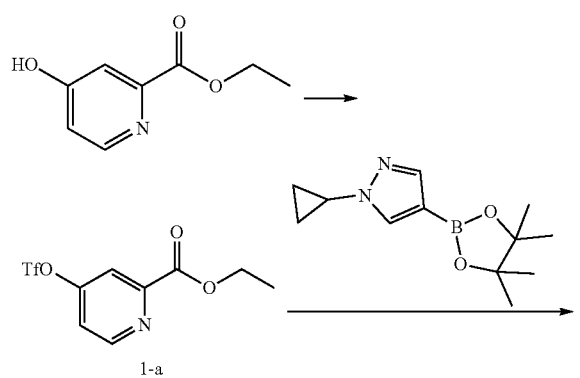

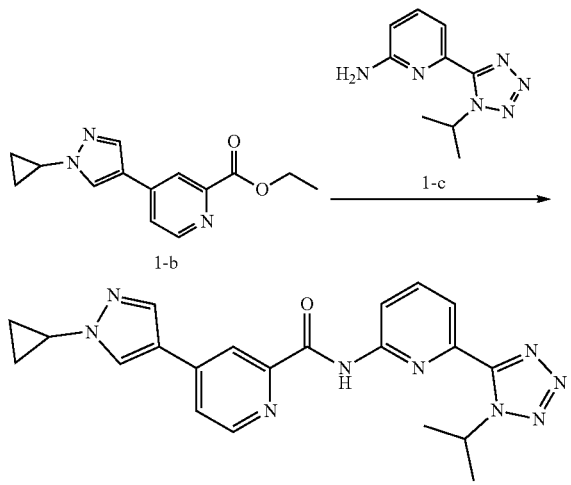

Example 1

Step 1-1

To a solution of ethyl 4-hydroxypyridine-2-carboxylate (200 mg, 1.20 mmol) in DCM (5 mL) at 0° C. was added triethylamine (242.1 mg, 2.39 mmol) and Tf₂O (506.3 mg, 1.79 mmol) dropwise. The mixture was warmed to room temperature and stirred for 1 hour, and concentrated in vacuo. Purification of the residue by silica gel column chromatography with 0-20% EtOAc in PE afforded compound 1-a (170 mg, 47.49%) as a yellow oil.

Step 1-2

A mixture of compound 1-a (150 mg, 0.50 mmol), 1-cyclopropyl-4-(tetramethyl-1,3,2-dioxaborolan-2-yl)-1H-pyrazole (234.7 mg, 1.00 mmol), Pd(PPh₃)₄ (57.9 mg, 0.05 mmol) and K₂CO₃ (138.6 mg, 1.00 mmol) in dioxane (5 mL) was stirred at 100° C. under nitrogen atmosphere for 1 h. Solvent was removed under vacuum. Purification of the residue by silica gel chromatography with EtOAc in PE (0-50%) afforded compound 1-b (60 mg, 46.52%) as yellow oil.

Step 1-3

A mixture of compound 1-b (60 mg, 0.23 mmol), compound 1-c (71.4 mg, 0.35 mmol) and Cs₂CO₃ (152.0 mg, 0.47 mmol) in DMF was stirred at 120° C. for 2 h. Solvent was removed under vacuum. Purification of the residue by C-18 column with CH₃CN in H₂O (60-70%) afforded Example 1 (7.8 mg) as a white solid. [M+H]⁺, 416. ¹H NMR (400 MHz, Chloroform-d) δ 10.61 (s, 1H), 8.65-8.61 (m, 2H), 8.40 (s, 1H), 8.12 (d, J=7.6 Hz, 1H), 8.04-8.01 (m, 3H), 7.62 (dd, J=5.3, 1.6 Hz, 1H), 5.89 (m, 1H), 3.72 (m, 1H), 1.76 (d, J=6.6 Hz, 6H), 1.23 (m, 2H), 1.14 (m, 2H).

Example 2

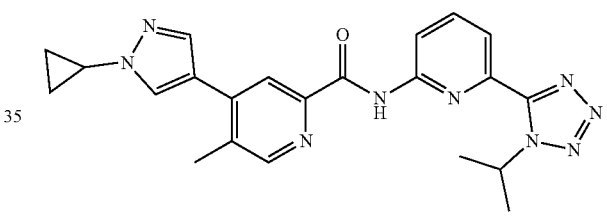

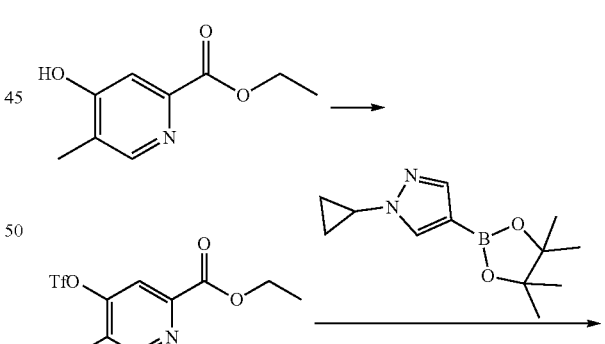

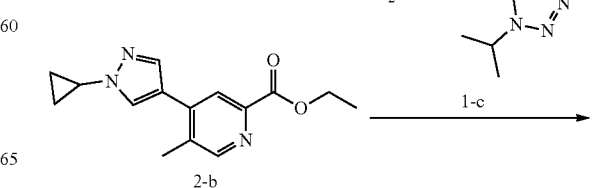

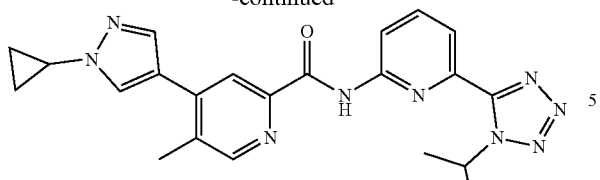

Example 2

Step 2-1

At 0° C. Tf₂O (1.86 g, 6.60 mmol) was added dropwise to a solution of ethyl 4-hydroxy-5-methylpyridine-2-carboxylate (800 mg, 4.42 mmol) and Et₃N (1.33 g, 13.20 mmol) in DCM (5 mL). The resulting mixture was stirred at room temperature for 1 h and concentrated under vacuum. Purification of the residue by silica gel column chromatography with EtOAc in PE (0-24%) afforded compound 2-a (550 mg, 39.8%) as a yellow oil.

Step 2-2

A mixture of compound 2-a (550 mg, 1.76 mmol), 1-cyclopropyl-4-(tetramethyl-1,3,2-dioxaborolan-2-yl)-1H-pyrazole (822.1 mg, 3.51 mmol), Pd(PPh₃)₄ (202.9 mg, 0.18 mmol) and K₂CO₃ (485.3 mg, 3.51 mmol) in dioxane (10 mL) was stirred at 100° C. for 2 h under nitrogen atmosphere. Solvent was removed under vacuum. The residue was purified by silica gel column chromatography with EtOAc in PE (0-35%) to afford compound 2-b (400 mg, 83.97%) as a yellow oil.

Step 2-3

A mixture of compound 2-b (80 mg, 0.29 mmol), compound 1-c (90.3 mg, 0.44 mmol) and Cs₂CO₃ (192.1 mg, 0.59 mmol) in DMF (2 mL) was stirred at 100° C. for 1 h. Solvent was removed under vacuum. The crude product was purified by C18 column with CH₃CN in H₂O (50-70%) to afford Example 2 (15.3 mg) as a white solid. [M+H]⁺, 430; ¹H NMR (400 MHz, Chloroform-d) δ 10.54 (s, 1H), 8.61 (d, J=8.3 Hz, 1H), 8.52 (s, 1H), 8.31 (s, 1H), 8.09 (d, J=8.3 Hz, 1H), 8.00 (t, J=8.0 Hz, 1H), 7.87 (s, 2H), 5.88 (m, 1H), 3.72 (m, 1H), 2.57 (s, 3H), 1.75 (d, J=6.7 Hz, 6H), 1.24 (m, 2H), 1.16 (m, 2H).

Example 3

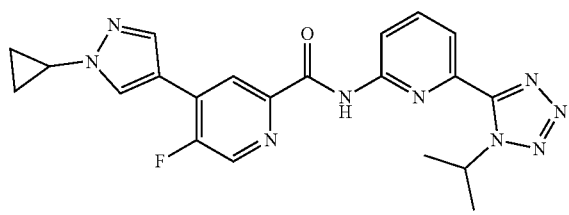 [SMILES: CC(C)n1nnnc1-c1cccc(NC(=O)c2cc(-c3cnn(C4CC4)c3)c(F)cn2)n1]

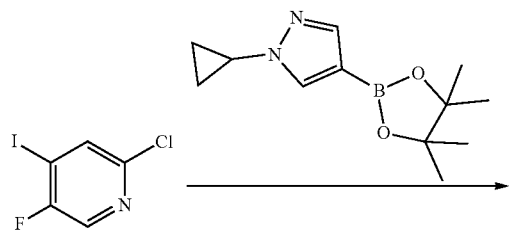

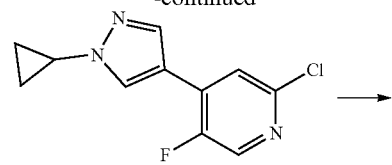

3-a

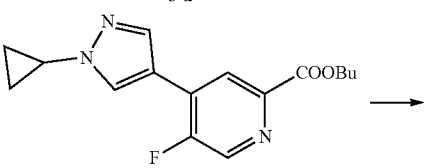

3-b

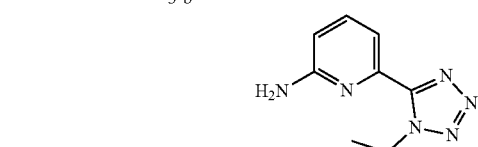

3-c

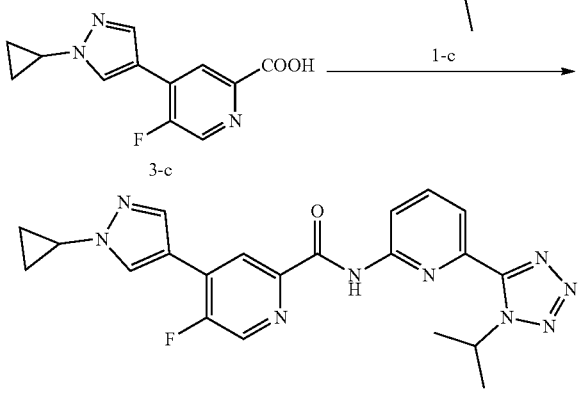

Example 3

Step 3-1

To a mixture of 1-cyclopropyl-4-(4,4,5,5-tetramethyl-1,3,2-dioxaborolan-2-yl)-1H-pyrazole (2.0 g, 8.55 mmol), 2-chloro-5-fluoro-4-iodopyridine (2 g, 7.77 mmol), and K₂CO₃ (3.2 g, 23.31 mmol) in dioxane (10 mL) and H₂O (2 mL) was added Pd(dppf)Cl₂ (568.5 mg, 0.78 mmol) at room temperature under nitrogen atmosphere. The resulting mixture was stirred at 80° C. for 3 h under nitrogen. After cooling to room temperature, the mixture was diluted with EtOAc (20 mL) and washed with water (10 mL*2) and brine (10 mL). The organic layer was dried over anhydrous Na₂SO₄, filtered, and was concentrated under reduced pressure. The residue was purified by silica gel column chromatography with PE/EtOAc (5:1) to afford compound 3-a (1.3 g, 70.41%) as a white solid.

Step 3-2

In a 50 mL autoclave a solution of compound 3-a (1.2 g, 5.0 mmol), Pd(dppf)Cl₂ (385 mg, 0.5 mmol), and Et₃N (1.52 g, 15 mmol) in BuOH (20 mL) was saturated with CO and stirred under 10 atm of CO at 70° C. for 16 hours. The resulting mixture was concentrated under reduced pressure. The residue was purified by silica gel column chromatography with PE/EtOAc (3:1) to afford compound 3-b (1.2 g, 78.35%) as a yellow oil.

Step 3-3

A solution of compound 3-b (600 mg, 1.98 mmol) in acetonitrile (5 mL) was treated with 1N HCl (5 mL) and the resulting mixture was stirred at 100° C. for 14 h under nitrogen atmosphere. Solvent was removed under reduced pressure. The residue was purified by reverse flash chromatography with 0-30% MeCN in water to afford compound 3-c (420 mg, 85.79%) as a white solid.

Step 3-4

To a solution of compound 3-c (250 mg, 1.01 mmol), HATU (499.8 mg, 1.31 mmol) and DIPEA (392.1 mg, 3.03 mmol) in DMF (5 mL) was added compound 1-c (227.2 mg, 1.11 mmol). The resulting mixture was stirred at room temperature for 4 h under nitrogen atmosphere. The residue was purified by reverse-phase flash chromatography with 40-70% MeCN in water to afford Example 3 (150 mg, 34.22%) as an off-white solid. [M+H]+, 434; 1H NMR (400 MHz, Chloroform-d) δ 10.39 (s, 1H), 8.60 (dd, J=8.4, 1.0 Hz, 1H), 8.53-8.51 (m, 2H), 8.12-8.09 (m, 3H), 8.02 (t, J=8.0 Hz, 1H), 5.85 (m, 1H), 3.73 (m, 1H), 1.76 (d, J=6.7 Hz, 6H), 1.26 (m, 2H), 1.12 (m, 2H).

Example 4

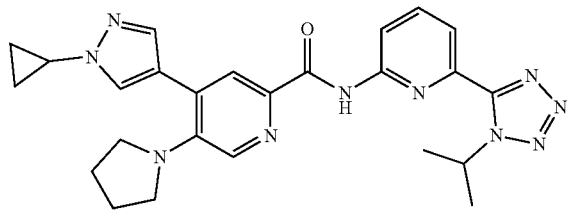 [SMILES: CC(C)n1nnnc1-c1cccc(NC(=O)c2cc(-c3cnn(C4CC4)c3)c(N3CCCC3)cn2)n1]

Example 3

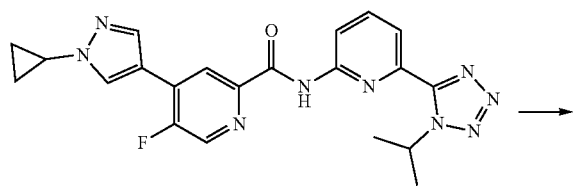

Example 4

Step 4-1

DBU (0.2 mL) was added to a solution of Example 3 (30 mg, 0.07 mmol) in pyrrolidine (1 mL). The resulting mixture was stirred at 80° C. for 4 h under nitrogen atmosphere. The reaction mixture was purified by reverse phase flash chromatography with 40-70% MeCN in water to afford Example 4 (17.9 mg, 53.37%) as a white solid. [M+H]+, 434; 1H NMR (400 MHz, Chloroform-d) δ 10.39 (s, 1H), 8.60 (dd, J=8.3, 1.0 Hz, 1H), 8.20 (s, 1H), 8.04-8.06 (m, 2H), 7.97 (t, J=8.0 Hz, 1H), 7.68 (m, 2H), 5.90 (m, 1H), 3.69 (m, 1H), 3.20 (m, 4H), 1.95 (m, 4H), 1.75 (d, J=6.7 Hz, 6H), 1.26 (m, 2H), 1.12 (m, 2H).

Example 5

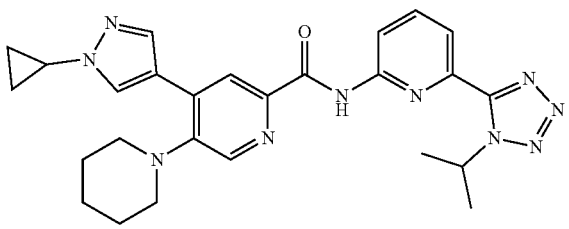 [SMILES: CC(C)n1nnnc1-c1cccc(NC(=O)c2cc(-c3cnn(C4CC4)c3)c(N3CCOCC3)cn2)n1]

Example 5 was prepared following a similar protocol as Example 4. [M+H]+, 499; 1H NMR (400 MHz, Chloroform-d) δ 10.47 (s, 1H), 8.61 (d, J=8.3 Hz, 1H), 8.38 (s, 1H), 8.25 (s, 1H), 8.20 (s, 1H), 8.16 (s, 1H), 8.08 (d, J=7.4 Hz, 1H), 7.99 (t, J=8.0 Hz, 1H), 5.88 (m, 1H), 3.71 (m, 1H), 3.03 (m, 4H), 1.76-1.70 (m, 10H), 1.70 (m, 2H), 1.26 (m, 2H), 1.14 (m, 2H).

Example 6

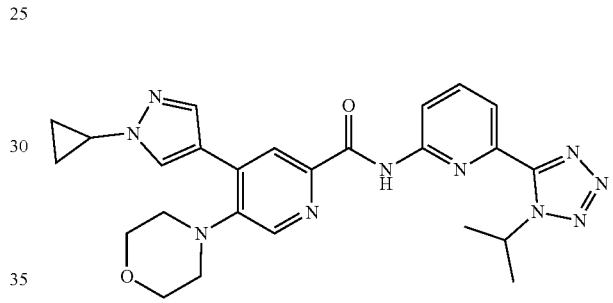

Example 6 was prepared following a similar protocol as Example 4. [M+H]+, 501; 1H NMR (400 MHz, Chloroform-d) δ 10.45 (s, 1H), 8.60 (dd, J=8.3, 1.0 Hz, 1H), 8.39 (s, 1H), 8.25 (s, 1H), 8.18-8.15 (m, 2H), 8.09 (dd, J=7.7, 1.0 Hz, 1H), 8.00 (t, J=8.3 Hz, 1H), 5.87 (m, 1H), 3.88 (t, J=4.4 Hz, 4H), 3.70 (m, 1H), 3.11 (t, J=4.4 Hz, 4H), 1.75 (d, J=6.7 Hz, 6H), 1.70 (m, 2H), 1.26 (m, 2H), 1.14 (m, 2H).

Example 7

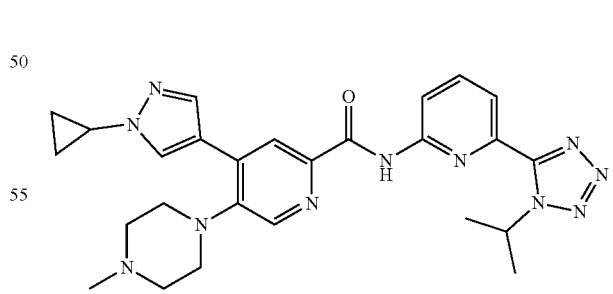

Example 7 was prepared following a similar protocol as Example 4. [M+H]+, 501; 1H NMR (400 MHz, Chloroform-d) δ 10.45 (s, 1H), 8.59 (dd, J=8.3, 1.0 Hz, 1H), 8.40 (s, 1H), 8.24 (s, 1H), 8.12 (s, 1H), 8.09 (dd, J=7.6, 0.8 Hz, 1H), 7.99 (t, J=8.0 Hz, 1H), 5.88 (m, 1H), 3.71 (m, 1H), 3.19 (t, J=4.4 Hz, 4H), 2.71 (t, J=4.4 Hz, 4H), 2.47 (s, 3H), 1.75 (d, J=6.7 Hz, 6H), 1.26 (m, 2H), 1.14 (m, 2H).

Example 8

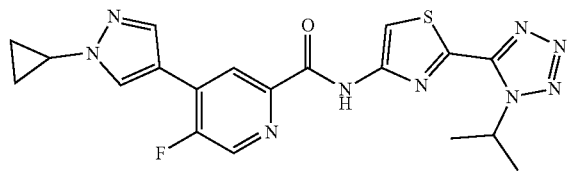 [SMILES: CC(C)n1nnnc1-c1nc(NC(=O)c2cc(-c3cnn(C4CC4)c3)c(F)cn2)cs1]

Example 8

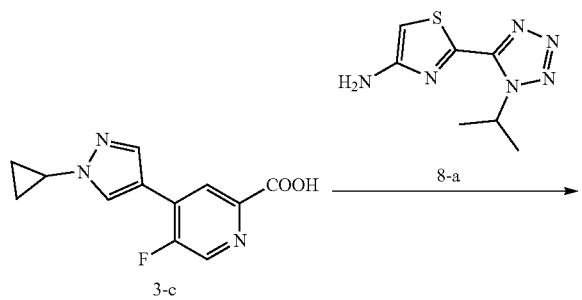

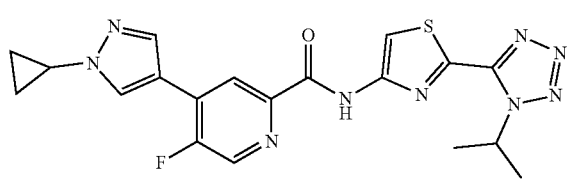

Example 8

Step 8-1

To a solution of compound 3-c (150 mg, 0.61 mmol), HATU (348 mg, 0.91 mmol) and DIPEA (239 mg, 1.87 mmol) in DMF (5 mL) was added compound 8-a (141 mg, 0.67 mmol) at room temperature under nitrogen atmosphere. The reaction mixture was stirred at rt for 2 h, and purified by reverse phase flash chromatography win 50-80% MeCN in water to afford Example 8 (130 mg, 48.8%) as a white solid. [M+H]$^+$ 440; $^1$H NMR (400 MHz, Chloroform-d) δ 10.58 (s, 1H), 8.51-8.50 (m, 2H), 8.17 (s, 1H), 8.11-8.08 (m, 2H), 5.88 (m, 1H), 3.73 (m, 1H), 1.74 (d, J=6.7 Hz, 6H), 1.25 (m, 2H), 1.16 (m, 2H).

Example 9

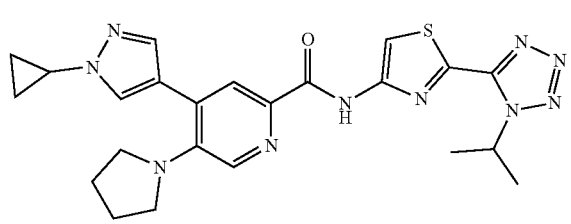 [SMILES: CC(C)n1nnnc1-c1nc(NC(=O)c2cc(-c3cnn(C4CC4)c3)c(N3CCCC3)cn2)cs1]

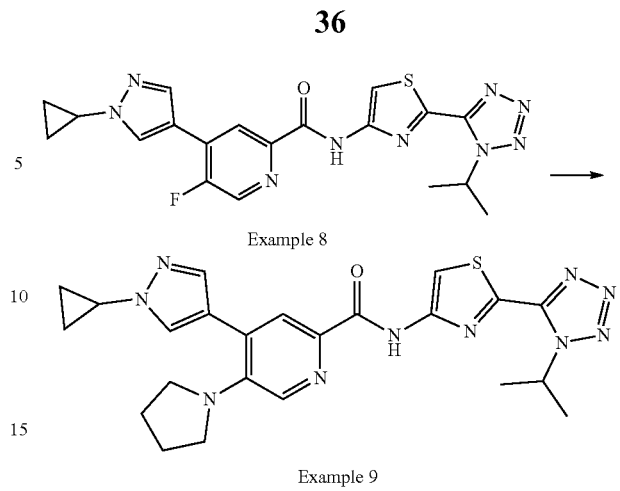

Example 8

Example 9

Example 9 was prepared following a similar protocol as shown in Step 4-1. [M+H]$^+$ 491; $^1$H NMR (400 MHz, Chloroform-d) δ 10.58 (s, 1H), 8.18 (s, 1H), 8.13 (s, 1H), 8.05 (s, 1H), 7.69-7.67 (m, 2H), 5.91 (m, 1H), 3.69 (m, 1H), 3.20 (t, J=6.4 Hz, 4H), 1.95 (t, J=6.4 Hz, 4H), 1.74 (d, J=6.7 Hz, 6H), 1.25 (m, 2H), 1.12 (m, 2H).

Example 10

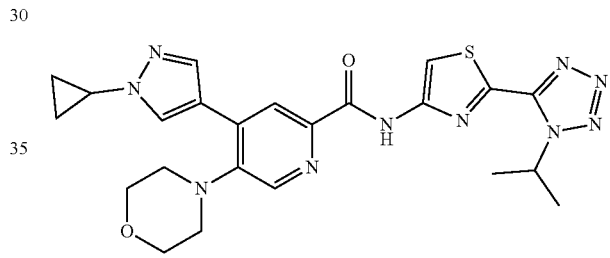

Example 10 was prepared following a similar protocol as shown in Step 4-1. [M+H]$^+$ 507; $^1$H NMR (400 MHz, Chloroform-d) δ 10.62 (s, 1H), 8.37 (s, 1H), 8.24 (s, 1H), 8.18 (s, 1H), 8.17-8.15 (m, 2H), 5.88 (m, 1H), 3.88 (t, J=4.4 Hz, 4H), 3.70 (m, 1H), 3.11 (t, J=4.4 Hz, 4H), 1.74 (d, J=6.6 Hz, 6H), 1.22 (m, 2H), 1.15 (m, 2H).

Example 11

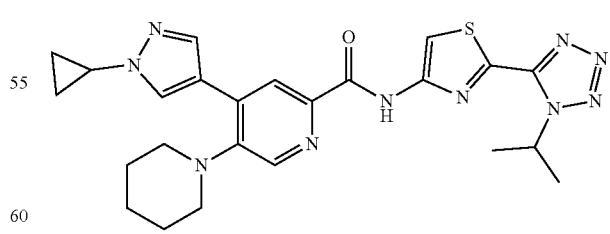

Example 11 was prepared following a similar protocol as shown in Step 4-1. [M+H]$^+$ 505; $^1$H NMR (400 MHz, Chloroform-d) δ 10.63 (s, 1H), 8.36 (s, 1H), 8.24 (s, 1H), 8.22-8.12 (m, 3H), 5.89 (m, 1H), 3.71 (m, 1H), 3.02 (t, J=5.2 Hz, 4H), 1.74-1.63 (m, 12H), 1.25 (m, 2H), 1.16 (m, 2H).

Example 12

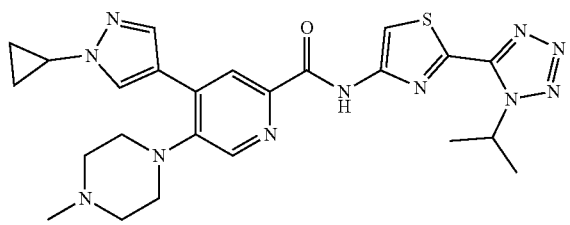 [SMILES: CC(C)n1nnnc1-c1nc(NC(=O)c2cc(-c3cnn(C4CC4)c3)c(N3CCN(C)CC3)cn2)cs1]

Example 12 was prepared following a similar protocol as shown in Step 4-1. [M+H]+ 520; ¹H NMR (400 MHz, Chloroform-d) δ 10.62 (s, 1H), 8.39 (s, 1H), 8.22 (s, 1H), 8.18 (s, 1H), 8.15 (s, 1H), 8.10 (s, 1H), 5.88 (m, 1H), 3.71 (m, 1H), 3.22 (t, J=4.9 Hz, 4H), 2.79 (s, 4H), 2.51 (s, 3H), 1.74 (d, J=6.7 Hz, 6H), 1.25 (m, 2H), 1.16 (m, 2H).

Example 13

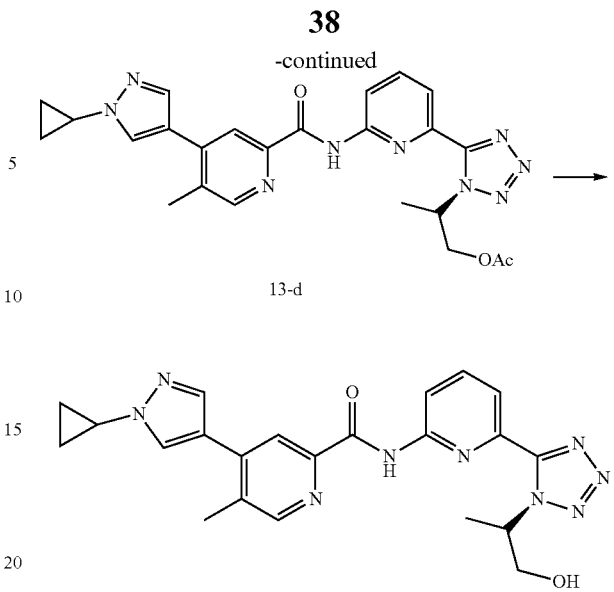

Step 13-1

A mixture of methyl 4-chloro-5-methylpyridine-2-carboxylate (200 mg, 1.08 mmol), 1-cyclopropyl-4-(4,4,5,5-tetramethyl-1,3,2-dioxaborolan-2-yl)-1H-pyrazole (302.7 mg, 1.29 mmol), Pd(dppf)Cl$_2$—CH$_2$Cl$_2$ (88.0 mg, 0.11 mmol), and K$_2$CO$_3$ (446.8 mg, 3.23 mmol) in dioxane (4 mL) and water (1 mL) was stirred at 80° C. for 2 h under nitrogen atmosphere. After cooling to room temperature, the residue was purified by reverse phase flash chromatography with 40-70% MeCN in H$_2$O to afford compound 13-a (60 mg, 21.64%) as a yellow solid.

Step 13-2

To a stirred mixture of compound 13-a (60 mg, 0.23 mmol) in MeOH (2 mL) and H$_2$O (1 mL) was added NaOH (18.7 mg, 0.47 mmol) at 0° C. The resulting mixture was stirred for 1 h at 50° C., cooled to rt, acidified to pH 3 with HCl (aq.), and concentrated under vacuum. The residue was purified by reverse phase flash chromatography with 10-50% MeCN/H$_2$O to afford compound 13-b (40 mg, 70.51%) as a white solid.

Step 13-3

To a solution of compound 13-b (40 mg, 0.16 mmol), HATU (91 mg, 0.24 mmol), and DIPEA (62 mg, 0.48 mmol) in DMF (2 mL) was added compound 13-c (52 mg, 0.20 mmol). The reaction mixture was stirred at room temperature for 16 h, and then purified by reverse phase flash chromatography with the 10-80% MeCN/H$_2$O to afford compound 13-d (30 mg, 37.4%) as a white solid.

Step 13-4

To a solution of compound 13-d (30 mg, 0.06 mmol) in MeOH (2 ml) was added K$_2$CO$_3$ (42 mg, 0.3 mmol). The reaction was stirred at rt for 2 h. Solid was removed by filtration. The filtrate was purified by reverse phase flash chromatography with 10-60% MeCN/H$_2$O to afford Example 13 (30 mg) as a white solid. [M+H]+ 446; ¹H NMR (400 MHz, Chloroform-d) δ 10.56 (s, 1H), 8.51 (s, 1H), 8.40 (dd, J=8.3, 1.0 Hz, 1H), 8.30 (s, 1H), 8.12 (dd, J=8.3, 1.0 Hz, 1H), 8.00 (t, J=8.0 Hz, 1H), 7.87 (s, 2H), 5.91 (m, 1H), 4.19 (d, J=5.6 Hz, 2H), 3.72 (m, 1H), 3.27 (s, 1H), 2.57 (s, 3H), 1.74 (d, J=6.8 Hz, 3H), 1.25 (m, 2H), 1.16 (m, 2H).

Example 14

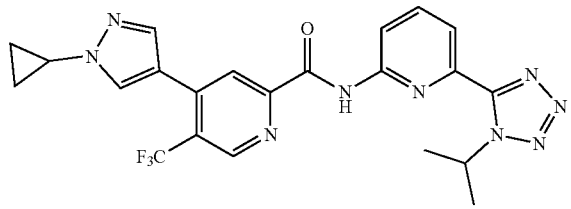 [SMILES: CC(C)n1nnnc1-c1cccc(NC(=O)c2cc(-c3cnn(C4CC4)c3)c(C(F)(F)F)cn2)n1]

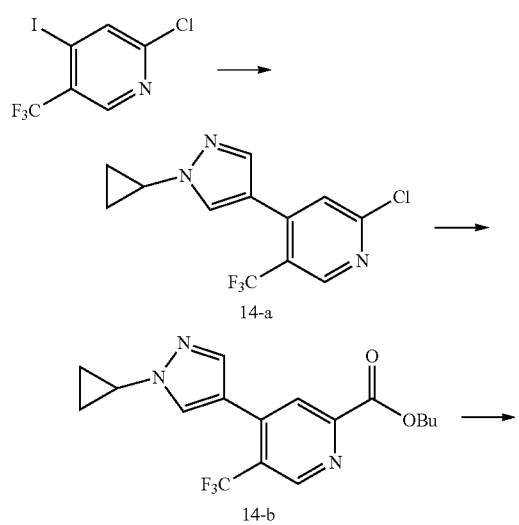

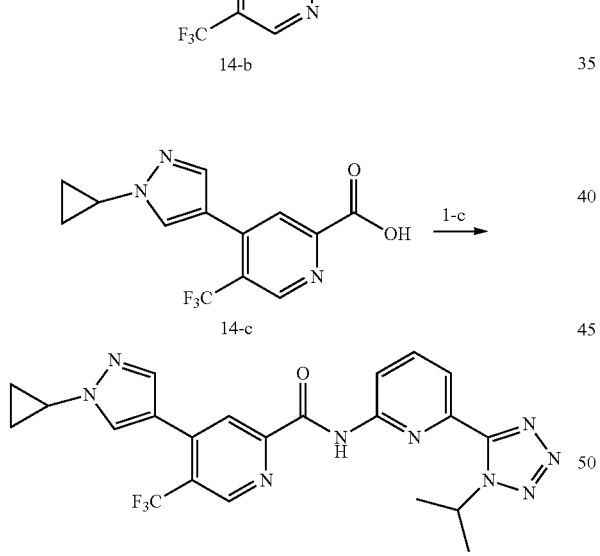

Example 14

Step 14-1

A mixture of 2-chloro-4-iodo-5-(trifluoromethyl)pyridine (1 g, 3.25 mmol), 1-cyclopropyl-4-(4,4,5,5-tetramethyl-1,3,2-dioxaborolan-2-yl)-1H-pyrazole (990 mg, 4.23 mmol), Pd(dppf)Cl$_2$ (375 mg, 0.3 mmol), and potassium carbonate (1.35 g, 9.75 mmol) in ethylene glycol dimethyl ether (5 mL) and H$_2$O (5 mL) was stirred at 100° C. for 3 hours. The reaction mixture was concentrated, and purified by Prep-HPLC with 0-100% MeCN/H$_2$O to afford compound 14-a (750 mg, 80%) as a yellow solid.

Step 14-2

In a 50-mL autoclave a solution of compound 14-a (750 mg, 2.61 mmol), Pd(dppf)Cl$_2$ (425 mg, 0.52 mmol), and TEA (957 mg, 7.83 mmol) in BuOH (10 mL) was stirred under 10 atm of CO at 70° C. overnight. The reaction mixture was concentrated in vacuo. Purification of the residue by Prep-HPLC with 0-100% MeCN/H$_2$O provided compound 14-b (660 mg, 72%) as a yellow solid.

Step 14-3

In a 50-mL autoclave aq. 1N HCl (5 mL) was added to a solution of compound 14-b (660 mg, 1.87 mmol) in MeCN (10 mL). The resulting solution was stirred at 100° C. overnight. The reaction mixture was concentrated, and the residue was purified by Prep-HPLC with 0-40% MeCN/H$_2$O to afford compound 14-c (420 mg, 76%) as a white solid.

Step 14-4

To a solution of compound 14-c (30 mg, 0.10 mmol), HATU (58 mg, 0.15 mmol), and 4-methylmorpholine (33 mg, 0.30 mmol) in DMF (2 mL) was added compound 1-c (24.8 mg, 0.12 mmol). The resulting mixture was stirred at room temperature overnight, and purified by Prep-HPLC with 0-80% MeCN/H$_2$O to afford Example 14 (16.5 mg) as a white solid. [M+H]$^+$ 484; $^1$H NMR (400 MHz, Chloroform-d) δ 10.48 (s, 1H), 9.01 (s, 1H), 8.60 (d, J=8.4, 1.0 Hz, 1H), 8.43 (s, 1H), 8.15 (dd, J=8.4, 1.0 Hz, 1H), 8.04 (t, J=8.4 Hz, 1H), 7.89 (d, J=13.1 Hz, 2H), 5.86 (m, 1H), 3.73 (m, 1H), 1.76 (d, J=6.7 Hz, 6H), 1.25 m, 2H), 1.16 (m, 2H).

Example 15

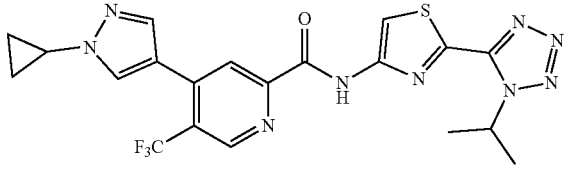 [SMILES: CC(C)n1nnnc1-c1nc(NC(=O)c2cc(-c3cnn(C4CC4)c3)c(C(F)(F)F)cn2)cs1]

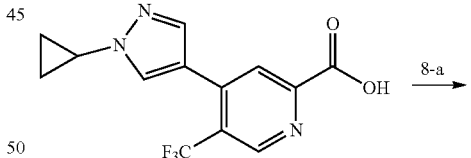

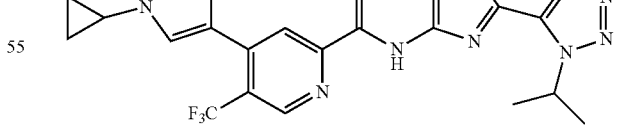

Example 15

Step 15-1

Example 15 was prepared following a similar protocol as shown in Step 14-4. [M+H]$^+$ 490; $^1$H NMR (400 MHz, Chloroform-d) δ 10.69 (s, 1H), 8.98 (s, 1H), 8.42 (s, 1H), 8.20 (s, 1H), 7.89 (d, J=14.2 Hz, 2H), 5.87 (m, 1H), 3.73 (m, 1H), 1.75 (d, J=6.7 Hz, 6H), 1.25 (m, 2H), 1.16 (m, 2H)

Example 16

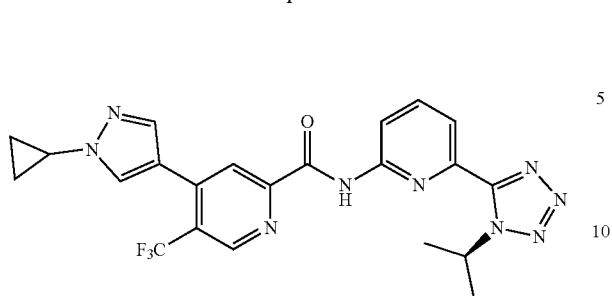

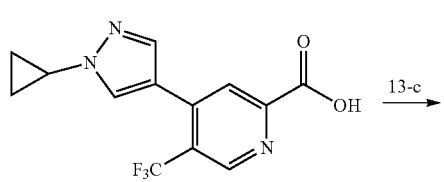

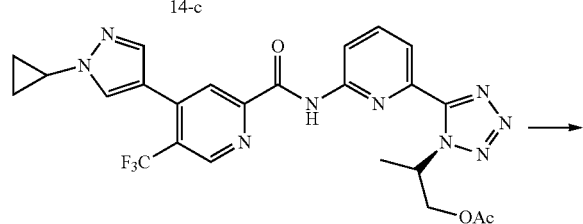

16-a

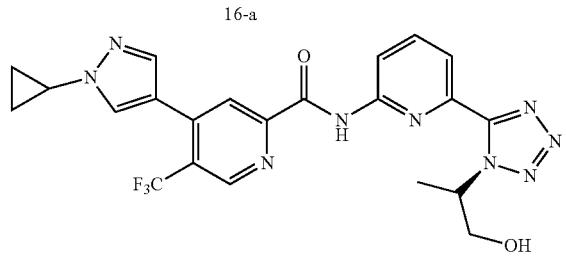

Example 16

Example 16 was prepared from compound 14-c following similar protocol as shown in Step 13-3 and Step 13-4. [M+H]⁺ 500; ¹H NMR (400 MHz, Chloroform-d) δ 10.51 (s, 1H), 9.00 (s, 1H), 8.44 (m, 2H), 8.17 (dd, J=8.0, 1.0 Hz, 1H), 8.05 (t, J=8.0 Hz, 1H), 7.90 (d, J=14.3 Hz, 2H), 5.88 (m, 1H), 4.20 (m, 2H), 3.73 (m, 1H), 1.74 (d, J=6.8 Hz, 3H), 1.23 (m, 2H), 1.14 (m, 2H).

Example 17

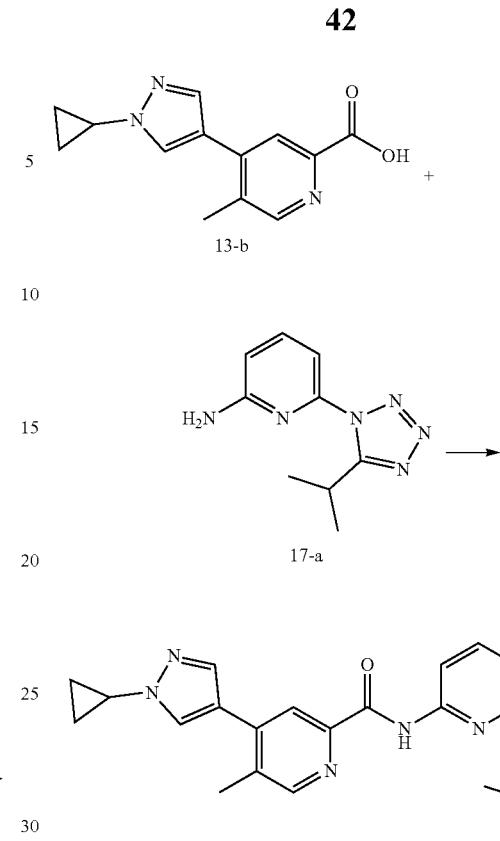

Example 17

Example 17 was prepared from compound 13-b and compound 17-a following similar protocol as shown in Step 14-4. [M+H]⁺ 430; ¹H NMR (400 MHz, Chloroform-d) δ 10.55 (s, 1H), 8.60 (d, J=8.3 Hz, 1H), 8.52 (s, 1H), 8.30 (s, 1H), 8.06 (t, J=8.1 Hz, 1H), 7.87 (s, 2H), 7.68 (d, J=7.8 Hz, 1H), 3.98 (m, 1H), 3.72 (m, 1H), 2.56 (s, 3H), 1.53 (d, J=6.9 Hz, 6H), 1.25 (m, 2H), 1.15 (m, 2H).

Example 18

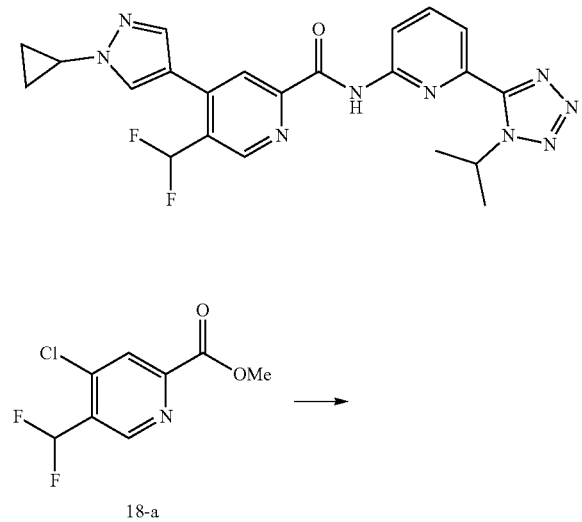

-continued

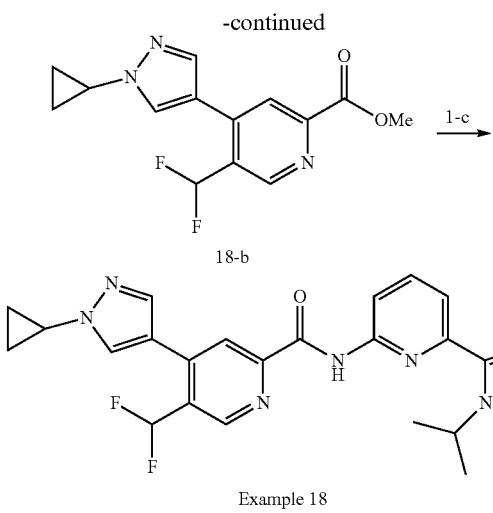

18-b

Example 18

Step 18-1

A mixture of compound 18-a (US 2017/0121308) (100 mg, 0.45 mmol), 1-cyclo propyl-4-(4,4,5,5-tetramethyl-1,3,2-dioxaborolan-2-yl)-1H-pyrazole (211 mg, 0.90 mmol), Pd(PPh$_3$)$_4$ (104 mg, 0.09 mmol), and K$_2$CO$_3$ (187 mg, 1.35 mmol) in dioxane (5 mL) was stirred at 100° C. for overnight under nitrogen atmosphere. Solvent was evaporated under vacuum, and the residue was purified by reverse phase column with 0-65% MeCN/H$_2$O to afford compound 18-b (95 mg, 71.8%) as a yellow solid.

Step 18-2

To an 8 mL seal tube were added compound 18-b (30 mg, 0.10 mmol), compound 1-c (43.0 mg, 0.20 mmol), Cs$_2$CO$_3$ (100 mg, 0.31 mmol) and DMF (5 mL). The resulting mixture was stirred at 100° C. for 3 hours under nitrogen atmosphere, and purified by reverse phase flash chromatography with 0-65% MeCN/H$_2$O to afford Example 18 (8 mg) as an off-white solid. [M+H]$^+$ 466; $^1$H NMR (400 MHz, Chloroform-d) δ 10.54 (s, 1H), 9.03 (s, 1H), 8.61 (dd, J=8.4, 0.9 Hz, 1H), 8.39 (s, 1H), 8.14 (dd, J=8.4, 0.9 Hz, 1H), 8.03 (t, J=8.4 Hz, 1H), 7.91-7.82 (m, 2H), 6.84 (t, J=54.0 Hz, 1H), 5.87 (m, 1H), 3.74 (m, 1H), 1.77 (d, J=6.7 Hz, 6H), 1.26 (m, 2H), 1.19 (m, 2H).

Example 19

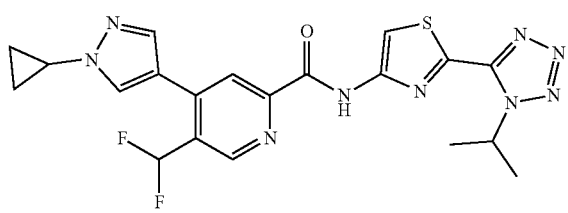 [SMILES: CC(C)n1nnnc1-c1nc(NC(=O)c2cc(-c3cnn(C4CC4)c3)c(C(F)F)cn2)cs1]

Example 19 was prepared from compound 18-b and compound 8-a following similar protocol as shown in Step 18-2. [M+H]+ 472; $^1$H NMR (400 MHz, Chloroform-d) δ 10.73 (s, 1H), 9.00 (s, 1H), 8.38 (s, 1H), 8.20 (s, 1H), 7.86 (d, J=17.1 Hz, 2H), 6.84 (t, J=54.0 Hz, 1H), 5.88 (m, 1H), 3.74 (m, 1H), 1.75 (d, J=6.7 Hz, 6H), 1.26 (m, 2H), 1.17 (m, 2H).

Example 20

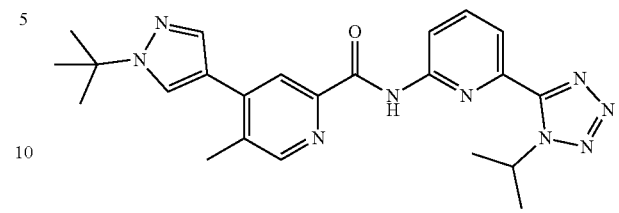

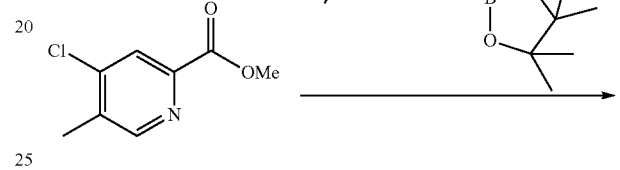

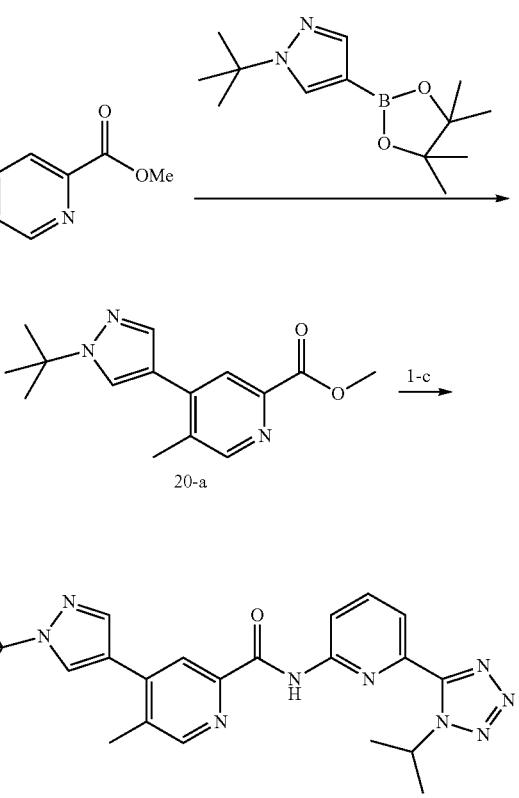

Example 20

Step 20-1

A mixture of methyl 4-chloro-5-methylpyridine-2-carboxylate (300 mg, 1.62 mmol), 1-tert-butyl-4-(4,4,5,5-tetramethyl-1,3,2-dioxaborolan-2-yl)-1H-pyrazole (606.5 mg, 2.42 mmol), Pd(PPh$_3$)$_4$ (373.5 mg, 0.32 mmol), K$_2$CO$_3$ (670.1 mg, 4.85 mmol) in dioxane (5 mL) was stirred at 100° C. under nitrogen atmosphere overnight. The mixture was cooled to room temperature and purified by reverse phase flash chromatography with 0-40% MeCN/H$_2$O to afford compound 20-a (140 mg, 31.69%) as a yellow oil.

Step 20-2

Example 20 was prepared from compound 20-a and compound 1-c following similar protocol as shown in Step-18-2. [M+H]$^+$ 446; $^1$H NMR (400 MHz, Chloroform-d) δ 10.57 (s, 1H), 8.62 (d, J=8.2 Hz, 1H), 8.53 (s, 1H), 8.34 (s, 1H), 8.10 (d, J=7.5 Hz, 1H), 8.01 (t, J=8.0 Hz, 1H), 7.94 (s, 2H), 5.89 (m, 1H), 2.59 (s, 3H), 1.76 (d, J=6.6 Hz, 6H), 1.70 (s, 9H).

Example 21

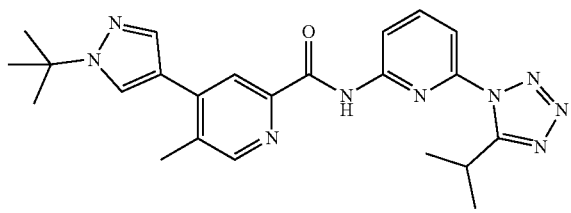 [SMILES: Cc1cnc(C(=O)Nc2cccc(-n3nnnc3C(C)C)n2)cc1-c1cnn(C(C)(C)C)c1]

Example 21 was prepared from compound 20-a and 17-a following similar protocol as show in Step 18-2. [M+H]+ 446; ¹H NMR (400 MHz, Chloroform-d) δ 10.58 (s, 1H), 8.61 (d, J=8.2 Hz, 1H), 8.53 (s, 1H), 8.33 (s, 1H), 8.07 (t, J=8.0 Hz, 1H), 7.97 (s, 1H), 7.94 (s, 1H), 7.69 (d, J=7.7 Hz, 1H), 4.00 (m, 1H), 2.59 (s, 3H), 1.71 (s, 9H), 1.54 (d, J=6.9 Hz, 6H).

Example 22

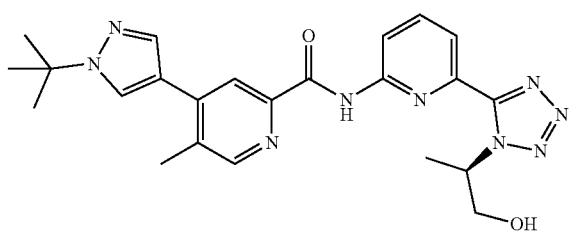 [SMILES: Cc1cnc(C(=O)Nc2cccc(-c3nnnn3[C@H](C)CO)n2)cc1-c1cnn(C(C)(C)C)c1]

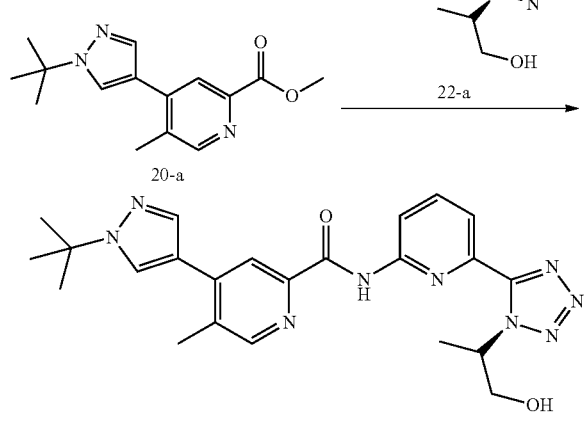

Example 22 was prepared from compound 20-a and compound 22-a following similar protocol as show in Step 18-2. [M+H]⁺ 462; ¹H NMR (400 MHz, Chloroform-d) δ 10.60 (s, 1H), 8.51 (s, 1H), 8.41 (d, J=8.3 Hz, 1H), 8.33 (s, 1H), 8.13 (d, J=7.6 Hz, 1H), 8.02 (t, J=8.0 Hz, 1H), 7.93 (s, 1H), 7.92 (s, 1H), 5.90 (m, 1H), 4.19 (d, J=6.0 Hz, 2H), 2.59 (s, 3H), 1.74 (d, J=7.6 Hz, 3H), 1.69 (s, 9H).

Example 23

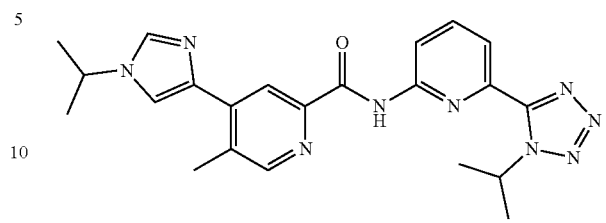

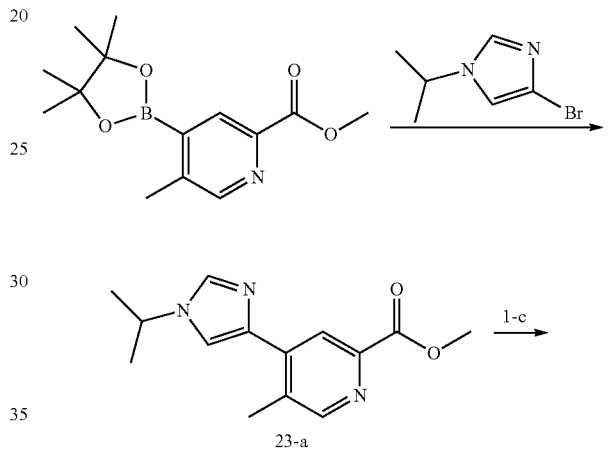

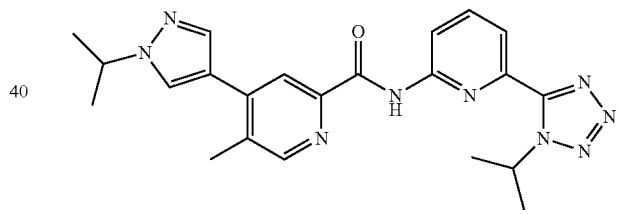

Step 23-1

A mixture of methyl 5-methyl-4-(4,4,5,5-tetramethyl-1,3,2-dioxaborolan-2-yl)pyridine-2-carboxylate (300 mg, 1.08 mmol), 4-bromo-1-(propan-2-yl)-1H-imidazole (307.0 mg, 1.62 mmol), Pd(PPh₃)₄ (250.2 mg, 0.22 mmol), K₂CO₃ (448.8 mg, 3.25 mmol) in dioxane (5 ml) was stirred at 100° C. under nitrogen atmosphere overnight. The resulting mixture was concentrated under vacuum and purified by reverse phase flash chromatography with 0-37% MeCN/H₂O to afford compound 23-a (180 mg, 64.12%) as yellow oil.

Step 23-2

Example 23 was prepared from compound 23-a following similar protocol as shown in Step 18-2. [M+H]⁺ 432; ¹H NMR (400 MHz, Chloroform-d) δ 10.57 (s, 1H), 8.68 (s, 1H), 8.63 (d, J=8.4 Hz, 1H), 8.51 (s, 1H), 8.08 (d, J=7.5 Hz, 1H), 7.99 (t, J=7.9 Hz, 1H), 7.71 (s, 1H), 7.44 (s, 1H), 5.90 (m, 1H), 4.46 (m, 1H), 2.68 (s, 3H), 1.75 (d, J=6.6 Hz, 6H), 1.60 (d, J=6.7 Hz, 6H).

Example 24

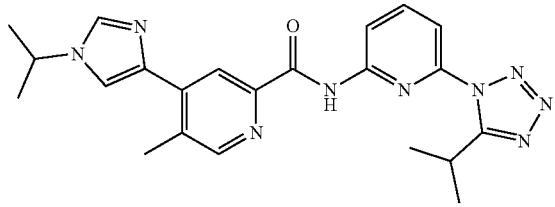 [SMILES: Cc1cnc(C(=O)Nc2cccc(-n3nnnc3C(C)C)n2)cc1-c1cn(C(C)C)cn1]

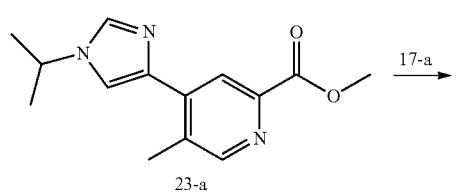

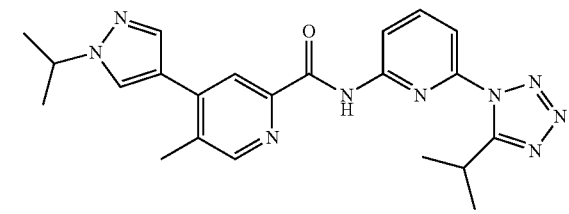

Example 24

Example 24 was prepared from compound 23-a and compound 17-a following similar protocol as shown in Step 18-2. [M+H]+ 432; ¹H NMR (400 MHz, Chloroform-d) δ 10.58 (s, 1H), 8.69 (s, 1H), 8.62 (d, J=8.2 Hz, 1H), 8.51 (s, 1H), 8.05 (t, J=8.1 Hz, 1H), 7.74 (s, 1H), 7.67 (d, J=7.6 Hz, 1H), 7.44 (d, J=1.3 Hz, 1H), 4.47 (m, 1H), 4.00 (m, 1H), 2.68 (s, 3H), 1.61 (d, J=6.7 Hz, 6H), 1.53 (d, J=6.9 Hz, 6H).

Example 25

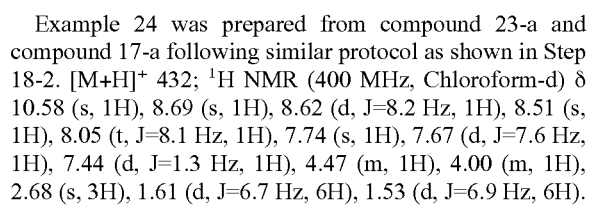

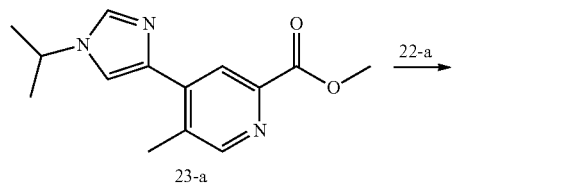

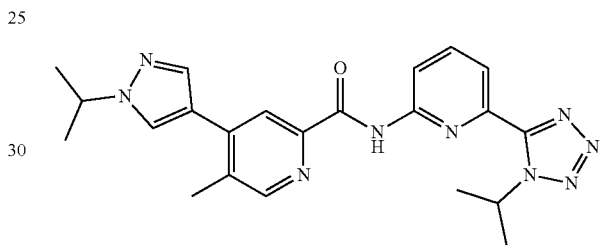

Example 25

Example 25 was prepared from compound 23-a and compound 22-a following similar protocol as shown in Step 18-2. [M+H]+ 448; ¹H NMR (400 MHz, Chloroform-d) δ 10.61 (s, 1H), 8.68 (s, 1H), 8.51 (s, 1H), 8.38 (d, J=8.3 Hz, 1H), 8.12 (d, J=7.6 Hz, 1H), 8.00 (t, J=8.0 Hz, 1H), 7.76 (s, 1H), 7.45 (s, 1H), 5.94 (m, 1H), 4.48 (m, 1H), 4.17 (m, 2H), 2.68 (s, 3H), 1.74 (d, J=6.8 Hz, 3H), 1.62 (d, J=6.7 Hz, 6H).

Example 26

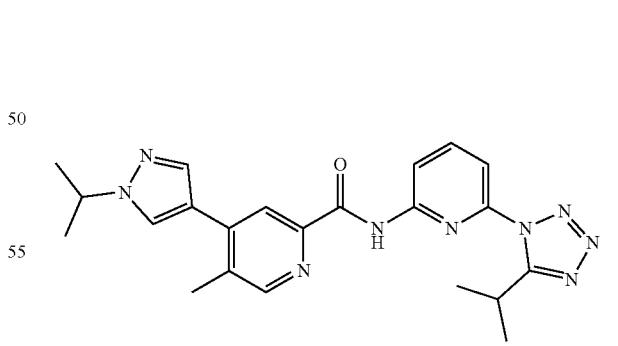

Example 26 was prepared following similar protocol as shown in example 20. [M+H]+ 432; ¹H NMR (400 MHz, Chloroform-d) δ 10.55 (s, 1H), 8.62 (d, J=8.3 Hz, 1H), 8.53 (s, 1H), 8.33 (s, 1H), 8.10 (d, J=7.6 Hz, 1H), 8.01 (t, J=8.0 Hz, 1H), 7.91 (s, 1H), 7.85 (s, 1H), 5.88 (m, 1H), 4.62 (m, 1H), 2.58 (s, 3H), 1.76 (d, J=6.6 Hz, 6H), 1.62 (d, J=6.7 Hz, 6H).

Example 27

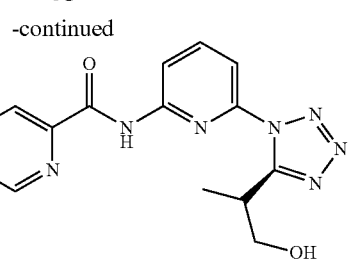

Example 27 was prepared following similar protocol as shown in example 21. [M+H]+ 432; ¹H NMR (400 MHz, Chloroform-d) δ 10.63 (s, 1H), 8.60 (d, J=8.3 Hz, 1H), 8.52 (s, 1H), 8.34 (s, 1H), 8.07 (t, J=8.1 Hz, 1H), 7.92 (s, 1H), 7.86 (s, 1H), 7.70 (d, J=7.8 Hz, 1H), 4.64 (m, 1H), 4.02 (m, 1H), 2.59 (s, 3H), 1.63 (d, J=6.7 Hz, 6H), 1.54 (d, J=6.9 Hz, 6H).

Example 28

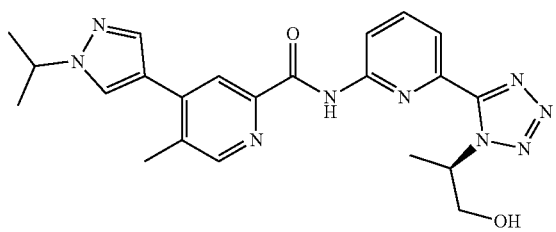 [SMILES: Cc1cnc(C(=O)Nc2cccc(-c3nnnn3[C@H](C)CO)n2)cc1-c1cnn(C(C)C)c1]

Example 28 was prepared following similar protocol as shown in example 22. [M+H]+ 448; ¹H NMR (400 MHz, Chloroform-d) δ 10.69 (s, 1H), 8.52 (s, 1H), 8.41 (d, J=8.0 Hz, 1H), 8.33 (s, 1H), 8.15 (d, J=7.1 Hz, 1H), 8.02 (t, J=8.0 Hz, 1H), 7.93 (s, 1H), 7.87 (s, 1H), 5.94 (m, 1H), 4.63 (m, 1H), 4.19 (m, 2H), 2.60 (s, 3H), 1.74 (d, J=6.8 Hz, 3H), 1.63 (d, J=6.7 Hz, 6H).

Example 29

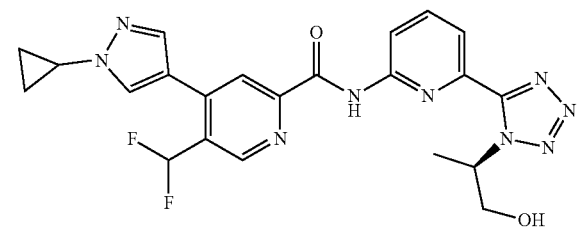 [SMILES: C[C@H](CO)n1nnnc1-c1cccc(NC(=O)c2cc(-c3cnn(C4CC4)c3)c(C(F)F)cn2)n1]

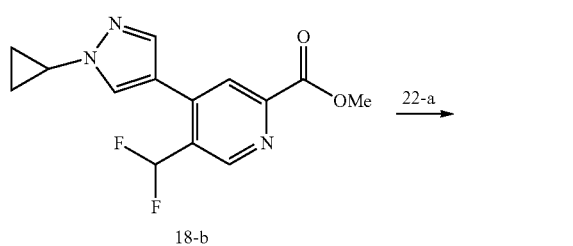

Step 29-1

To a solution of compound 22-a (60.1 mg, 0.27 mmol) in DCM (5 mL) at 0° C. was added Me₃Al in toluene (0.4 mL, 0.568 mmol) under nitrogen atmosphere. The mixture was stirred for 1 hour and a solution of compound 18-b (80 mg, 0.27 mmol) in DCM (1 mL) was added. The resulting mixture was stirred at 35° C. for 16 h, diluted with DCM, and washed with Rochelles salt and brine. The organic layer was dried over anhydrous Na₂SO₄ and concentrated under reduced pressure. The crude product was purified by prep-HPLC with 35-60% MeCN/H₂O to afford Example 29 (11.8 mg) as a white solid. [M+H]+ 482; ¹H NMR (400 MHz, Chloroform-d) δ 10.57 (s, 1H), 9.02 (s, 1H), 8.46-8.37 (m, 2H), 8.17 (d, J=7.6 Hz, 1H), 8.05 (t, J=8.1 Hz, 1H), 7.90 (s, 1H), 7.85 (s, 1H), 6.84 (t, J=53.2 Hz, 1H), 5.90 (m, 1H), 4.27-4.17 (m, 2H), 3.75 (m, 1H), 1.75 (d, J=6.8 Hz, 3H), 1.27 (m, 2H), 1.17 (m, 2H).

Example 30

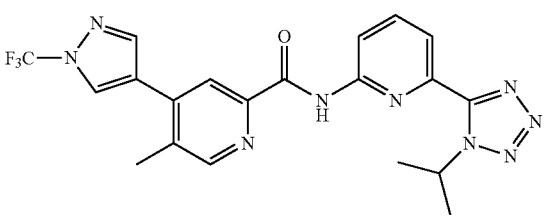 [SMILES: Cc1cnc(C(=O)Nc2cccc(-c3nnnn3C(C)C)n2)cc1-c1cnn(C(F)(F)F)c1]

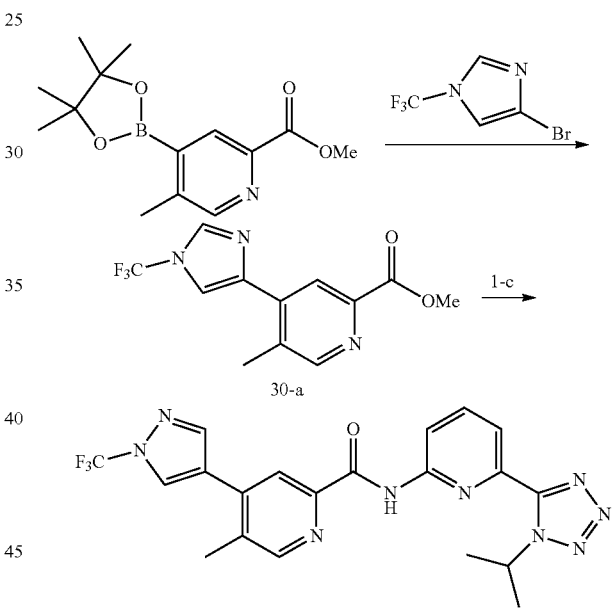

Example 30

A mixture of methyl 5-methyl-4-(4,4,5,5-tetramethyl-1,3,2-dioxaborolan-2-yl)picolinate (300 mg, 1.08 mmol), 4-bromo-1-(trifluoromethyl)-1H-pyrazole (256 mg, 1.19 mmol), Pd(PPh₃)₄ (104 mg, 0.1 mmol) and K₂CO₃ (447 mg, 3.24 mmol) in dioxane (10 mL) was stirred at 100° C. under nitrogen atmosphere for 1 h. Solvent was removed under reduced pressure. The residue was purified by reverse phase flash chromatography with 0-60% CH₃CN in water to afford compound 30-a (175 mg, 56.7%) as a white solid.

Step 30-2

Example 30 was prepared from compound 30-a and compound 1-c following similar protocol as shown in Step 29-1. [M+1]+458; ¹H NMR (400 MHz, Chloroform-d) δ 10.50 (s, 1H), 8.62-8.60 (m, 2H), 8.33 (s, 1H), 8.18 (s, 1H), 8.15-8.06 (m, 2H), 8.01 (t, J=8.0 Hz, 1H), 5.87 (m, 1H), 2.58 (s, 3H), 1.76 (d, J=6.7 Hz, 6H).

Example 31

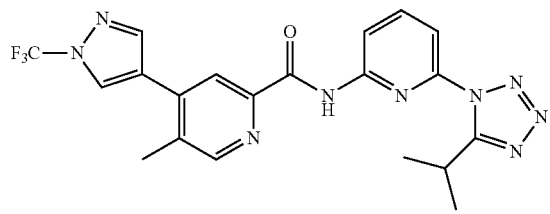 [SMILES: Cc1cnc(C(=O)Nc2cccc(-n3nnnc3C(C)C)n2)cc1-c1cnn(C(F)(F)F)c1]

Example 31 was prepared from compound 30-a and compound 17-a following similar protocol as shown in Step 29-1. [M+1]+458; ¹H NMR (400 MHz, Chloroform-d) δ 10.51 (s, 1H), 8.61-8.59 (m, 2H), 8.32 (s, 1H), 8.17 (s, 1H), 8.13 (s, 1H), 8.08 (t, J=8.1 Hz, 1H), 7.70 (d, J=7.8 Hz, 1H), 3.97 (m, 1H), 2.58 (s, 3H), 1.53 (d, J=6.9 Hz, 7H).

Example 32

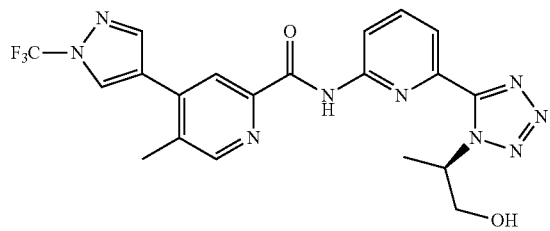 [SMILES: Cc1cnc(C(=O)Nc2cccc(-c3nnnn3[C@H](C)CO)n2)cc1-c1cnn(C(F)(F)F)c1]

Example 32 was prepared from compound 30-a and compound 22-a following similar protocol as shown in Step 29-1. [M+1]+474; ¹H NMR (400 MHz, Chloroform-d) δ 10.53 (s, 1H), 8.61 (s, 1H), 8.42 (d, J=8.3 Hz, 1H), 8.33 (s, 1H), 8.18 (s, 1H), 8.16-8.13 (m, 2H), 8.02 (t, J=8.0 Hz, 1H), 5.90 (m, 1H), 4.21 (m, 2H), 2.59 (s, 3H), 1.74 (d, J=6.8 Hz, 3H).

Example 33

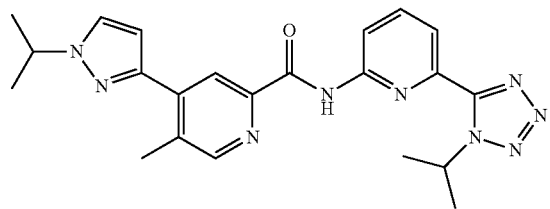 [SMILES: Cc1cnc(C(=O)Nc2cccc(-c3nnnn3C(C)C)n2)cc1-c1ccn(C(C)C)n1]

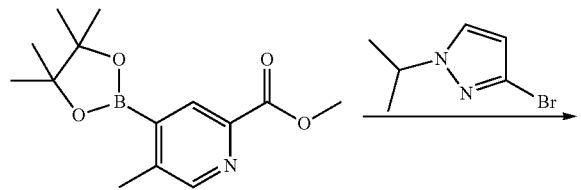

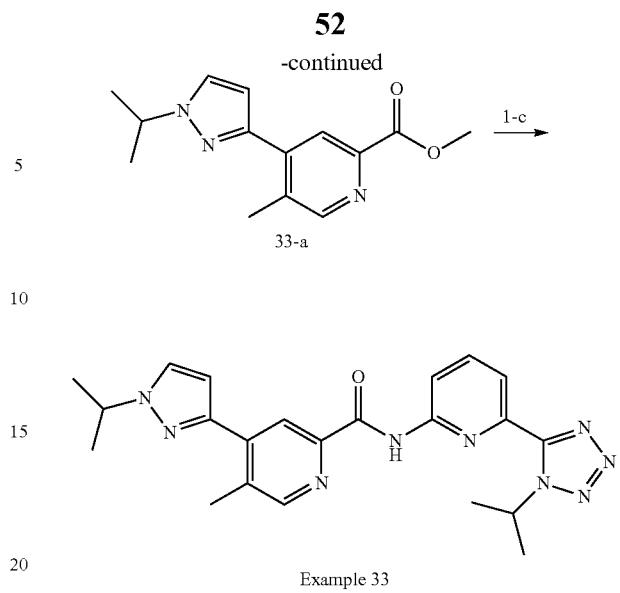

Step 33-1

A mixture of methyl 5-methyl-4-(4,4,5,5-tetramethyl-1,3,2-dioxaborolan-2-yl)pyridine-2-carboxylate (250 Ng, 0.90 mmol), 3-bromo-1-(propan-2-yl)-H-pyrazole (341.1 g, 1.80 mmol), Pd(PPh₃)₄ (208.5 mg, 0.18 mmol), and K₂CO₃ (374.0 mg, 2.71 mmol) in dioxane (5 mL) was stirred at 100° C. under nitrogen atmosphere overnight. The reaction mixture was concentrated under reduced pressure. The residue was purified by reverse phase flash chromatography with 0-40% MeCN/H₂O to afford compound 33-a (200 mg, 85.50%) as a yellow oil.

Step 33-2

Example 33 was prepared from compound 33-a and compound 1-c following similar protocol as shown in Step 29-1. [M+H]⁺ 432. ¹H NMR (400 MHz, Chloroform-d) δ 10.60 (s, 1H), 8.67-8.59 (m, 2H), 8.56 (s, 1H), 8.10 (d, J=7.6 Hz, 1H), 8.00 (t, J=8.0 Hz, 1H), 7.56 (d, J=2.3 Hz, 1H), 6.70 (d, J=2.4 Hz, 1H), 5.92 (m, J=6.7 Hz, 1H), 4.61 (m, J=6.7 Hz, 1H), 2.70 (s, 3H), 1.76 (d, J=6.6 Hz, 6H), 1.61 (d, J=6.6 Hz, 6H).

Example 34

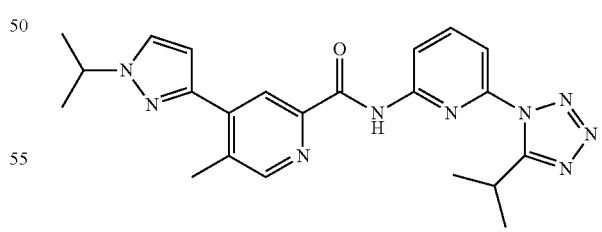

Example 34 was prepared from compound 33-a and compound 17-a following similar protocol as shown in Step 29-1. [M+H]⁺ 432. ¹H NMR (400 MHz, Chloroform-d) δ 10.58 (s, 1H), 8.65-8.57 (m, 2H), 8.54 (s, 1H), 8.05 (t, J=8.0 Hz, 1H), 7.68 (d, J=7.8 Hz, 1H), 7.56 (d, J=2.3 Hz, 1H), 6.69 (d, J=2.3 Hz, 1H), 4.60 (m, J=6.8 Hz, 1H), 4.00 (m, J=6.9 Hz, 1H), 2.69 (s, 3H), 1.61 (d, J=6.7 Hz, 6H), 1.54 (d, J=6.9 Hz, 6H).

Example 35

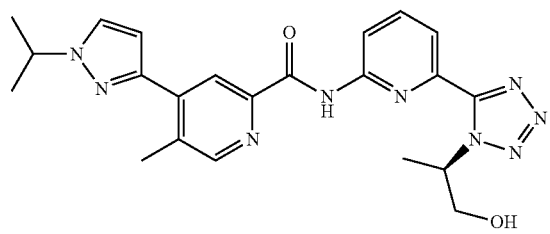 [SMILES: Cc1cnc(C(=O)Nc2cccc(-c3nnnn3[C@H](C)CO)n2)cc1-c1ccn(C(C)C)n1]

Example 35 was prepared from compound 33-a and compound 22-a following similar protocol as shown in Step 29-1. [M+H]⁺ 448. ¹H NMR (400 MHz, Chloroform-d) δ 10.63 (s, 1H), 8.59 (s, 1H), 8.53 (s, 1H), 8.42 (d, J=8.3 Hz, 1H), 8.11 (d, J=7.6 Hz, 1H), 8.00 (t, J=8.0 Hz, 1H), 7.56 (d, J=2.3 Hz, 1H), 6.70 (d, J=2.3 Hz, 1H), 5.94 (m, J=6.5 Hz, 1H), 4.60 (m, J=6.7 Hz, 1H), 4.19 (d, J=6.0 Hz, 2H), 3.30 (s, 1H), 2.70 (s, 3H), 1.74 (d, J=6.8 Hz, 3H), 1.61 (d, J=6.7 Hz, 6H)

Example 36

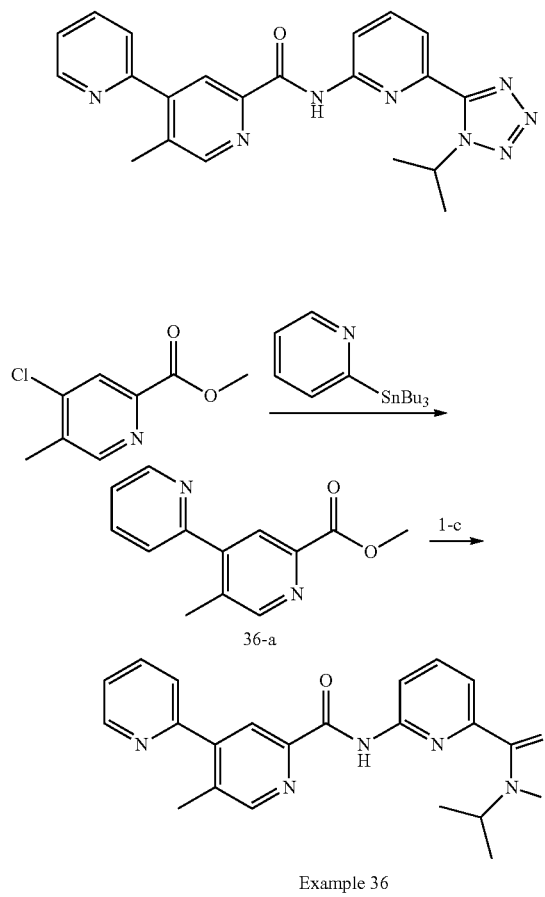

Step 36-1

In a microwave vial a mixture of methyl 4-chloro-5-methylpyridine-2-carboxylate (100 mg, 0.54 mmol), 2-(tributylstannyl) pyridine (190 mg, 0.52 mmol), and Pd(PPh₃)₄ (49 mg, 0.04 mmol) in DMF (2 mL) was heated in microwave at 160° C. for 1 hour. Solvent was removed in vacuo and the residue was purified by prep-HPLC with 0-90% MeCN/H₂O to afford 60 mg (49%) compound 36-a.

Step 36-2

Example 36 was prepared from compound 36-a and compound 1-c following a similar protocol as shown in Step 18-2. [M+H]+ 401; ¹H NMR (400 MHz, Chloroform-d) δ 10.55 (s, 1H), 8.79 (d, J=4.4 Hz, 1H), 8.67-8.59 (m, 2H), 8.39 (s, 1H), 8.10 (d, J=7.2 Hz, 1H), 8.00 (t, J=8.0 Hz, 1H), 7.90 (td, J=7.8, 1.8 Hz, 1H), 7.57 (d, J=7.8 Hz, 1H), 7.41 (dd, J=7.6, 4.9 Hz, 1H), 5.90 (m, 1H), 2.55 (s, 3H), 1.77 (d, J=6.7 Hz, 6H).

Example 37

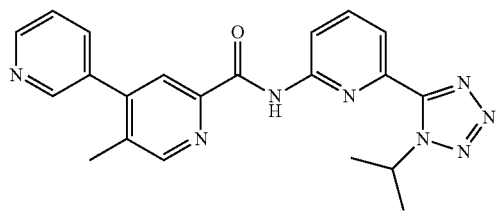 [SMILES: Cc1cnc(C(=O)Nc2cccc(-c3nnnn3C(C)C)n2)cc1-c1cccnc1]

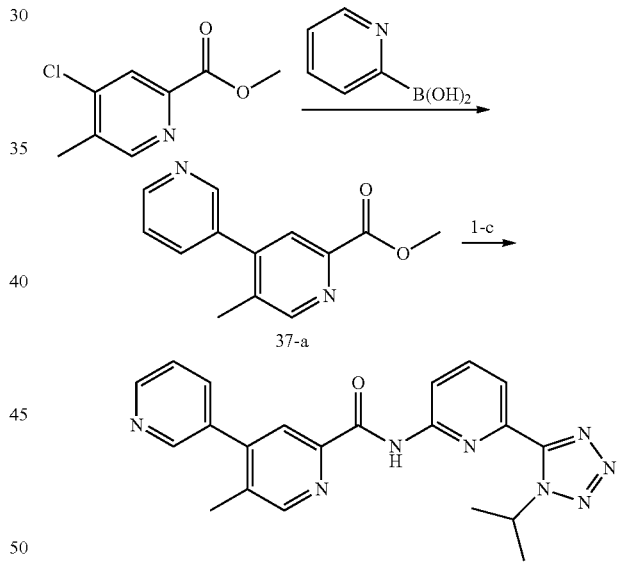

Step 37-1

A mixture of methyl 4-chloro-5-methylpyridine-2-carboxylate (100 mg, 0.54 mmol), (pyridin-3-yl)boronic acid (100 mg, 0.80 mmol), Pd(PPh₃)₄ (62 mg, 0.05 mmol), and K₂CO₃ (224 mg, 1.62 mmol) in dioxane (5 mL) was stirred at 100° C. overnight. Solvent was removed in vacuo and the residue was purified by prep-HPLC with 0-80% MeCN/H₂O to provide 60 mg (48.8%) of compound 37-a as a yellow solid.

Step 37-2

Example 37 was prepared from compound 37-a following a similar protocol as shown in Step 18-2. [M+H]⁺ 401; ¹H NMR (400 MHz, Chloroform-d) δ 10.52 (s, 1H), 8.75 (d, J=4.8 Hz, 1H), 8.71 (s, 1H), 8.66 (s, 1H), 8.61 (d, J=8.0 Hz, 1H), 8.24 (s, 1H), 8.10 (d, J=7.6 Hz, 1H), 8.01 (t, J=8.0 Hz, 1H), 7.77 (d, J=8.0 Hz, 1H), 7.49 (dd, J=7.8, 4.8 Hz, 1H), 5.88 (m, 1H), 2.45 (s, 3H), 1.77 (d, J=6.7 Hz, 6H).

Example 38

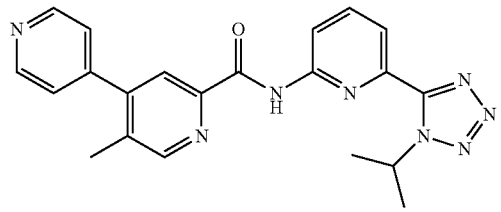 [SMILES: Cc1cnc(C(=O)Nc2cccc(-c3nnnn3C(C)C)n2)cc1-c1ccncc1]

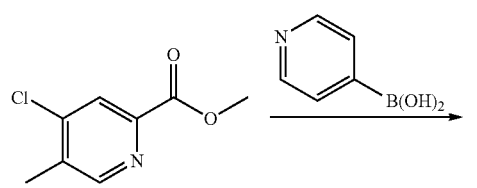

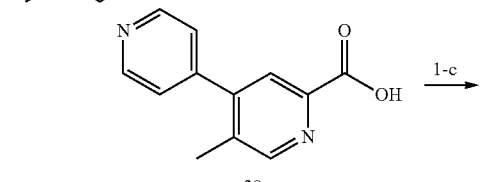

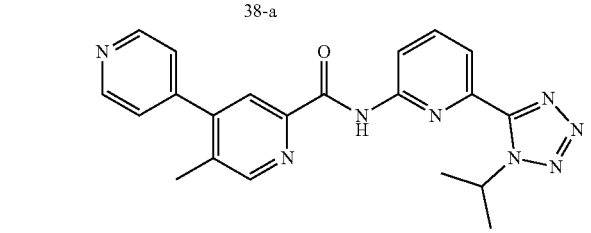

Example 38

Example 39

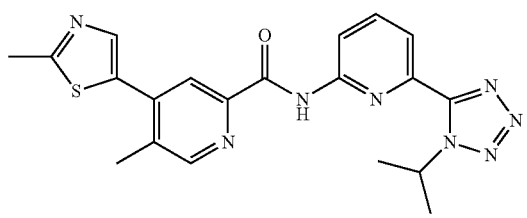 [SMILES: Cc1ncc(-c2cc(C(=O)Nc3cccc(-c4nnnn4C(C)C)n3)ncc2C)s1]

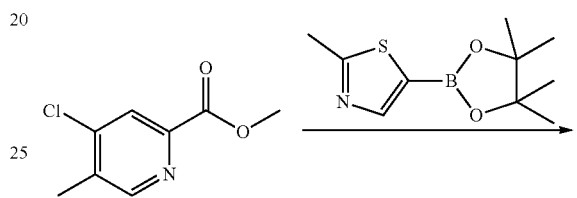

Example 39

Step 38-1

A mixture of methyl 4-chloro-5-methylpyridine-2-carboxylate (100 mg, 0.54 mmol), (pyridin-4-yl)boronic acid (100 mg, 0.80 mmol), Pd(PPh$_3$)$_4$ (62 mg, 0.05 mmol), and K$_2$CO$_3$ (223 mg, 1.62 mmol) in ethylene glycol dimethyl ether (5 mL) and H$_2$O (1 mL) was stirred at 100° C. overnight. Solvent was removed in vacuo and the residue was purified by prep-HPLC with 0-60% MeCN/H$_2$O to afford 70 mg (61%) of compound 38-a as a yellow solid.

Step 38-2

Compound 1-c (57 mg, 0.28 mmol) was added into a mixture of compound 38-a (50 mg, 0.23 mmol), HATU (266 mg, 0.46 mmol), and 4-methylmorpholine (118 mg, 1.17 mmol) in DMF (2 mL). The resulting solution was stirred at room temperature overnight. The solution was purified by prep-HPLC with 0-80% MeCN/H$_2$O to afford 8.3 mg of Example 38 as a white solid. [M+H]$^+$401; $^1$H NMR (400 MHz, Chloroform-d) δ 10.51 (s, 1H), 8.80 (d, J=5.0 Hz, 2H), 8.66 (s, 1H), 8.59 (d, J=8.4 Hz, 1H), 8.22 (s, 1H), 8.11 (d, J=7.6 Hz, 1H), 8.01 (t, J=8.0 Hz, 1H), 7.35 (d, J=5.2 Hz, 2H), 5.88 (m, 1H), 2.44 (s, 3H), 1.77 (d, J=6.7 Hz, 6H).

Step 39-1

A mixture of methyl 4-chloro-5-methylpyridine-2-carboxylate (100 mg, 0.54 mmol), 2-methyl-5-(4,4,5,5-tetramethyl-1,3,2-dioxaborolan-2-yl)-1,3-thiazole (242.6 mg, 1.08 mmol), Pd(PPh$_3$)$_4$ (124.5 mg, 0.11 mmol), and K$_2$CO$_3$ (223.4 mg, 1.62 mmol) in dioxane (5 mL) was stirred at 100° C. under nitrogen atmosphere overnight. The reaction mixture was concentrated under vacuum and purified by reverse phase flash chromatograph with 0-33% MeCN/H$_2$O to afford compound 39-a (40 mg, 29.90%) as a yellow solid.

Step 39-2

Example 39 was prepared from compound 39-a and compound 1-c following similar protocol as shown in Step 18-2. [M+H]$^+$ 421; $^1$H NMR (400 MHz, Chloroform-d) δ 10.49 (s, 1H), 8.61 (t, J=4.2 Hz, 2H), 8.34 (s, 1H), 8.10 (d, J=7.5 Hz, 1H), 8.01 (t, J=8.0 Hz, 1H), 7.91 (s, 1H), 5.87 (m, 1H), 2.84 (s, 3H), 2.60 (s, 3H), 1.76 (d, J=6.7 Hz, 6H).

Example 40

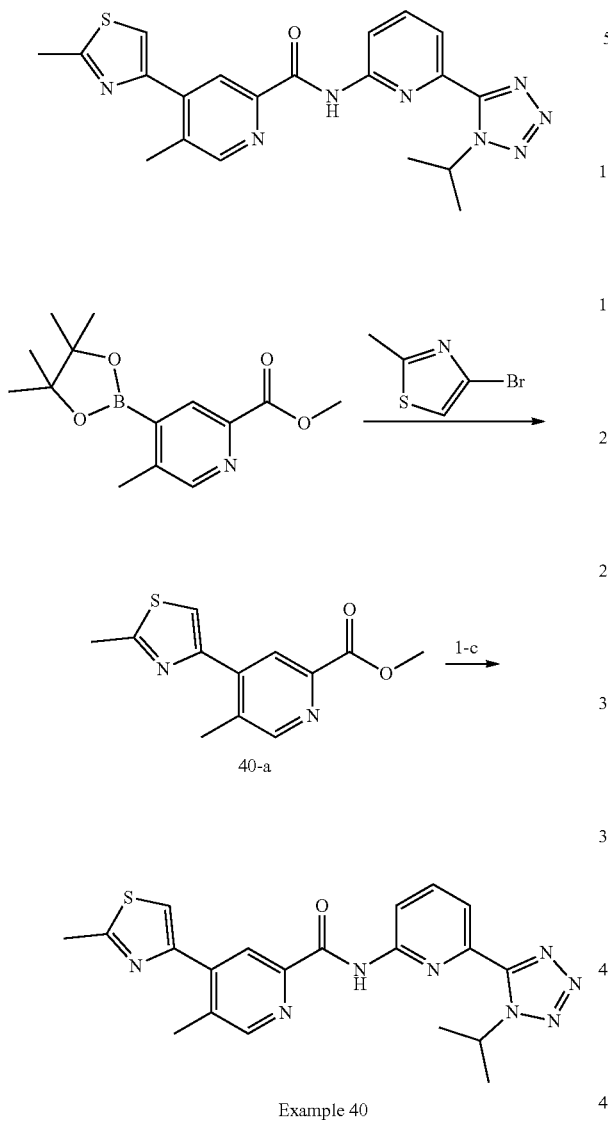

Step 40-1

A mixture of methyl 5-methyl-4-(4,4,5,5-tetramethyl-1,3,2-dioxaborolan-2-yl)pyridine-2-carboxylate (100 mg, 0.36 mmol), 4-bromo-2-methyl-1,3-thiazole (128.5 mg, 0.72 mmol), Pd(PPh$_3$)$_4$ (83.4 mg, 0.07 mmol), and K$_2$CO$_3$ (149.6 mg, 1.08 mmol) in dioxane (5 mL) was stirred at 100° C. under nitrogen atmosphere overnight. The reaction mixture was concentrated under reduced pressure and the residue was purified by reverse phase flash chromatography with 0-36% MeCN/H$_2$O to afford compound 40-a (80 mg, 89.29%) as a brown oil.

Step 40-2

Example 40 was prepared from compound 40-a and compound 1-c following similar protocol as shown in Step 18-2. [M+H]$^+$ 421; $^1$H NMR (400 MHz, Chloroform-d) δ 10.54 (s, 1H), 8.66-8.57 (m, 3H), 8.09 (d, J=7.5 Hz, 1H), 8.00 (t, J=8.0 Hz, 1H), 7.48 (s, 1H), 5.89 (m, 1H), 2.83 (s, 3H), 2.64 (s, 3H), 1.76 (d, J=6.6 Hz, 6H).

Example 41

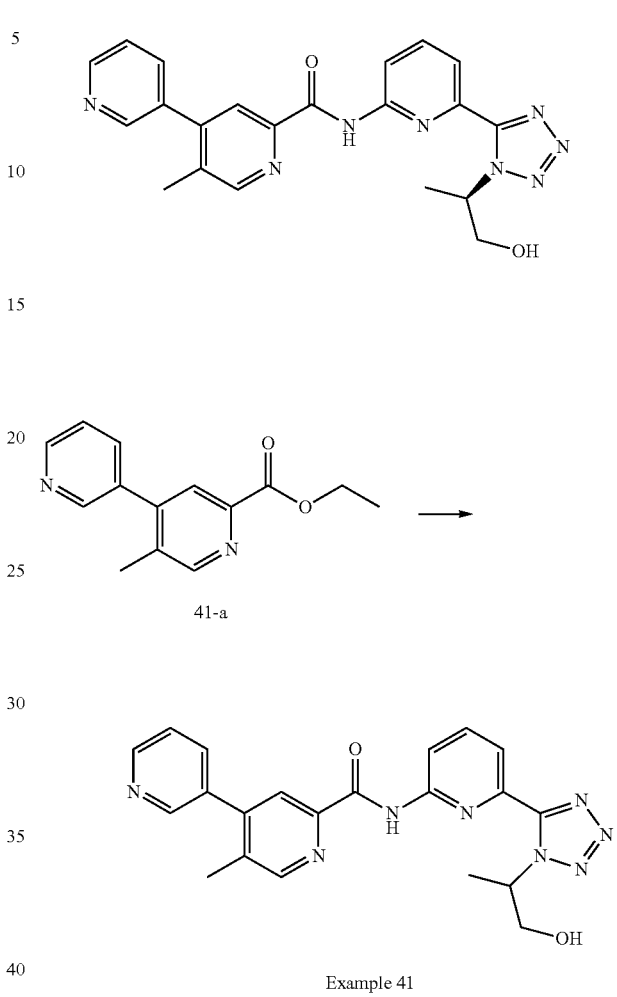

Compound 41-a was prepared following the same protocol described in Step 37-1. Example 41 was prepared from compound 41-a and compound 22-a following similar protocol described in Step 29-1. [M+H]$^+$ 417. $^1$H NMR (400 MHz, Chloroform-d) δ 10.55 (s, 1H), 8.76 (s, 1H), 8.72 (s, 1H), 8.64 (s, 1H), 8.42 (d, J=8.3 Hz, 1H), 8.23 (s, 1H), 8.13 (d, J=7.2 Hz, 1H), 8.02 (t, J=8.1 Hz, 1H), 7.78 (d, J=7.7 Hz, 1H), 7.51 (s, 1H), 5.92 (m, 1H), 4.20 (d, J=5.3 Hz, 2H), 2.46 (s, 3H), 1.75 (d, J=6.9 Hz, 3H).

Example 42

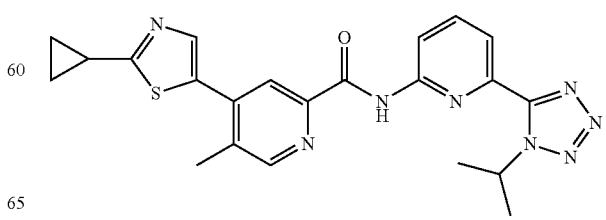

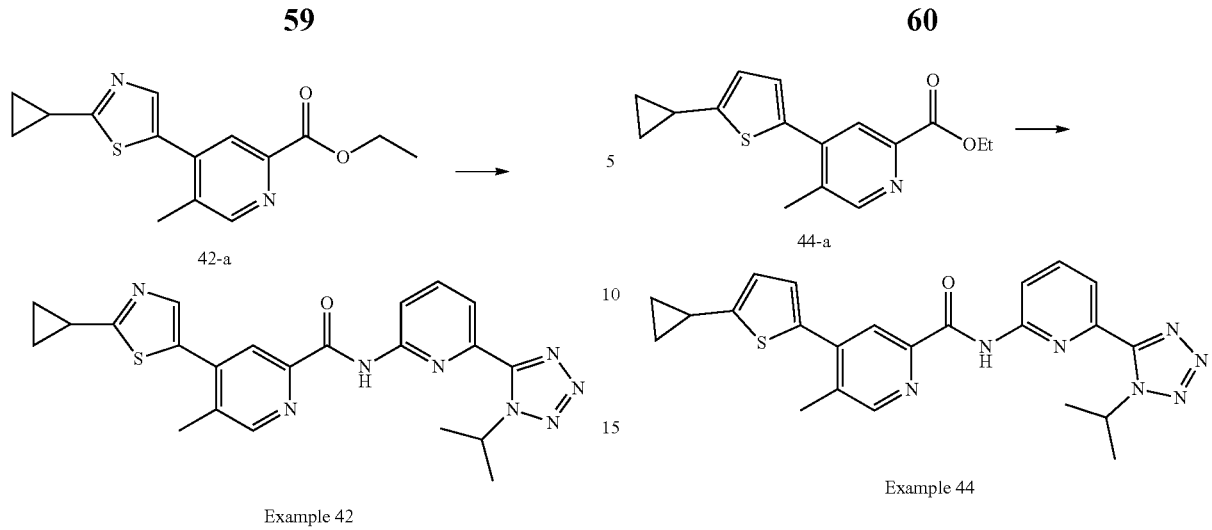

Example 42

Compound 42-a was prepared following a similar protocol as shown in Step 40-1. Example 42 was prepared from compound 42-a and 1-c following a similar protocol as shown in Step 29-1. [M+H]+ 447. $^1$H NMR (400 MHz, Chloroform-d) δ 10.49 (s, 1H), 8.69-8.60 (m, 2H), 8.33 (s, 1H), 8.11 (d, J=7.6 Hz, 1H), 8.02 (t, J=7.9 Hz, 1H), 7.88 (s, 1H), 5.87 (m, 1H), 2.60 (s, 3H), 2.43 (s, 1H), 1.76 (d, J=6.7 Hz, 6H), 1.28 (d, J=8.1 Hz, 2H), 1.21 (d, J=8.1 Hz, 2H).

Example 43

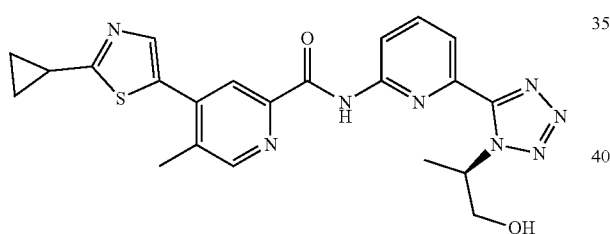

Example 43 was prepared from compound 42-a and 22-a following a similar protocol as shown in Step 29-1. [M+H]+ 463. $^1$H NMR (400 MHz, Chloroform-d) δ 10.53 (s, 1H), 8.58 (s, 1H), 8.42 (d, J=8.3 Hz, 1H), 8.32 (s, 1H), 8.14 (d, J=7.6 Hz, 1H), 8.02 (t, J=8.0 Hz, 1H), 7.85 (s, 1H), 5.90 (m, 1H), 4.19 (d, J=6.0 Hz, 2H), 3.15 (s, 1H), 2.60 (s, 3H), 2.41 (m, 1H), 1.74 (d, J=6.8 Hz, 3H), 1.30-1.16 (m, 4H).

Example 44

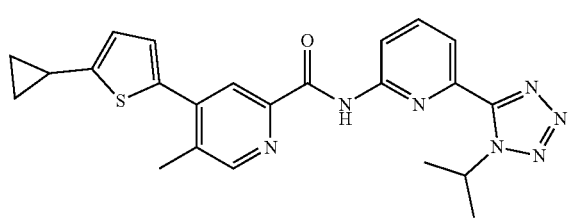 [SMILES: Cc1cnc(C(=O)Nc2cccc(-c3nnnn3C(C)C)n2)cc1-c1ccc(C2CC2)s1]

Compound 44-a was prepared following a similar protocol as shown in Step 40-1. Example 44 was prepared from compound 44-a and 1-c following a similar protocol as shown in Step 29-1. [M+H]+ 446. $^1$H NMR (400 MHz, Chloroform-d) δ 10.52 (s, 1H), 8.62 (d, J=8.3 Hz, 1H), 8.53 (s, 1H), 8.37 (s, 1H), 8.10 (m, 1H), 8.00 (t, J=7.9 Hz, 1H), 7.26 (d, J=3.7 Hz, 1H), 6.87 (d, J=3.7 Hz, 1H), 5.89 (m, 1H), 2.63 (s, 3H), 2.17 (m, 1H), 1.76 (d, J=6.6 Hz, 6H), 1.16-1.07 (m, 2H), 0.87-0.85 (m, 2H).

Example 45

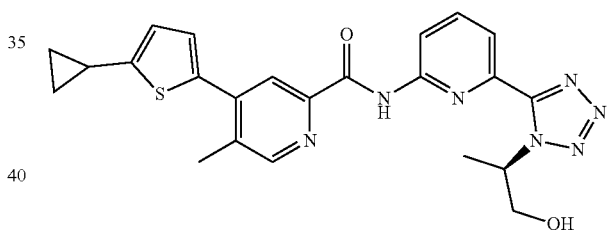

Example 45 was prepared from compound 44-a and 22-a following a similar protocol as shown in Step 29-1. [M+H]+ 462. $^1$H NMR (400 MHz, Chloroform-d) δ 10.55 (s, 1H), 8.52 (s, 1H), 8.41 (d, J=8.3 Hz, 1H), 8.36 (s, 1H), 8.12 (d, J=7.6 Hz, 1H), 8.01 (t, J=8.0 Hz, 1H), 7.26 (d, J=3.8 Hz, 1H), 6.87 (d, J=3.7 Hz, 1H), 5.92 (m, 1H), 4.19 (t, J=6.3 Hz, 2H), 3.51 (s, 1H), 3.22 (t, J=6.4 Hz, 1H), 2.62 (s, 3H), 2.17 (m, 1H), 1.74 (d, J=6.8 Hz, 3H), 1.16-1.07 (m, 2H), 0.87-0.85 (m, 2H).

Example 46

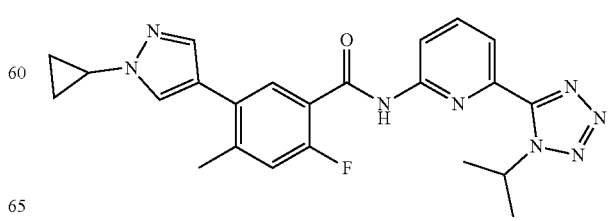

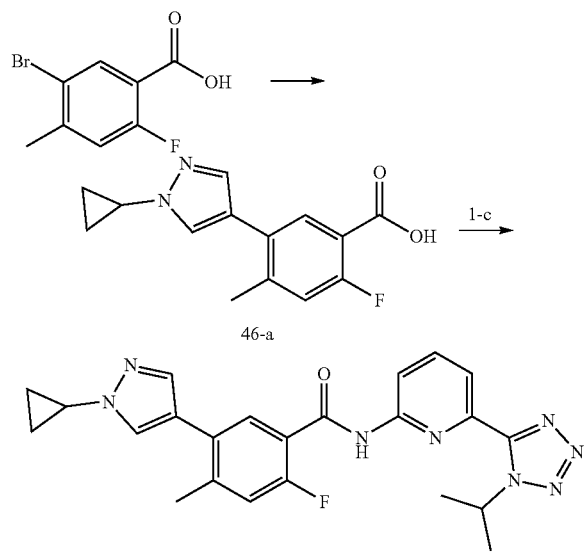

Example 46

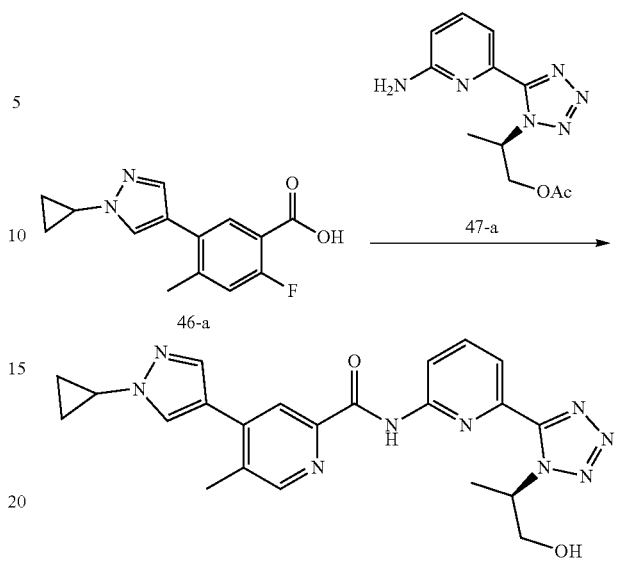

Example 47

Step 46-1

A mixture of 5-bromo-2-fluoro-4-methylbenzoic acid (150 mg, 0.64 mmol), 1-cyclopropyl-4-(4,4,5,5-tetramethyl-1,3,2-dioxaborolan-2-yl)-1H-pyrazole (226.0 mg, 0.97 mmol), Pd(PPh$_3$)$_4$ (74.4 mg, 0.06 mmol) and K$_2$CO$_3$ (266.9 mg, 1.93 mmol) in DME (5 mL) and H$_2$O (1 mL) was stirred at 100° C. under nitrogen atmosphere for 1 h. The mixture was allowed to cool to room temperature and acidified to pH 3~4 with conc.HCl. Solvent was removed in vacuo and the residue was purified by reverse phase flash chromatography with 0-40% MeCN/H$_2$O to afford compound 46-a (150 mg, 89.54%) as a light brown solid.

Step 46-2

A mixture of compound 46-a (50 mg, 0.19 mmol) and 1-Chloro-N,N,2-trimethyl-1-propenylamine (30.8 mg, 0.23 mmol) in DCM (2 mL) was stirred at room temperature for 1 h. To the above solution was added pyridine (45.6 mg, 0.58 mmol) and compound 1-c (58.9 mg, 0.29 mmol). The resulting mixture was stirred at room temperature for 1 h. Solvent was removed under vacuum and the residue was purified by reverse phase flash chromatography with 0-60% CH$_3$CN/H$_2$O to afford Example 46 (12.5 mg) as a white solid. [M+H]$^+$ 447; $^1$H NMR (400 MHz, Chloroform-d) δ 9.18 (d, J=16.6 Hz, 1H), 8.55 (d, J=8.3 Hz, 1H), 8.14-8.08 (m, 2H), 7.99 (t, J=8.0 Hz, 1H), 7.65-7.63 (m, 2H), 7.13 (d, J=13.1 Hz, 1H), 5.75 (m, 1H), 3.68 (m, 1H), 2.49 (s, 3H), 1.74 (d, J=6.7 Hz, 6H), 1.19 (m, 2H), 1.12 (m, 2H).

Example 47

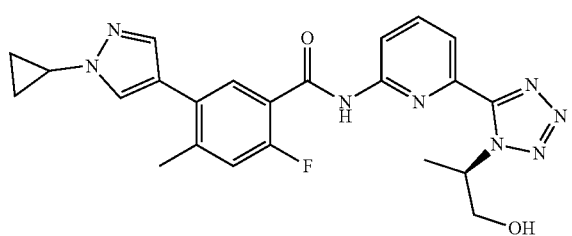 [SMILES: Cc1cc(F)c(C(=O)Nc2cccc(-c3nnnn3[C@H](C)CO)n2)cc1-c1cnn(C2CC2)c1]

Example 47

Step 47-1

A mixture of compound 46-a (50 mg, 190 mmol) and 1-Chloro-N,N,2-trimethyl-1-propenylamine (30.8 mg, 230 mmol) in DCM (2 mL) was stirred at room temperature for 1 h. Pyridine (45.6 mg, 0.58 mmol) and compound 47-a (75.6 mg, 0.29 mmol) were added and the resulting mixture was stirred at room temperature for 1 h. The reaction was quenched with MeOH (2 mL) and K$_2$CO$_3$ (53.1 mg, 0.38 mmol) was added. The resulting mixture was stirred at room temperature for 5 h. Solvent was removed in vacuo and the residue was purified by reverse phase flash chromatography with 0-60% MeCN/H$_2$O to afford Example 47 (9.5 mg) as a white solid. [M+H]$^+$ 463; $^1$H NMR (400 MHz, Chloroform-d) δ 9.18 (d, J=16.6 Hz, 1H), 8.49 (d, J=8.3 Hz, 1H), 8.14-8.11 (m, 2H), 8.02 (t, J=8.0 Hz, 1H), 7.65-7.60 (m, 2H), 7.13 (d, J=13.1 Hz, 1H), 5.76 (m, 1H), 4.23-4.12 (m, 2H), 3.69 (m, 1H), 2.50 (s, 3H), 1.73 (d, J=6.8 Hz, 3H), 1.22 (m, 2H), 1.09 (m, 2H).

Example 48

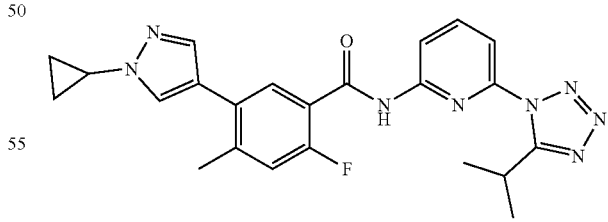

Example 48 was prepared from compound 46-a and compound 17-a following the same protocol as shown in Step 46-2. [M+H]+ 463; $^1$H NMR (400 MHz, Chloroform-d) δ 9.15 (d, J=16.7 Hz, 1H), 8.54 (d, J=8.3 Hz, 1H), 8.13 (d, J=8.2 Hz, 1H), 8.05 (t, J=8.1 Hz, 1H), 7.72 (d, J=7.9 Hz, 1H), 7.68-7.65 (m, 1H), 7.14 (d, J=13.1 Hz, 1H), 3.90 (m, 1H), 3.68 (m, 1H), 2.50 (s, 3H), 1.53 (d, J=6.9 Hz, 6H), 1.22 (m, 2H), 1.14 (m, 2H).

Example 49

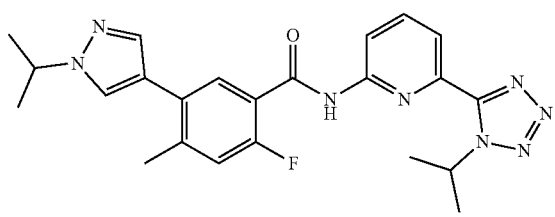 [SMILES: Cc1cc(F)c(C(=O)Nc2cccc(-c3nnnn3C(C)C)n2)cc1-c1cnn(C(C)C)c1]

Example 49 was prepared following the same protocol as described in Example 46. [M+H]⁺ 449; ¹H NMR (400 MHz, Chloroform-d) δ 9.20 (d, J=16.6 Hz, 1H), 8.55 (d, J=8.4 Hz, 1H), 8.15 (d, J=8.4 Hz, 1H), 8.10 (d, J=7.6 Hz, 1H), 8.00 (t, J=8.0 Hz, 1H), 7.68 (s, 1H), 7.60 (s, 1H), 7.13 (d, J=13.2 Hz, 1H), 5.76 (m, 1H), 4.58 (m, 1H), 2.51 (s, 3H), 1.74 (d, J=6.7 Hz, 6H), 1.59 (d, J=6.7 Hz, 6H).

Example 50

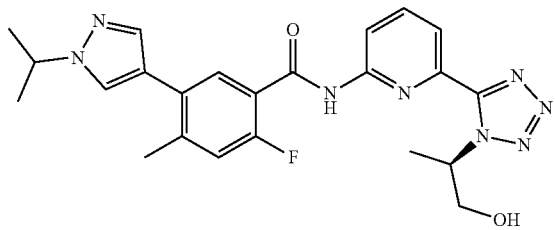 [SMILES: Cc1cc(F)c(C(=O)Nc2cccc(-c3nnnn3[C@H](C)CO)n2)cc1-c1cnn(C(C)C)c1]

Example 50 was prepared following the same protocol as described in Example 47. [M+H]⁺ 465; ¹H NMR (400 MHz, Chloroform-d) δ 9.22 (d, J=16.5 Hz, 1H), 8.49 (d, J=8.3 Hz, 1H), 8.19-8.09 (m, 2H), 8.02 (t, J=7.9 Hz, 1H), 7.68 (s, 1H), 7.61 (s, 1H), 7.14 (d, J=13.2 Hz, 1H), 5.71 (m, 1H), 4.59 (m, 1H), 4.18 (m, 2H), 2.51 (s, 3H), 1.73 (d, J=6.8 Hz, 3H), 1.60 (d, J=6.7 Hz, 6H).

Example 51

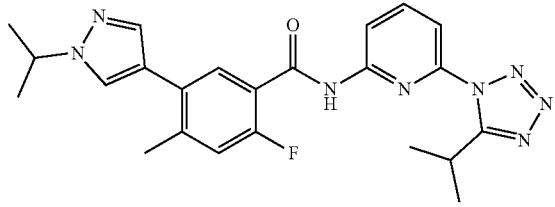 [SMILES: Cc1cc(F)c(C(=O)Nc2cccc(-n3nnnc3C(C)C)n2)cc1-c1cnn(C(C)C)c1]

Example 51 was prepared following the same protocol as described in Example 48. [M+H]⁺ 449; ¹H NMR (400 MHz, Chloroform-d) δ 9.17 (d, J=16.8 Hz, 1H), 8.54 (d, J=8.3 Hz, 1H), 8.15 (d, J=8.3 Hz, 1H), 8.06 (t, J=8.1 Hz, 1H), 7.72 (d, J=8.3 Hz, 1H), 7.69 (s, 1H), 7.61 (s, 1H), 7.14 (d, J=13.1 Hz, 1H), 4.58 (m, 1H), 3.90 (m, 1H), 2.51 (s, 3H), 1.60 (d, J=6.7 Hz, 6H), 1.53 (d, J=6.9 Hz, 6H).

Example 52

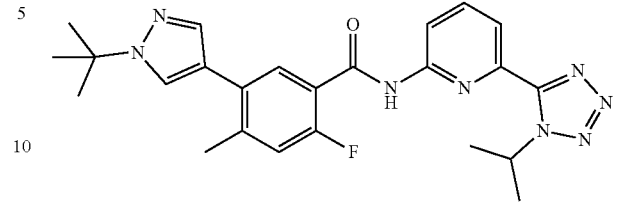

Example 52 was prepared following the same protocol as described in Example 46. [M+H]⁺ 463; 1H NMR (400 MHz, Chloroform-d) δ 9.20 (d, J=16.7 Hz, 1H), 8.56 (dd, J=8.3, 0.9 Hz, 1H), 8.16 (d, J=8.4 Hz, 1H), 8.10 (d, J=8.0 Hz, 1H), 8.00 (t, J=8.0 Hz, 1H), 7.73-7.67 (m, 2H), 7.14 (d, J=13.2 Hz, 1H), 5.77 (m, 1H), 2.52 (s, 3H), 1.75 (d, J=6.7 Hz, 6H), 1.68 (s, 9H).

Example 53

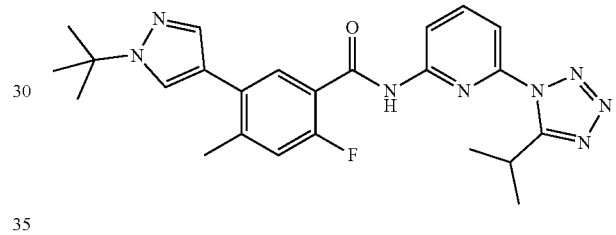

Example 53 was prepared following the same protocol as described in Example 48. [M+H]⁺ 463; ¹H NMR (400 MHz, Chloroform-d) δ 9.17 (d, J=16.8 Hz, 1H), 8.55 (d, J=8.3 Hz, 1H), 8.15 (d, J=8.3 Hz, 1H), 8.06 (t, J=8.1 Hz, 1H), 7.74-7.69 (m, 3H), 7.14 (d, J=13.1 Hz, 1H), 3.91 (m, 1H), 2.51 (s, 3H), 1.68 (s, 9H), 1.53 (d, J=6.9 Hz, 6H).

Example 54

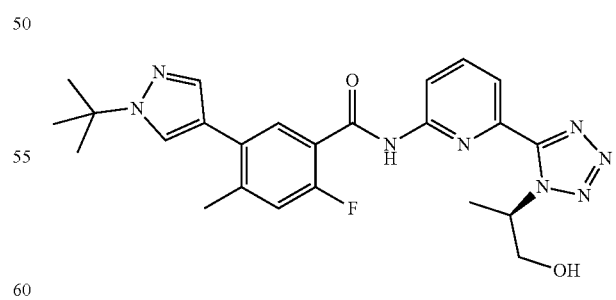

Example 54 was prepared following the same protocol as described in Example 47. [M+H]⁺ 479; ¹H NMR (400 MHz, Chloroform-d) δ 9.20 (d, J=16.8 Hz, 1H), 8.50 (d, J=8.3 Hz, 1H), 8.16-8.11 (m, 2H), 8.02 (t, J=8.0 Hz, 1H), 7.71-7.69 (m, 2H), 7.14 (d, J=13.2 Hz, 1H), 5.76 (m, 1H), 4.24-4.13 (m, 2H), 2.52 (s, 3H), 1.73 (d, J=6.9 Hz, 3H), 1.66 (s, 9H).

Example 55

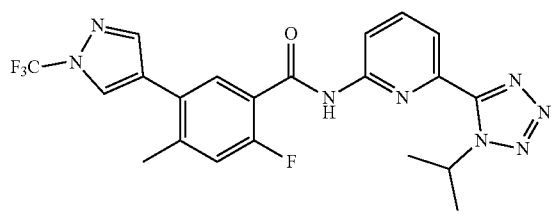 [SMILES: Cc1cc(F)c(C(=O)Nc2cccc(-c3nnnn3C(C)C)n2)cc1-c1cnn(C(F)(F)F)c1]

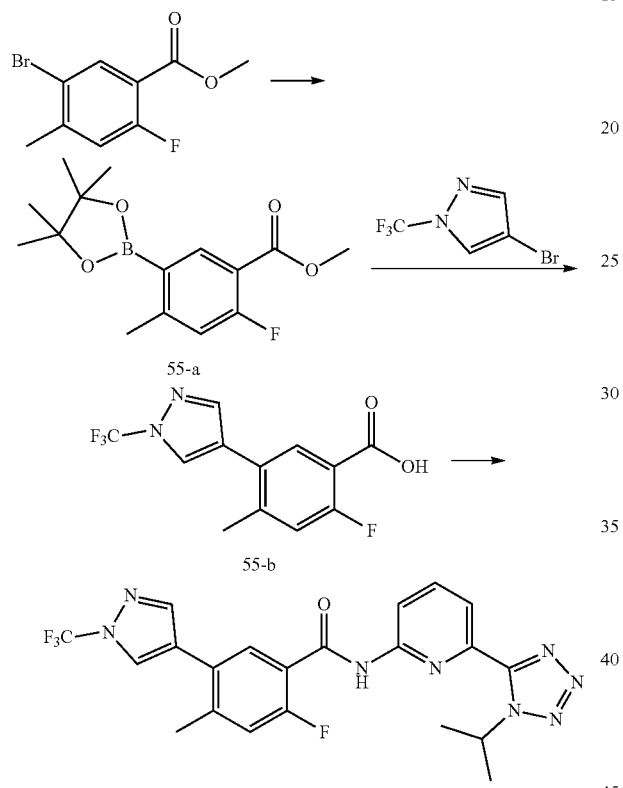

Example 55

Step 55-1

A mixture of methyl 5-bromo-2-fluoro-4-methylbenzoate (1.7 g), 4,4,4',4',5,5,5',5'-octamethyl-2,2'-bi (1,3,2-dioxaborolane) (2.3 g, 7.7 mmol), Pd(dppf)Cl$_2$ CH$_2$Cl$_2$ (24 mg, 0.03 mmol), and KOAc (1.6 g, 19.2 mmol) in dioxane (20 mL) was stirred at 85° C. overnight. Solvent was removed in vacuo. The residue was dissolved in EtOAc, washed with saturated NaCl, dried with Na$_2$SO$_4$, and concentrated in vacuo. Purification of the residue on silica gel column with PE/EtOAc (10:1 to 5:1) provided 1.5 g of compound 55-a (79.3%, 2 steps) as an off-white solid.

Step 55-2

A mixture of compound 55-a (300 mg, 1.0 mmol), 4-bromo-1-(trifluoromethyl)-1H-pyrazole (258 mg, 1.2 mmol), Pd(PPh$_3$)$_4$ (115 mg, 0.10 mmol) and K$_2$CO$_3$ (414 mg, 3.0 mmol) in DME (8 mL) and H$_2$O (2 mL) was stirred at 100° C. under nitrogen atmosphere for 1 h. The reaction mixture was cooled to room temperature and acidified to pH 3~4 with conc.HCl. Solvent was removed in vacuo and the residue was purified by reverse phase flash chromatography with 0-60% CH$_3$CN in water to afford compound 55-b (170 mg, 57.8%) as a light brown solid.

Step 55-3

Example 55 was prepared from compound 55-b following the same protocol as described in Step 46-2. [M+H]$^+$ 475; $^1$H NMR (400 MHz, Chloroform-d) δ 9.18 (d, J=16.5 Hz, 1H), 8.55 (d, J=8.3 Hz, 1H), 8.18 (d, J=8.1 Hz, 1H), 8.12 (d, J=7.6 Hz, 1H), 8.02 (t, J=8.0 Hz, 1H), 7.80-7.97 (m, 2H), 5.75 (m, 1H), 2.50 (s, 3H), 1.75 (d, J=6.6 Hz, 6H).

Example 56

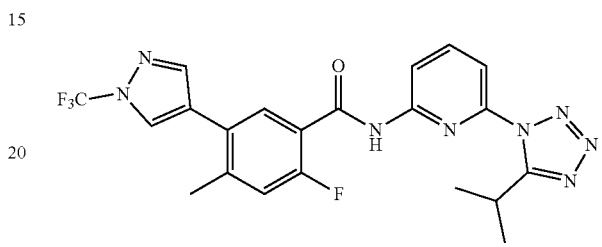

Example 56 was prepared from compound 55-b and compound 17-a following the same protocol as described in Step 46-2. [M+H]$^+$ 475; $^1$H NMR (400 MHz, Chloroform-d) δ 9.15 (d, J=16.6 Hz, 1H), 8.54 (d, J=8.3 Hz, 1H), 8.17 (d, J=8.1 Hz, 1H), 8.07 (t, J=8.1 Hz, 1H), 7.97-7.94 (m, 2H), 7.74 (d, J=7.9 Hz, 1H), 7.21 (d, J=13.0 Hz, 1H), 3.89 (m, 1H), 2.50 (s, 3H), 1.54 (d, J=6.9 Hz, 6H).

Example 57

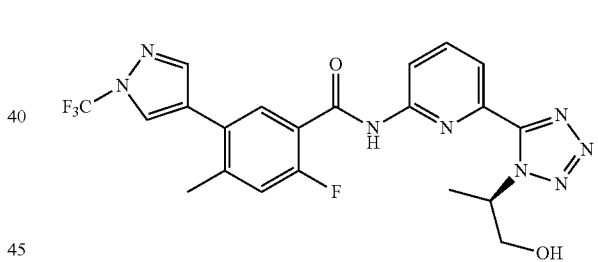

Example 57 was prepared from compound 55-b following the same protocol as described in Step 47-1. [M+1]$^+$491; $^1$H NMR (400 MHz, Chloroform-d) δ 9.18 (d, J=16.3 Hz, 1H), 8.48 (d, J=8.3 Hz, 1H), 8.17-8.11 (m, 2H), 8.03 (t, J=8.0 Hz, 1H), 7.97-7.94 (m, 2H), 7.20 (d, J=12.9 Hz, 1H), 5.74 (m, 1H), 4.18 (m, 2H), 2.50 (s, 3H), 1.73 (d, J=6.8 Hz, 3H).

Example 58

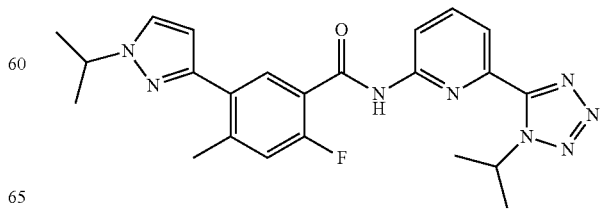

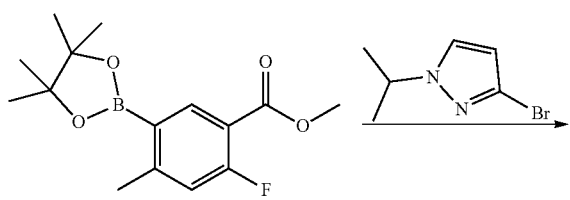

55-a

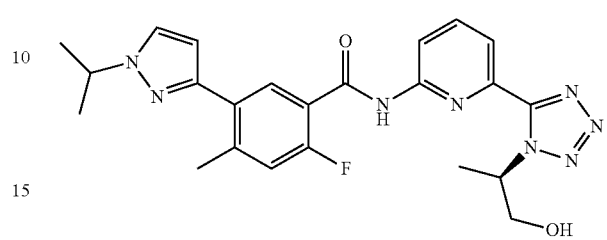

58-a

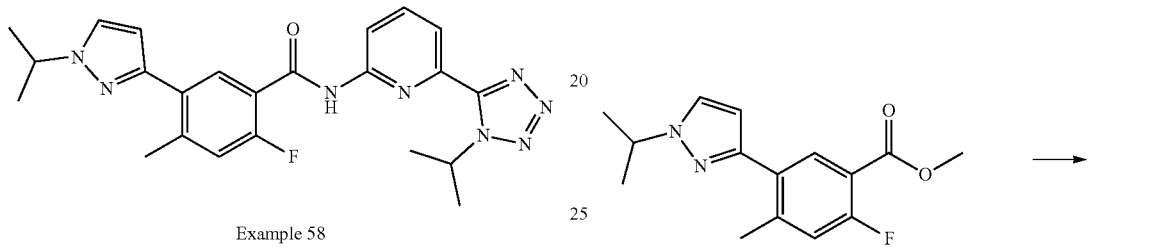

Example 58

Step 58-1

A mixture of compound 55-a (300 mg, 1.02 mmol), 3-bromo-1-(propan-2-yl)-1H-pyrazole (267.6 mg, 1.42 mmol), Pd(PPh$_3$)$_4$ (118 mg, 0.10 mmol), K$_2$CO$_3$ (422 mg, 3.00 mmol) in 1,4-dioxane (10 mL) was stirred at 100° C. overnight. Solvent was removed in vacuo and the residue was purified by silica gel column chromatography eluting with 0-50% EtOAc/PE to give 210 mg (74.6%) of compound 58-a as a white solid.

Step 58-2

Example 58 was prepared from compound 58-a following a similar protocol as described in Step 18-2. [M+H]$^+$ 449. $^1$H NMR (400 MHz, Chloroform-d) δ 9.17 (d, J=16.2 Hz, 1H), 8.57 (d, J=8.3 Hz, 1H), 8.39 (d, J=8.4 Hz, 1H), 8.10 (d, J=7.5 Hz, 1H), 7.99 (t, J=8.0 Hz, 1H), 7.51 (d, J=2.3 Hz, 1H), 7.13 (d, J=13.2 Hz, 1H), 6.46 (d, J=2.3 Hz, 1H), 5.78 (m, 1H), 4.57 (m, 1H), 2.60 (s, 3H), 1.75 (d, J=6.7 Hz, 6H), 1.59 (d, J=6.7 Hz, 6H).

Example 59

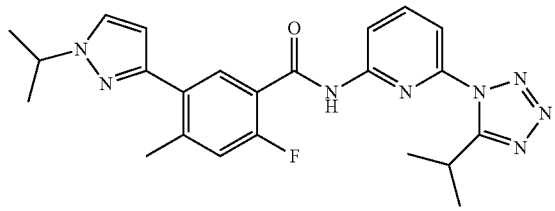 [SMILES: Cc1cc(F)c(C(=O)Nc2cccc(-n3nnnc3C(C)C)n2)cc1-c1ccn(C(C)C)n1]

Example 59 was prepared from compound 58-a and compound 17-a following a similar protocol as described in Step 18-2. [M+H]+ 449. $^1$H NMR (400 MHz, Chloroform-d) δ 9.14 (d, J=16.5 Hz, 1H), 8.56 (d, J=8.3 Hz, 1H), 8.38 (d, J=8.4 Hz, 1H), 8.05 (t, J=8.0 Hz, 1H), 7.72 (d, J=7.8 Hz, 1H), 7.51 (d, J=2.3 Hz, 1H), 7.14 (d, J=13.2 Hz, 1H), 6.46 (d, J=2.3 Hz, 1H), 4.58 (m, 1H), 3.92 (m, 1H), 2.60 (s, 3H), 1.59 (d, J=6.8 Hz, 6H), 1.54 (d, J=6.8 Hz, 6H).

Example 60

Example 60

Step 60-1

To a solution of compound 58-a (60 mg, 0.217 mmol) in MeOH (6 mL) and H$_2$O (2 mL) was added LiOH (52 mg, 2.17 mmol). The resulting solution was stirred at room temperature for 2 h. Solvent was removed in vacuo and the residue was purified by flash-Prep-HPLC with 0-100% MeCN/H$_2$O to afford 40 mg (70%) of compound 60-a as a white solid.

Step 60-2

Example 60 was prepared from compound 60-a following the same protocol as described in Step 47-1. [M+H]$^+$ 465. $^1$H NMR (400 MHz, Chloroform-d) δ 9.19 (d, J=16.1 Hz, 1H), 8.50 (d, J=8.3 Hz, 1H), 8.37 (d, J=8.4 Hz, 1H), 8.12 (d, J=7.6 Hz, 1H), 8.01 (t, J=8.0 Hz, 1H), 7.51 (d, J=2.2 Hz, 1H), 7.13 (d, J=13.2 Hz, 1H), 6.46 (d, J=2.3 Hz, 1H), 5.77 (m, 1H), 4.58 (m, 1H), 4.25-4.10 (m, 2H), 2.99 (s, 1H), 2.60 (s, 3H), 1.73 (d, J=7.0 Hz, 3H), 1.59 (d, J=6.7 Hz, 6H).

Example 61

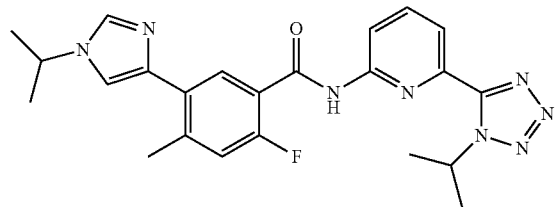 [SMILES: Cc1cc(F)c(C(=O)Nc2cccc(-c3nnnn3C(C)C)n2)cc1-c1cn(C(C)C)cn1]

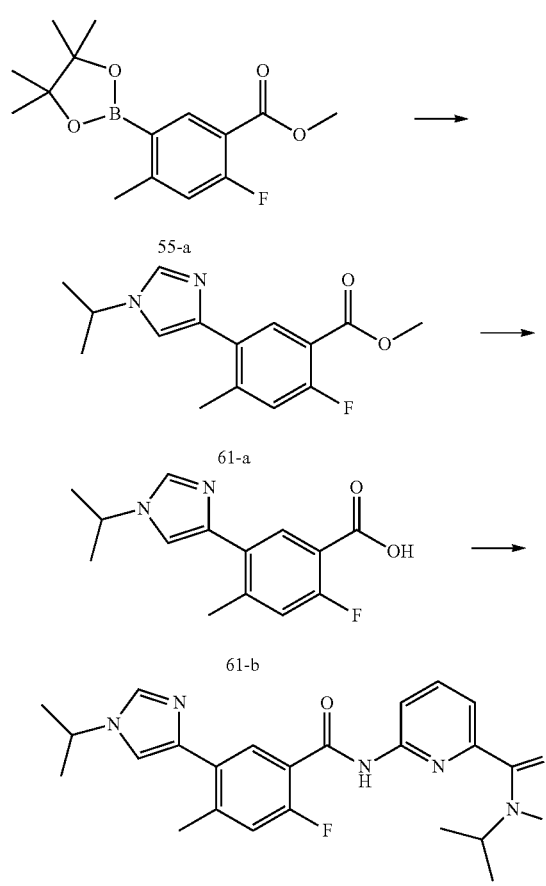

Example 61

Step 61-1
A mixture of compound 55-a (300 mg, 1.02 mmol), 4-bromo-1-(propan-2-yl)-1H-imidazole (230 mg, 1.22 mmol), Pd(PPh$_3$)$_4$ (117.7 mg, 0.10 mmol), and K$_2$CO$_3$ (422 mg, 3.06 mmol) in 1,4-dioxane (2 mL) was stirred at 100° C. overnight. Solvent was removed in vacuo and the residue was purified on a silica gel column with 30% EtOAc in PE to afford 130 mg (46%) of compound 61-a as a yellow solid.

Step 61-2
Compound 61-a (130 mg, 0.47 mmol) was added into a mixture of sodium hydroxide (94 mg, 2.35 mmol) in methanol (6 mL) and H$_2$O (2 mL). The resulting solution was stirred at room temperature for 2 h. Solvent was removed in vacuo and the crude product was purified by Flash-Prep-HPLC with the 0-100% MeCN/H$_2$O to afford 100 mg (81%) of compound 61-b as a white solid.

Step 61-3
Example 61 was prepared from compound 61-b following the same protocol as described in Step 46-2. [M+H]$^+$ 449; $^1$H NMR (400 MHz, Chloroform-d) δ 9.19 (d, J=15.6 Hz, 1H), 8.57 (d, J=8.3 Hz, 1H), 8.42 (d, J=8.4 Hz, 1H), 8.10 (d, J=7.6 Hz, 1H), 7.99 (t, J=8.0 Hz, 1H), 7.67 (s, 1H), 7.18 (s, 1H), 7.15 (d, J=4.8 Hz, 1H), 5.80 (m, 1H), 4.43 (m, 1H), 2.63 (s, 3H), 1.75 (d, J=6.6 Hz, 6H), 1.59 (d, J=6.7 Hz, 6H).

Example 62

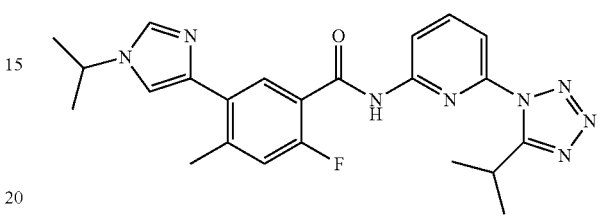

Example 62 was prepared from compound 61-b and compound 17-a following a similar protocol as described in Step 46-2. [M+H]$^+$ 449; $^1$H NMR (400 MHz, Chloroform-d) δ 9.15 (d, J=15.9 Hz, 1H), 8.55 (d, J=8.3 Hz, 1H), 8.42 (d, J=8.4 Hz, 1H), 8.04 (t, J=8.1 Hz, 1H), 7.71 (d, J=7.6 Hz, 1H), 7.67 (s, 1H), 7.28 (s, 1H), 7.12 (d, J=13.2 Hz, 1H), 4.43 (m, 1H), 3.92 (m, 1H), 2.62 (s, 3H), 1.59 (d, J=6.8 Hz, 2H), 1.53 (d, J=6.8 Hz, 2H).

Example 63

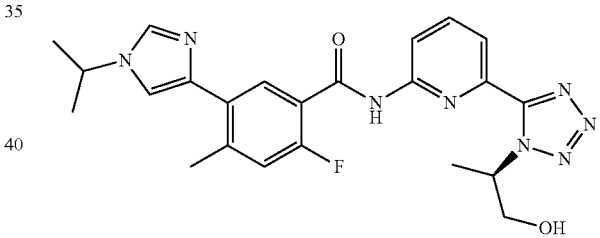

Example 63 was prepared from compound 61-b following the same protocol as described in Step 47-1. [M+H]$^+$ 465; $^1$H NMR (400 MHz, Chloroform-d) δ 9.36 (d, J=13.4 Hz, 1H), 8.47 (d, J=8.3 Hz, 1H), 8.38 (d, J=8.2 Hz, 1H), 8.10 (d, J=7.6 Hz, 1H), 7.99 (t, J=7.9 Hz, 1H), 7.69 (s, 1H), 7.17 (s, 1H), 7.10 (d, J=12.8 Hz, 1H), 5.83 (m, 1H), 4.44 (m, 1H), 4.16 (m, 2H), 2.59 (s, 3H), 1.72 (d, J=6.8 Hz, 3H), 1.60 (d, J=6.7 Hz, 6H).

Example 64

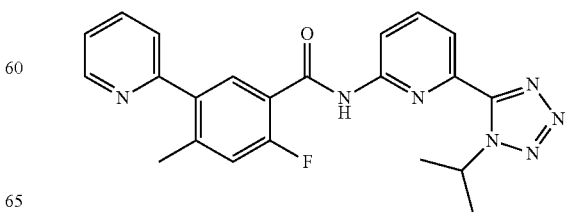

71

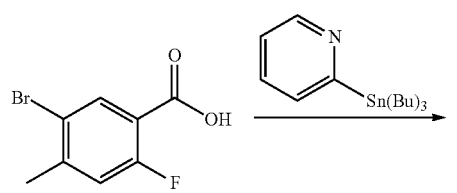

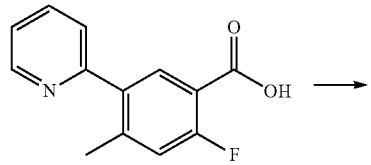

64-a

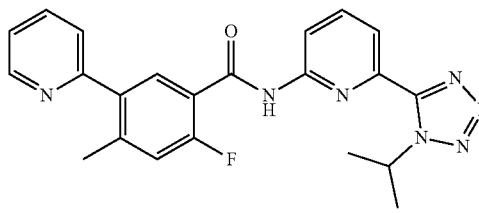

Example 64

Step 64-1

In a sealed vial a mixture of 5-bromo-2-fluoro-4-methylbenzoic acid (100 mg, 0.43 mmol), 2-(tributylstannyl) pyridine (190 mg, 0.52 mmol), Pd(PPh$_3$)$_4$ (49 mg, 0.04 mmol) in DMF (2 mL) was heated in microwave at 160° C. for 1 hour. Solvent was removed in vacuo, and the residue was purified by Flash-Prep-HPLC with 0-100% MeCN/H$_2$O to afford 40 mg (37%) of compound 64-a as a yellow solid.

Step 64-2

Example 64 was prepared from compound 64-a following the same protocol as described in Step 46-2. [M+H]$^+$ 418; $^1$H NMR (400 MHz, Chloroform-d) δ 9.19 (d, J=16.1 Hz, 1H), 8.74 (d, J=4.4 Hz, 1H), 8.55 (d, J=8.3 Hz, 1H), 8.25 (d, J=8.3 Hz, 1H), 8.11 (d, J=7.5 Hz, 1H), 8.00 (t, J=8.0 Hz, 1H), 7.84 (td, J=7.7, 1.8 Hz, 1H), 7.48 (d, J=7.8 Hz, 1H), 7.34 (dd, J=7.5, 5.0 Hz, 1H), 7.19 (d, J=13.1 Hz, 1H), 5.78 (m, 1H), 2.49 (s, 3H), 1.75 (d, J=6.7 Hz, 6H).

Example 65

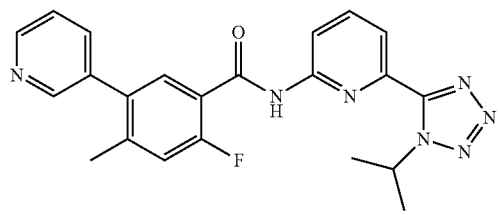 [SMILES: Cc1cc(F)c(C(=O)Nc2cccc(-c3nnnn3C(C)C)n2)cc1-c1cccnc1]

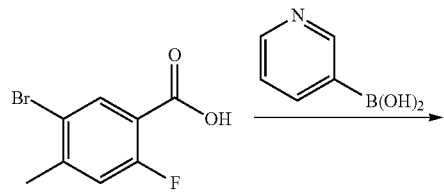

72

-continued

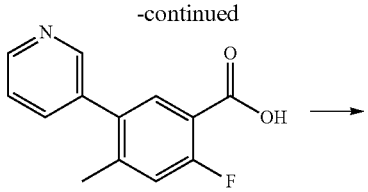

65-a

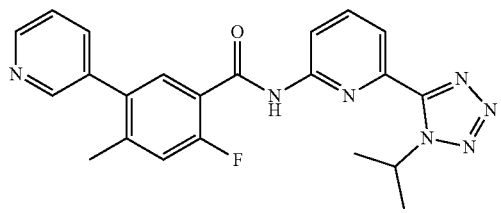

Example 65

Step 65-1

A mixture of 5-bromo-2-fluoro-4-methylbenzoic acid (100 mg, 0.40 mmol), (pyridin-3-yl)boronic acid (64 mg, 0.52 mmol), Pd(PPh$_3$)$_4$ (99 mg, 0.08 mmol), and K$_2$CO$_3$ (179 mg, 1.3 mmol) in ethylene glycol dimethyl ether (4 mL) and H$_2$O (2 mL) was stirred at 100° C. overnight.

Solvent was removed in vacuo, and the residue was purified by Flash-Prep-HPLC with 0-70% MeCN/H$_2$O to afford 40 mg (37%) of compound 65-a as a yellow solid.

Step 65-2

Example 65 was prepared from compound 65-a following the same protocol as described in Step 46-2. [M+H]$^+$ 418; $^1$H NMR (400 MHz, Chloroform-d) δ 9.19 (d, J=16.2 Hz, 1H), 8.69-8.64 (m, 2H), 8.55 (d, J=8.3 Hz, 1H), 8.12-8.09 (m, 2H), 8.01 (t, J=8.0 Hz, 1H), 7.71 (m, 1H), 7.45 (dd, J=7.5, 5.1 Hz, 1H), 7.22 (d, J=13.0 Hz, 1H), 5.75 (m, 1H), 3.51 (s, 1H), 2.39 (s, 3H), 1.75 (d, J=6.7 Hz, 6H).

Example 66

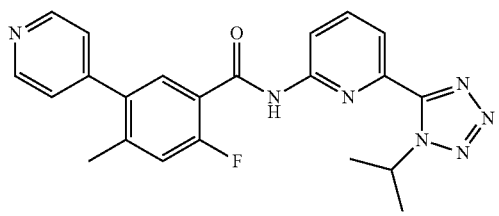 [SMILES: Cc1cc(F)c(C(=O)Nc2cccc(-c3nnnn3C(C)C)n2)cc1-c1ccncc1]

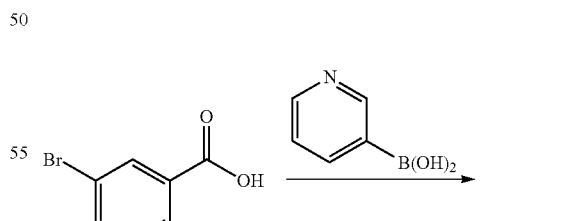

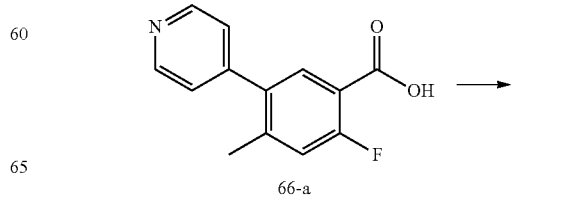

66-a

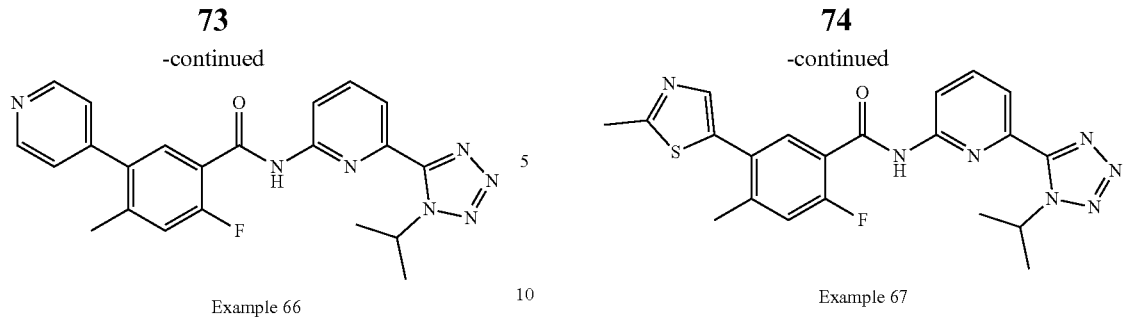

Example 66            Example 67

Step 66-1

A mixture of 5-bromo-2-fluoro-4-methylbenzoic acid (100 mg, 0.43 mmol), (pyridin-4-yl)boronic acid (64 mg, 0.52 mmol), Pd(PPh$_3$)$_4$ (99 mg, 0.08 mmol), and K$_2$CO$_3$ (179 mg, 1.3 mmol) in ethylene glycol dimethyl ether (4 mL), and H$_2$O (2 mL) was stirred at 100° C. overnight. Solvent was removed in vacuo and the crude product was purified by Flash-Prep-HPLC with 0-100% MeCN/H$_2$O to afford 70 mg (75%) of compound 66-a as a white solid.

Step 66-2

Example 66 was prepared from compound 66-a following the same protocol as described in Step 46-2. [M+H]$^+$ 418; $^1$H NMR (400 MHz, Chloroform-d) δ 9.18 (d, J=16.2 Hz, 1H), 8.75 (s, 2H), 8.55 (d, J=8.3 Hz, 1H), 8.14-8.09 (m, 2H), 8.01 (t, J=7.9 Hz, 1H), 7.35 (d, J=5.0 Hz, 2H), 7.23 (d, J=13.0 Hz, 1H), 5.75 (m, 1H), 2.40 (s, 3H), 1.75 (d, J=6.7 Hz, 6H).

Step 67-1

A mixture of 5-bromo-2-fluoro-4-methylbenzoic acid (100 mg, 0.43 mmol), 2-methyl-5-(4,4,5,5-tetra methyl-1,3,2-dioxaborolan-2-yl)-1,3-thiazole (193.2 mg, 0.86 mmol), Pd(PPh$_3$)$_4$ (99.2 mg, 0.09 mmol), and K$_2$CO$_3$ (177.9 mg, 1.29 mmol) in ethylene glycol dimethyl ether (5 mL) and H$_2$O (1 mL) was stirred at 100° C. under nitrogen atmosphere overnight. The mixture was allowed to cool down to room temperature, and acidified to pH 3~4 with 1N HCl. Solvent was removed in vacuo and the residue was purified by reverse phase chromatography with 0-38% MeCN/H$_2$O=38:62) to afford compound 67-a (40 mg, 37.10%) as a yellow solid.

Step 67-2

Example 67 was prepared from compound 67-a following the same protocol as described in Step 46-2. [M+H]$^+$ 438; $^1$H NMR (400 MHz, Chloroform-d) δ 9.15 (d, J=16.1 Hz, 1H), 8.55 (d, J=8.3 Hz, 1H), 8.20 (d, J=8.1 Hz, 1H), 8.11 (d, J=7.6 Hz, 1H), 8.00 (t, J=7.9 Hz, 1H), 7.63 (s, 1H), 7.18 (d, J=12.9 Hz, 1H), 5.75 (m, 1H), 2.79 (s, 3H), 2.49 (s, 3H), 1.74 (d, J=6.7 Hz, 6H).

Example 67

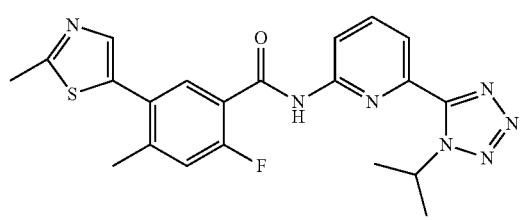 [SMILES: Cc1ncc(-c2cc(C(=O)Nc3cccc(-c4nnnn4C(C)C)n3)c(F)cc2C)s1]

Example 68

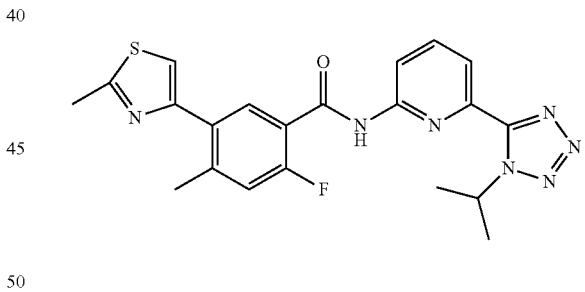

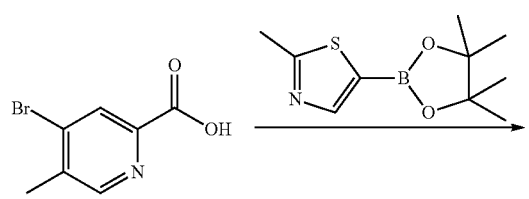

67-a

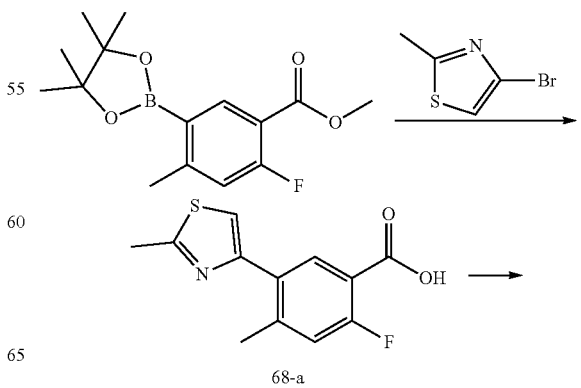

68-a

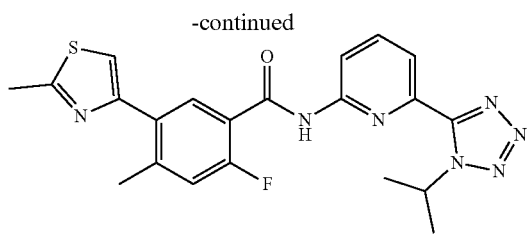

Example 68

Step 68-1

A mixture of methyl 2-fluoro-4-methyl-5-(4,4,5,5-tetramethyl-1,3,2-dioxaborolan-2-yl)benzoate (100 mg, 0.34 mmol), 4-bromo-2-methyl-1,3-thiazole (72 mg, 0.40 mmol), Pd(PPh$_3$)$_4$ (30 mg, 0.03 mmol), K$_2$CO$_3$ (141 mg, 1.02 mmol) in ethylene glycol dimethyl ether (5 mL) and H$_2$O (1 mL) was stirred at 100° C. overnight. Solvent was removed in vacuo, and the residue was purified by Flash-Prep-HPLC with 0-80% MeCN/H$_2$O to afford 55 mg (65%) of compound 68-a as a yellow solid.

Step 68-2

Example 68 was prepared from compound 68-a following the same protocol as described in Step 46-2. [M+H]$^+$ 438; $^1$H NMR (400 MHz, Chloroform-d) δ 9.17 (d, J=16.1 Hz, 1H), 8.56 (d, J=8.3 Hz, 1H), 8.37 (d, J=8.4 Hz, 1H), 8.10 (d, J=7.6 Hz, 1H), 8.00 (t, J=8.0 Hz, 1H), 7.20 (s, 1H), 7.15 (d, J=13.2 Hz, 1H), 5.77 (m, 1H), 2.81 (s, 3H), 2.54 (s, 3H), 1.75 (d, J=6.8 Hz, 6H).

Example 69

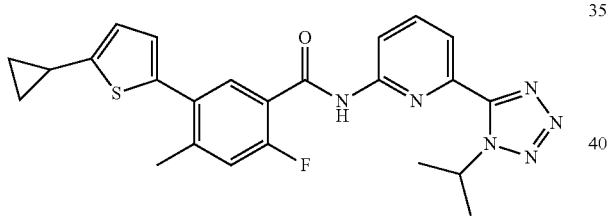

Example 69 was prepared following a similar protocol as described in Example 61. [M+H]$^+$ 463.

$^1$H NMR (400 MHz, Chloroform-d) δ 9.15 (d, J=16.1 Hz, 1H), 8.55 (d, J=8.3 Hz, 1H), 8.20 (d, J=8.2 Hz, 1H), 8.10 (d, J=7.6 Hz, 1H), 7.99 (t, J=8.0 Hz, 1H), 7.13 (d, J=13.1 Hz, 1H), 6.90 (d, J=3.5 Hz, 1H), 6.79 (d, J=3.6 Hz, 1H), 5.77 (m, 1H), 2.52 (s, 3H), 2.13 (m, J=8.7, 5.0 Hz, 1H), 1.74 (d, J=6.7 Hz, 6H), 1.15 (m, 2H), 0.80 (m, 2H).

Example 70

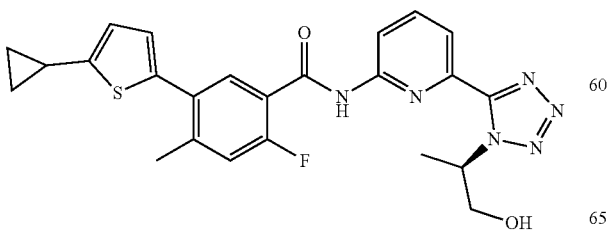

Example 70 was prepared following a similar protocol as described in Example 63. [M+H]$^+$ 479. $^1$H NMR (400 MHz, Chloroform-d) δ 9.13 (d, J=16.3 Hz, 1H), 8.48 (d, J=8.3 Hz, 1H), 8.19 (d, J=8.2 Hz, 1H), 8.12 (d, J=7.6 Hz, 1H), 8.01 (t, J=8.0 Hz, 1H), 7.13 (d, J=13.1 Hz, 1H), 6.90 (d, J=3.6 Hz, 1H), 6.79 (d, J=3.6 Hz, 1H), 5.75 (m, 1H), 4.17 (m, J=11.9, 5.9 Hz, 2H), 2.52 (s, 3H), 2.15 (m, 1H), 1.73 (d, J=6.8 Hz, 3H), 1.05 (m, 2H), 0.80 (m, 2H).

Example 71

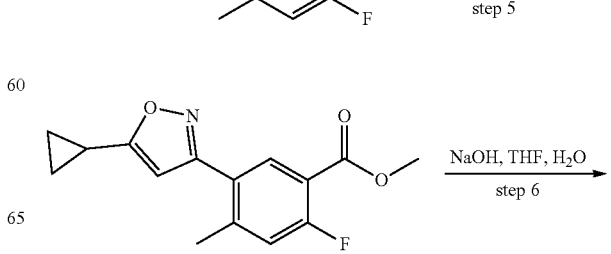

-continued

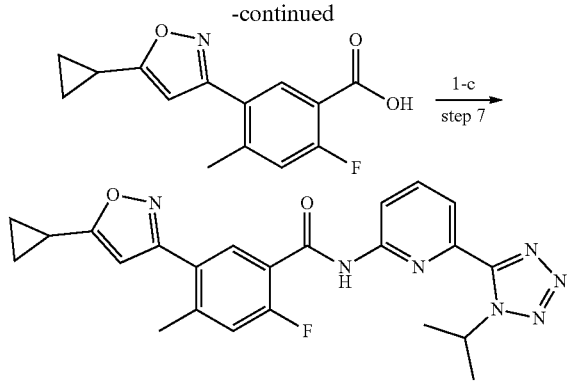

Example 71

Step 71-1

A solution of 5-bromo-4-fluoro-2-methylbenzoic acid (900 mg, 3.9 mmol), methoxy(methyl)amine hydrochloride (573 mg, 5.9 mmol), HATU (2.3 g, 6.0 mmol), and DIPEA (2 g, 15.5 mmol) in DCM (20 mL) was stirred at room temperature overnight. Then the resulting solution was diluted with sat. NaCl and extracted with EtOAc (30 mL×3). The combined organic layers were dried over anhydrous $Na_2SO_4$. After filtration, the filtrate was concentrated under reduced pressure. The residue was purified by silica gel column chromatography with PE/EtOAc (2:1) to give 5-bromo-4-fluoro-N-methoxy-N,2-dimethylbenzamide (900 mg, 84.4%) as a light yellow oil.

Step 71-2

In a 3-necked round-bottom flask a solution of 5-bromo-4-fluoro-N-methoxy-N,2-dimethylbenzamide (900 mg, 3.3 mmol) in THF was cooled to −30° C. under nitrogen atmosphere. $CH_3MgCl$ in THF (3M) (14.6 mL, 43.8 mmol) was added dropwise over 10 min while maintaining the temperature below 0° C. The reaction solution was stirred at 0° C. for 0.5 h, quenched with sat. $NH_4C_1$ at 0° C., and extracted with EtOAc (30 mL×3). The combined organic layers were dried over anhydrous $Na_2SO_4$. After filtration, the filtrate was concentrated under reduced pressure. The residue was purified by silica gel column chromatography with PE/EtOAc (2:1) to give 1-(5-bromo-4-fluoro-2-methylphenyl)ethan-1-one (600 mg, 79.6%) as a light yellow solid.

Step 71-3

A mixture of 1-(5-bromo-4-fluoro-2-methylphenyl)ethan-1-one (600 mg, 2.6 mmol), 1-cyclopropane-carbonyl-1H-1,2,3-benzotriazole (885 mg, 4.8 mmol), magnesium bromide ethyl etherate (4.9 g, 19.2 mmol) and DIPEA (1.2 g, 9.3 mmol) in DCM (mL) was stirred at room temperature for 3 days. The resulting mixture was diluted with sat. NaCl (10 mL) and then extracted with EtOAc (10 mL×3). The combined organic layers were dried over anhydrous $Na_2SO_4$. After filtration, the filtrate was concentrated under reduced pressure. The residue was purified by reverse flash chromatography with the following conditions (column, C18 silica gel; mobile phase, ACN in FA (0.1%) water, 0% to 100% gradient in 25 min; detector, UV 254 nm) to give 1-(5-bromo-4-fluoro-2-methylphenyl)-3-cyclopropyl propane-1,3-dione (400 mg, 51.4%) as a yellow oil.

Step 71-4

A solution of 1-(5-bromo-4-fluoro-2-methylphenyl)-3-cyclopropylpropane-1,3-dione (400 mg, 1.3 mmol) and hydroxylamine hydrochloride (318 mg, 4.6 mmol) in MeOH (10 mL) was stirred at 45° C. overnight. The resulting solution was diluted with sat. NaCl (20 mL) and extracted with EtOAc (20 mL×3). The combined organic layers were dried over anhydrous $Na_2SO_4$. After filtration, the filtrate was concentrated under reduced pressure. The residue was purified by reverse flash chromatography with the following conditions (column, C18 silica gel; mobile phase, ACN in water, 0 to 100% gradient in 25 min; detector, UV 254 nm) to give 3-(5-bromo-4-fluoro-2-methylphenyl)-5-cyclopropyl-1,2-oxazole (170 mg, 42.9%) as a yellow oil.

Step 71-5

A mixture of 3-(5-bromo-4-fluoro-2-methylphenyl)-5-cyclopropyl-1,2-oxazole (170 mg, 0.5 mmol), $Pd(dppf)Cl_2$ $CH_2Cl_2$ (258 mg, 0.3 mmol), and TEA (478 mg, 4.8 mmol) in DMF/MeOH (4/1 mL) was stirred at 75° C. under CO atmosphere overnight. The resulting mixture was diluted with sat. NaCl and then extracted with EtOAc (10 mL×3). The combined organic layers were dried over anhydrous $Na_2SO_4$. After filtration, the filtrate was concentrated under reduced pressure. The residue was purified by reverse flash chromatography with the following conditions (column, C18 silica gel; mobile phase, ACN in water, 0 to 80% gradient in 20 min; detector, UV 254 nm) to give methyl 5-(5-cyclopropyl-1,2-oxazol-3-yl)-2-fluoro-4-methylbenzoate (80 mg, 50.6%) as a yellow oil.

Step 71-6

A mixture of methyl 5-(5-cyclopropyl-1,2-oxazol-3-yl)-2-fluoro-4-methylbenzoate (80 mg, 0.3 mmol) and LiOH (24 mg, 0.9 mmol) in $THF/H_2O$ (1/0.3 mL) was stirred at room temperature for 2 hours. Then the mixture was acidified to pH 4~5 with 1M HCl (aq.) and extracted with EtOAc (10 mL×3). The combined organic layers were dried over anhydrous $Na_2SO_4$ and concentrated under reduced pressure to give 5-(5-cyclopropyl-1,2-oxazol-3-yl)-2-fluoro-4-methylbenzoic acid (50 mg, 65.8%) as a yellow oil.

Step 71-7

To a stirred solution of 5-(5-cyclopropyl-1,2-oxazol-3-yl)-2-fluoro-4-methylbenzoic acid (50 mg, 0.2 mmol) in DCM (1 mL) was added (1-chloro-2-methylprop-1-en-1-yl)dimethylamine (33 mg, 0.2 mmol) dropwise at room temperature under nitrogen atmosphere. After stirring for 1 hour, a solution of pyridine (48 mg, 0.6 mmol) and 6-(1-isopropyl-1H-tetrazol-5-yl)pyridin-2-amine (86 mg, 0.4 mmol) in DCM (1 mL) was added. After stirring for another 1 hour, the solution was quenched with water (10 mL) and then extracted with EtOAc (10 mL×3). The combined organic layers were dried over anhydrous $Na_2SO_4$, filtered and concentrated under reduced pressure. The residue was purified by reverse flash chromatography with the following conditions (column, C18 silica gel; mobile phase, ACN in water, 0% to 90% gradient in 20 min; detector, UV 254 nm) to give 14 mg of Example 71 as an off-white solid. MS m/z: [M+H]$^+$=448.20, t=1.928 min. $^1$H NMR (400 MHz, Chloroform-d) δ 9.13 (d, J=15.8 Hz, 1H), 8.55 (d, J=8.3 Hz, 1H), 8.47 (d, J=8.0 Hz, 1H), 8.12 (d, J=7.6 Hz, 1H), 8.02 (t, J=8.0 Hz, 1H), 7.20 (d, J=12.9 Hz, 1H), 6.20 (s, 1H), 5.75 (m, 1H), 2.62 (s, 3H), 2.10 (m, 1H), 1.74 (d, J=6.7 Hz, 6H), 1.18-1.08 (m, 2H), 0.97-0.89 (m, 2H).

Example 72-A and 72-B
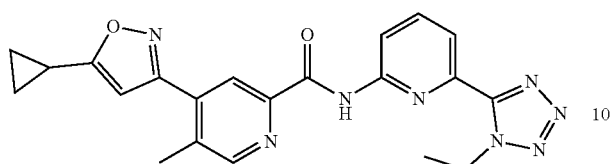
Example 72-A
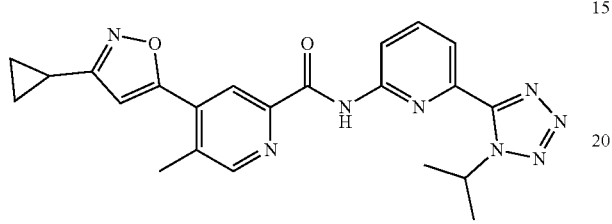
Example 72-B
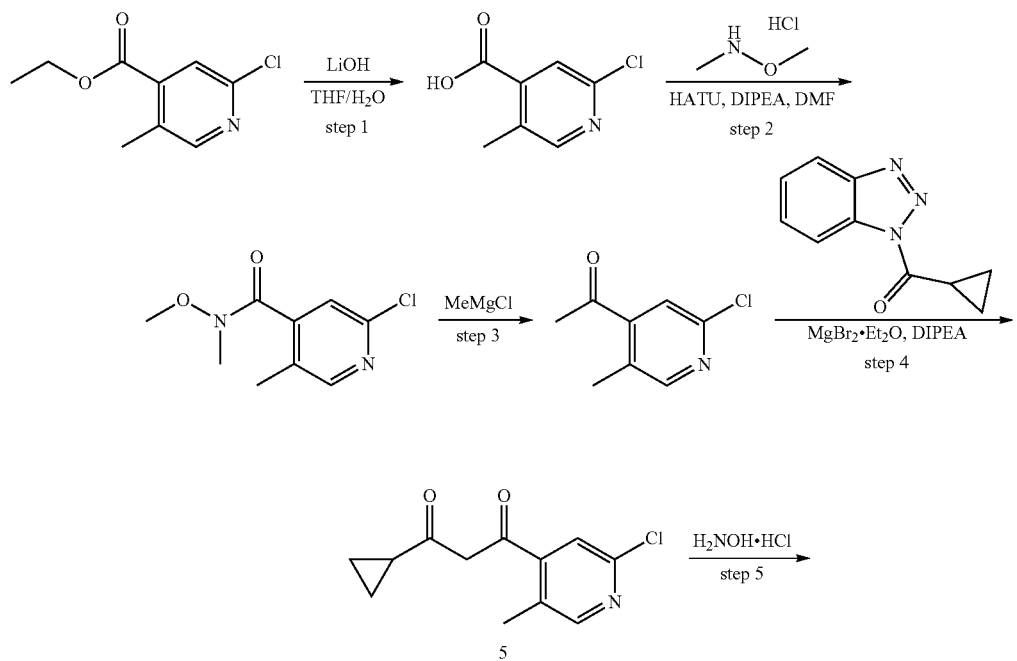
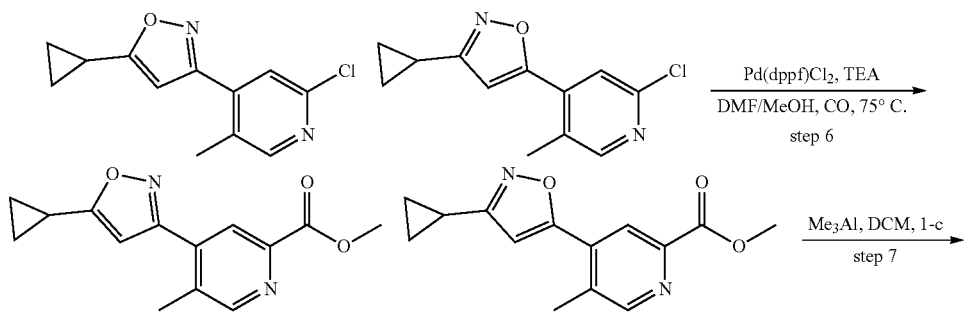

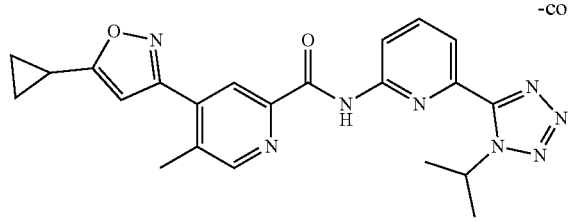

Example 72-A

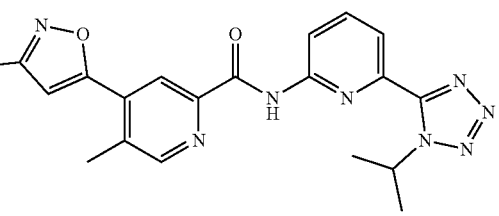

Example 72-B

Step 72-1

A mixture of ethyl 2-chloro-5-fluoropyridine-4-carboxylate (1.0 g, 4.91 mmol) and LiOH (1.5 g, 6.26 mmol) in THF/H$_2$O (20/5 mL) was stirred at room temperature for 2 hours. The mixture was acidified with HCl (aq.), and extracted with EtOAc (30 mL×3). The combined organic layers were dried over anhydrous Na$_2$SO$_4$.

After filtration, the filtrate was concentrated under reduced pressure to give 760 mg (88.4%) of 2-chloro-5-methylisonicotinic acid as an off-white solid.

Step 72-2

2-Chloro-N-methoxy-N,5-dimethylisonicotinamide was prepared as described in Step 71-1. 700 mg (73.6%) was obtained as an off-white solid.

Step 72-3

1-(2-Chloro-5-methylpyridin-4-yl)ethan-1-one was prepared as described in Step 71-2. 400 mg (84.4%) was obtained as a light yellow oil.

Step 72-4

1-(2-Chloro-5-methylpyridin-4-yl)-3-cyclopropylpropane-1,3-dione was prepared as described in Step 71-3. 220 mg (41.3%) was obtained as a white solid.

Step 72-5

A mixture of 3-(2-Chloro-5-methylpyridin-4-yl)-5-cyclopropylisoxazole and 5-(2-chloro-5-methylpyridin-4-yl)-3-cyclopropylisoxazole (190 mg, 96.2%) were prepared as described in Step 71-4 as a light yellow solid.

Step 72-6

Methyl 4-(5-cyclopropylisoxazol-3-yl)-5-methylpicolinate (20 mg) and methyl 4-(3-cyclopropylisoxazol-5-yl)-5-methylpicolinate (18 mg) were prepared as described in Step 71-5 as a light yellow solid.

Step 72-7

Example 72-A was prepared as described in Step 29-1. 10 mg was obtained as a dark yellow solid. MS m/z: [M+H]$^+$= 431.20; $^1$H NMR (400 MHz, Chloroform-d) δ 10.50 (s, 1H), 8.66 (s, 1H), 8.61 (d, J=8.3 Hz, 1H), 8.42 (s, 1H), 8.11 (d, J=7.5 Hz, 1H), 8.01 (t, J=8.0 Hz, 1H), 6.33 (s, 1H), 5.88 (m, 1H), 2.68 (s, 3H), 2.18 (m, 1H), 1.76 (d, J=6.7 Hz, 6H), 1.20-1.17 (m, 2H), 1.13-1.10 (m, 2H).

Example 72-B was prepared as described in Sep 29-1. 4.8 mg was obtained as a off-white solid. MS m/z: [M+H]$^+$= 431.20. $^1$H NMR (400 MHz, Chloroform-d) δ 10.46 (s, 1H), 8.68-8.59 (m, 2H), 8.57 (s, 1H), 8.11 (d, J=7.5 Hz, 1H), 8.02 (t, J=8.0 Hz, 1H), 6.46 (s, 1H), 5.86 (m, 1H), 2.69 (s, 3H), 2.12 (m, 1H), 1.76 (d, J=6.7 Hz, 6H), 1.21-1.13 (m, 2H), 1.01-0.92 (m, 2H).

Example 73

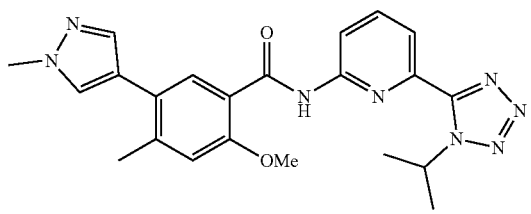 [SMILES: COc1cc(C)c(-c2cnn(C)c2)cc1C(=O)Nc1cccc(-c2nnnn2C(C)C)n1]

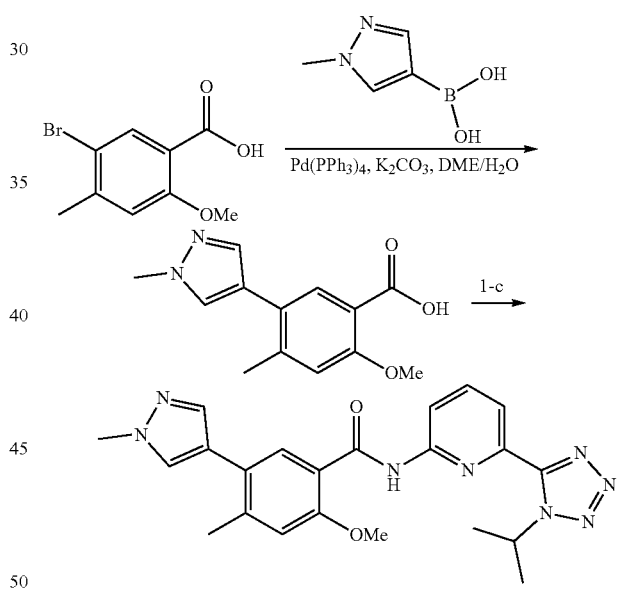

Example 73

Step 73-1

A mixture of 1-methylpyrazol-4-ylboronic acid (113 mg, 0.89 mmol), 5-bromo-2-methoxy-4-methyl benzoic acid (200 mg, 0.82 mmol), Pd(PPh$_3$)$_4$ (94 mg, 0.08 mmol), and K$_2$CO$_3$ (451 mg, 3.26 mmol) in DME/H$_2$O (5/1 mL) was stirred at 100° C. under nitrogen atmosphere overnight. The solution was diluted with H$_2$O (10 mL), acidified to pH 4~5 with 1 M HCl (aq.), and extracted with EtOAc (10 mL×3). The combined organic layers were dried over anhydrous Na$_2$SO$_4$ and concentrated. The residue was purified by silica gel column chromatography with DCM/MeOH (30:1) to give 2-methoxy-4-methyl-5-(1-methyl-1H-pyrazol-4-yl) benzoic acid (140 mg, Y=69.9%) as a yellow oil.

Step 73-2.

Example 73 was prepared as described in Step 71-7. 12 mg was obtained as an off-white solid. MS m/z: [M+H]+= 433.20. ¹H NMR (400 MHz, DMSO-d6) δ 10.73 (s, 1H), 8.45 (m, 1H), 8.14 (t, J=8.0 Hz, 1H), 8.01-7.94 (m, 2H), 7.87 (s, 1H), 7.67 (s, 1H), 7.22 (s, 1H), 5.85 (m, 1H), 4.01 (s, 3H), 3.90 (s, 3H), 2.46 (s, 3H), 1.63 (d, J=6.6 Hz, 6H).

Example 74

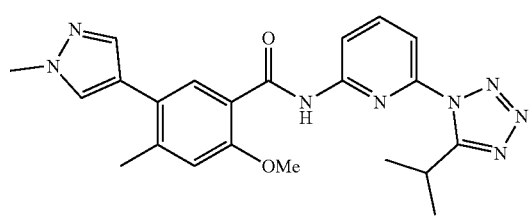 [SMILES: COc1cc(C)c(-c2cnn(C)c2)cc1C(=O)Nc1cccc(-n2nnnc2C(C)C)n1]

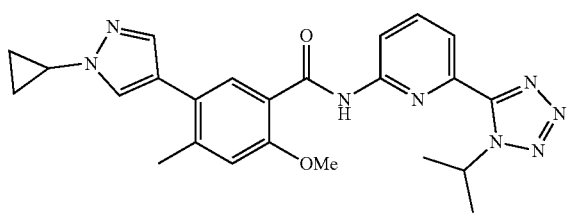 [SMILES: COc1cc(C)c(-c2cnn(C3CC3)c2)cc1C(=O)Nc1cccc(-c2nnnn2C(C)C)n1]

Example 74

Example 74 was prepared as described in Step 71-7. 12 mg was obtained as an off-white solid. MS m/z 432.20, 433.20 [M+H]+; ¹H NMR (400 MHz, DMSO-d6) δ 10.69 (s, 1H), 8.43 (d, J=8.3 Hz, 1H), 8.21 (t, J=8.1 Hz, 1H), 7.97 (s, 1H), 7.86 (s, 1H), 7.70 (d, J=7.8 Hz, 1H), 7.66 (s, 1H), 7.20 (s, 1H), 3.99 (s, 3H), 3.89-3.80 (m, 4H), 2.45 (s, 3H), 1.40 (d, J=6.9 Hz, 6H).

Example 75

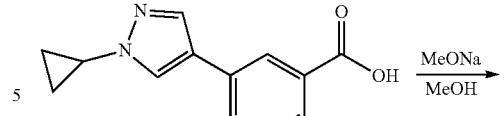

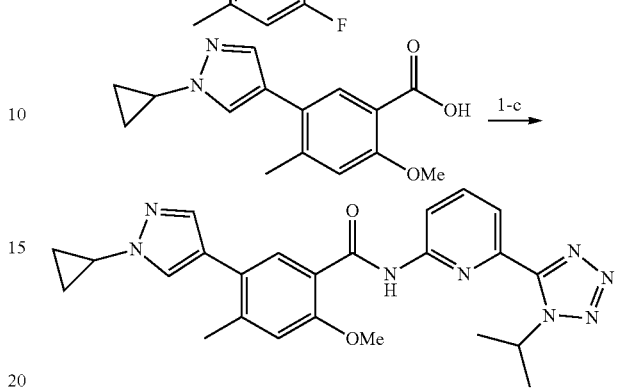

Example 75

Step 75-1

A solution of 5-(1-cyclopropyl-1H-pyrazol-4-yl)-2-fluoro-4-methylbenzoic acid (300 mg, 1.2 mmol) and sodium methylate (15 mL, 30%) was stirred at 80° C. overnight. The solution was quenched with water, acidified to pH 4~5 with 1M HCl (aq.), and extracted with EtOAc (10 mL×3). The combined organic layers were dried over anhydrous Na₂SO₄ and concentrated under reduced pressure. The residue was purified by silica gel column chromatography with DCM/MeOH (30:1) to give 5-(1-cyclopropyl-1H-pyrazol-4-yl)-2-methoxy-4-methylbenzoic acid (310 mg, 98.77%) as a light pink solid.

Step 75-2

Example 75 was prepared as described in Step 71-7. 15.3 mg was obtained as an off-white solid. MS m/z: [M+H]+= 459.40. ¹H NMR (400 MHz, Chloroform-d) δ 10.55 (s, 1H), 8.61 (dd, J=8.3, 1.1 Hz, 1H), 8.25 (s, 1H), 8.04 (dd, J=7.6, 1.1 Hz, 1H), 7.97 (t, J=7.9 Hz, 1H), 7.65 (d, J=12.6 Hz, 2H), 6.96 (s, 1H), 5.81 (m, 1H), 4.11 (s, 3H), 3.68 (m, 1H), 2.51 (s, 3H), 1.77 (d, J=6.7 Hz, 6H), 1.24-1.21 (m, 2H), 1.18-1.05 (m, 2H).

Example 76

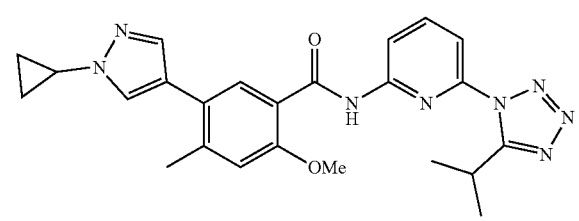 [SMILES: COc1cc(C)c(-c2cnn(C3CC3)c2)cc1C(=O)Nc1cccc(-n2nnnc2C(C)C)n1]

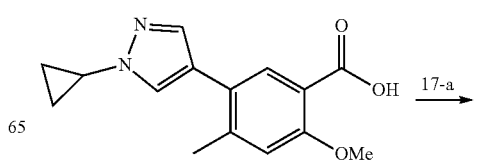

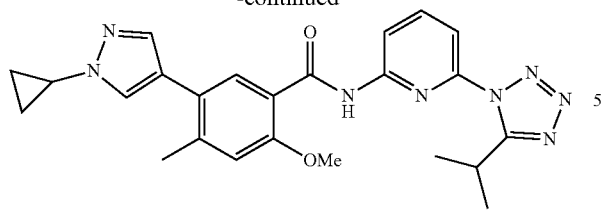
Example 76
Example 76 was prepared as described in Step 71-7. 12.6 mg was obtained as an off-white solid. MS m/z: [M+H]$^+$= 459.25. $^1$H NMR (400 MHz, Chloroform-d) δ 10.55 (s, 1H), 8.58 (dd, J=8.3, 0.7 Hz, 1H), 8.24 (s, 1H), 8.02 (t, J=8.1 Hz, 1H), 7.69-7.60 (m, 3H), 6.96 (s, 1H), 4.10 (s, 3H), 3.92 (m, 1H), 3.68 (m, 1H), 2.51 (s, 3H), 1.57 (d, J=6.9 Hz, 6H), 1.25-1.13 (m, 2H), 1.17-1.04 (m, 2H).
Example 77
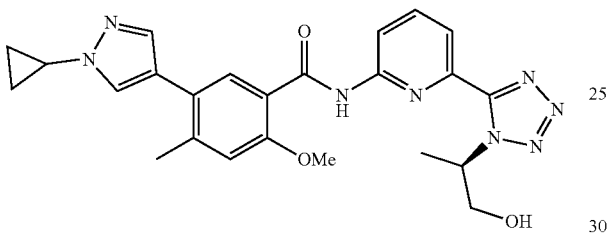
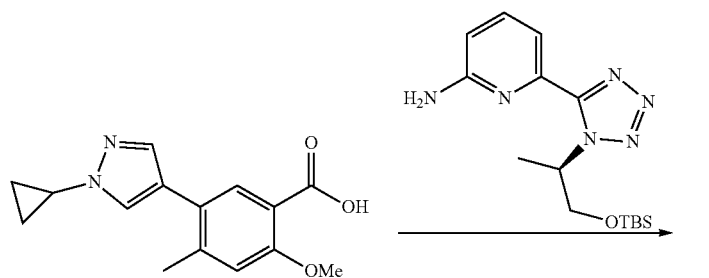
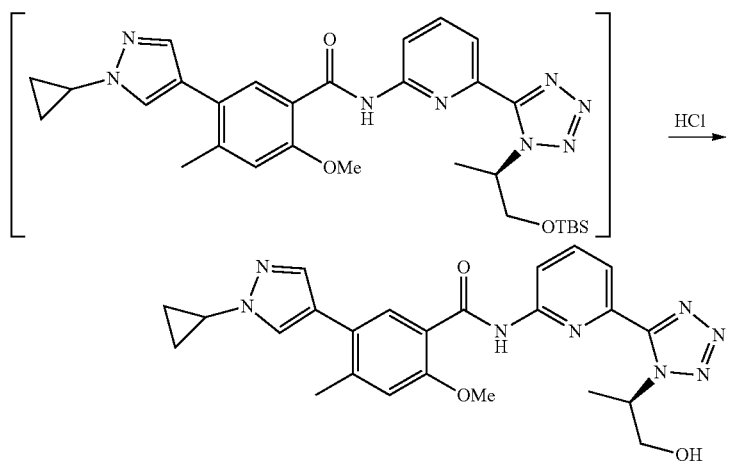
Example 77

To a stirred solution of 5-(1-cyclopropyl-1H-pyrazol-4-yl)-2-methoxy-4-methylbenzoic acid (50 mg, 0.2 mmol) in DCM (1 mL) was added (1-chloro-2-methylprop-1-en-1-yl)dimethylamine (30 mg, 0.2 mmol) dropwise at room temperature under nitrogen atmosphere. After 2 hours a solution of 6-[1-[(2R)-1-[(tert-butyldimethylsilyl)oxy]propan-2-yl]-1H-1,2,3,4-tetrazol-5-yl]pyridin-2-amine (93 mg, 0.3 mmol) and pyridine (44 mg, 0.6 mmol) in DCM (1 mL) was added. The reaction was stirred for 2 hours and conc HCl (0.4 mL) was added dropwise at room temperature. After 1 hour, the resulting mixture was concentrated under reduced pressure. The residue was purified by reverse flash chromatography with the following conditions (column, C18 silica gel; mobile phase, ACN in water, 0 to 100% gradient in 25 min; detector, UV 254 nm) to give 5-(1-cyclopropyl-1H-pyrazol-4-yl)-N-(6-[1-[(2R)-1-hydroxypropan-2-yl]-1H-1,2,3,4-tetrazol-5-yl]pyridin-2-yl)-2-methoxy-4-methylbenzamide (13 mg, 14.8%) as an off-white solid. MS m/z: [M+H]$^+$=475.25. $^1$H NMR (400 MHz, Chloroform-d) δ 10.65 (s, 1H), 8.57 (dd, J=7.1, 2.2 Hz, 1H), 8.23 (s, 1H), 8.04-7.94 (m, 2H), 7.66-7.59 (m, 2H), 6.95 (s, 1H), 5.68 (m, 1H), 4.16 (d, J=6.4 Hz, 2H), 4.14 (s, 3H), 3.93 (s, 1H), 3.67 (m, 1H), 2.50 (s, 3H), 1.74 (d, J=6.9 Hz, 3H), 1.22-1.19 (m, 2H), 1.17-1.02 (m, 2H).

Example 78

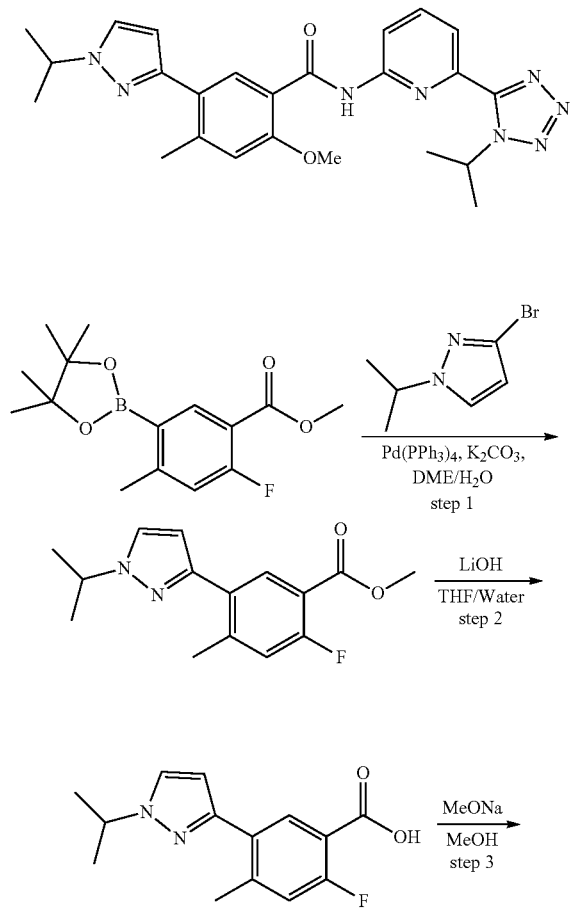

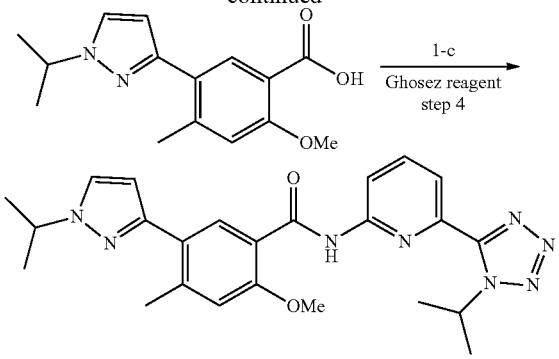

Example 78

Step 78-1

A mixture of methyl 2-fluoro-4-methyl-5-(4,4,5,5-tetramethyl-1,3,2-dioxaborolan-2-yl)benzoate (400 mg, 1.4 mmol), 3-bromo-1-(propan-2-yl)-1H-pyrazole (312 mg, 1.8 mmol), K$_2$CO$_3$ (560 mg, 4.1 mmol), and Pd(PPh$_3$)$_4$ (80 mg, 0.1 mmol) in DME/H$_2$O (/5/1 mL) was stirred at 100° C. under nitrogen atmosphere for 1 hour. The resulting mixture was cooled to room temperature, diluted with water (20 mL), and extracted with EtOAc (20 mL×3). The combined organic layers were dried over anhydrous Na$_2$SO$_4$ and concentrated under reduced pressure. The residue was purified by silica gel column chromatography with PE/EtOAc (20:1) to give methyl 2-fluoro-4-methyl-5-[1-(propan-2-yl)-1H-pyrazol-3-yl] benzoate (173 mg, 46%) as a yellow oil.

Step 78-2

To a stirred solution of methyl 2-fluoro-4-methyl-5-[1-(propan-2-yl)-1H-pyrazol-3-yl]benzoate (173 mg, 0.6 mmol) in THF/H$_2$O (3/1 mL) was added LiOH (200 mg, 8.4 mmol) and the resulting mixture was stirred at room temperature overnight. Then the mixture was acidified to pH 4~5 with 1M HCl (aq), and extracted with EtOAc (10 mL×3). The combined organic layers were dried over anhydrous Na$_2$SO$_4$ and concentrated under reduced pressure to give 2-fluoro-5-(1-isopropylpyrazol-3-yl)-4-methylbenzoic acid (160 mg) as a grey solid.

Step 78-3

A mixture of 2-fluoro-5-(1-isopropylpyrazol-3-yl)-4-methylbenzoic acid (160 mg, 0.6 mmol) and 30% sodium methoxide in methanol (12 mL) was stirred at 80° C. overnight. The mixture was acidified to pH 4~5 with 1M HCl (aq) and extracted with EtOAc (10 mL×3). The combined organic layers were dried over anhydrous Na$_2$SO$_4$ and concentrated under reduced pressure. The residue was purified by silica gel column chromatography with DCM/MeOH (20:1) to give 5-(1-isopropylpyrazol-3-yl)-2-methoxy-4-methylbenzoic acid (162 mg, 96.8%) as a grey solid.

Step 78-4

Example 78 was prepared as described in Step 71-7. MS m/z: [M+H]+=461.35. $^1$H NMR (400 MHz, Chloroform-d) δ 10.54 (s, 1H), 8.62 (d, J=8.3 Hz, 1H), 8.49 (s, 1H), 8.03 (d, J=7.4 Hz, 1H), 7.96 (t, J=7.9 Hz, 1H), 7.49 (d, J=2.3 Hz, 1H), 6.96 (s, 1H), 6.45 (d, J=2.2 Hz, 1H), 5.83 (m, 1H), 4.57 (m, 1H), 4.11 (s, 3H), 2.62 (s, 3H), 1.78 (d, J=6.7 Hz, 6H), 1.59 (d, J=6.7 Hz, 6H).

Example 79
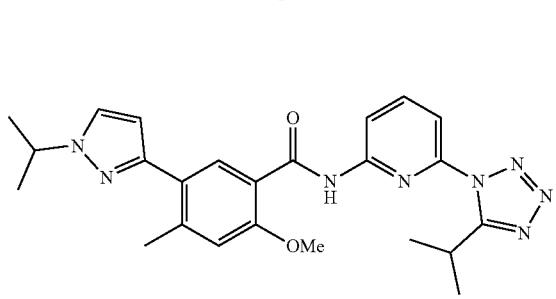 [SMILES: COc1cc(C)c(-c2ccn(C(C)C)n2)cc1C(=O)Nc1cccc(-n2nnnc2C(C)C)n1]
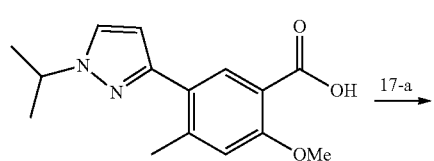
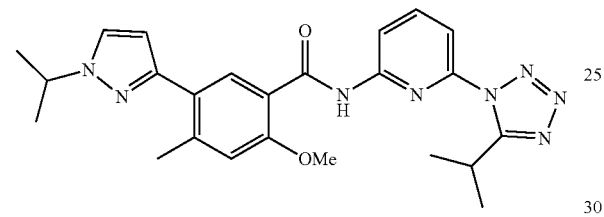
Example 79
Example 79 was prepared as described in Step 71-7. MS m/z: [M+H]⁺=461.25. ¹H NMR (400 MHz, Chloroform-d) δ 10.53 (s, 1H), 8.60 (d, J=8.3 Hz, 1H), 8.48 (s, 1H), 8.01 (t, J=8.1 Hz, 1H), 7.65 (d, J=7.7 Hz, 1H), 7.49 (d, J=2.2 Hz, 1H), 6.95 (s, 1H), 6.44 (d, J=2.2 Hz, 1H), 4.57 (m, 1H), 4.10 (s, 3H), 3.93 (m, 1H), 2.62 (s, 3H), 1.59-1.56 (m, 12H).
Example 80
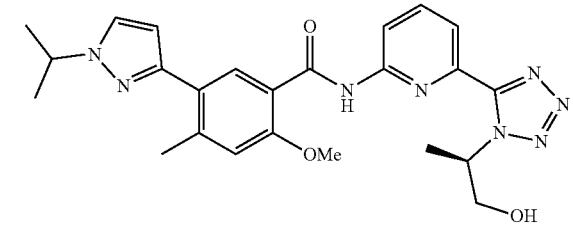 [SMILES: COc1cc(C)c(-c2ccn(C(C)C)n2)cc1C(=O)Nc1cccc(-c2nnnn2[C@H](C)CO)n1]
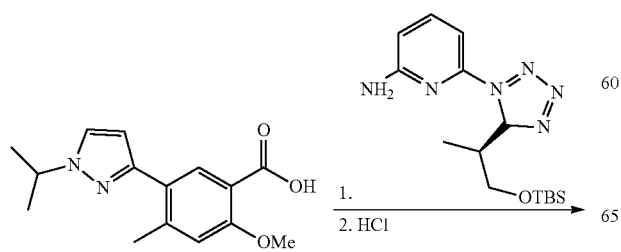
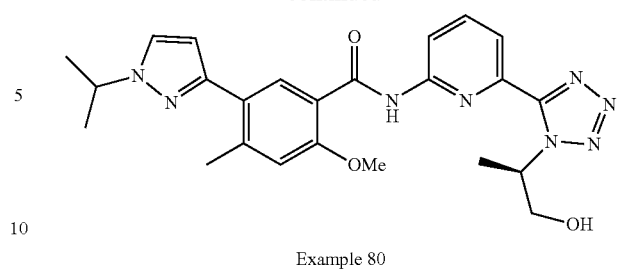
Example 80
Example 80 was prepared as a white solid employing a similar procedure as shown in Example 77. MS m/z: [M+H]⁺=477.25. ¹H NMR (400 MHz, Chloroform-d) δ 10.64 (s, 1H), 8.59 (d, J=7.8 Hz, 1H), 8.47 (s, 1H), 8.02-7.93 (m, 2H), 7.49 (d, J=2.2 Hz, 1H), 6.94 (s, 1H), 6.44 (d, J=2.2 Hz, 1H), 5.70 (m, 1H), 4.58 (m, 1H), 4.17-4.14 (m, 5H), 2.61 (s, 3H), 1.75 (d, J=6.8 Hz, 3H), 1.59 (d, J=6.6 Hz, 6H).
Example 81
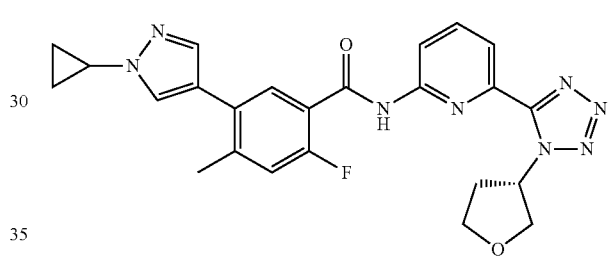
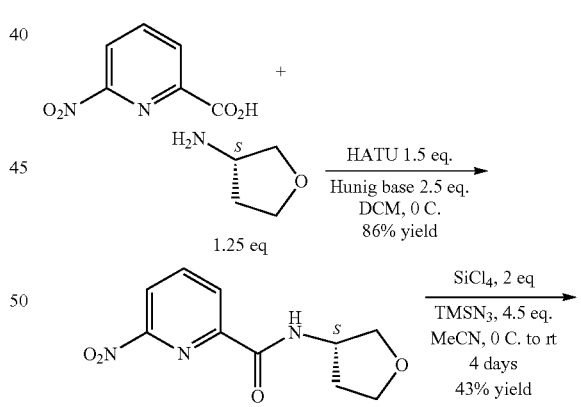
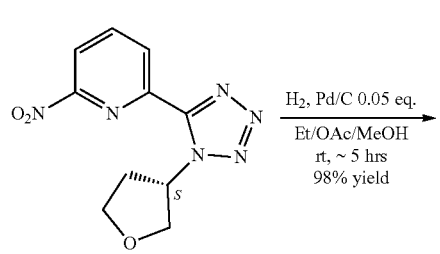

Example 82
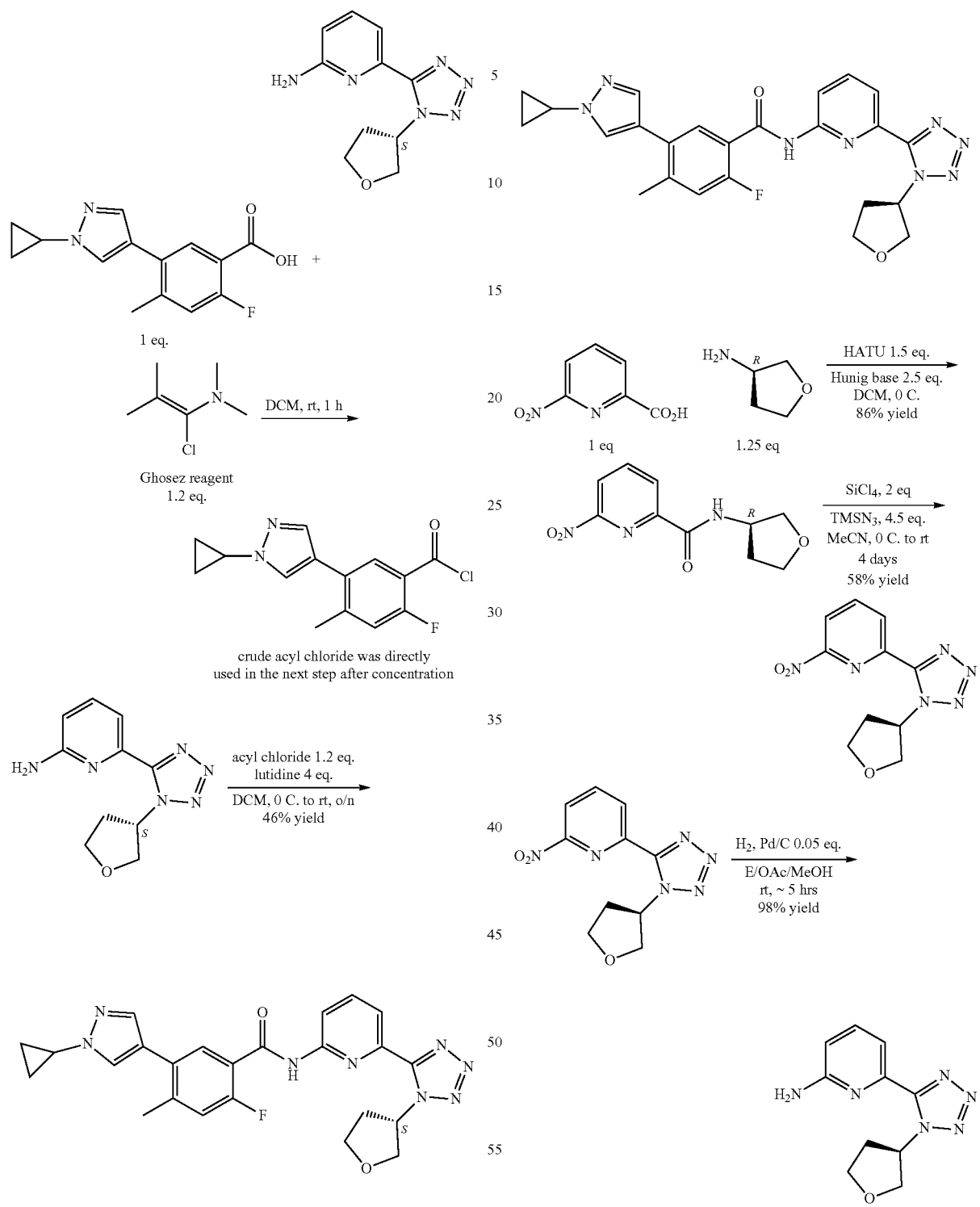
Example 81 was prepared following the chemistry shown in the above synthetic scheme. [M+H]+ 475.2. ¹H NMR (400 MHz, Chloroform-d) δ 9.19 (d, J=16.9 Hz, 1H), 8.56 (d, J=8.1 Hz, 1H), 8.15 (d, J=3.7 Hz, 1H), 8.13 (d, J=5.0 Hz, 1H), 8.02 (dd, J=8.0, 8.0 Hz, 1H), 7.65 (s, 1H), 7.64 (s, 1H), 7.14 (d, J=13.3 Hz, 1H), 6.09 (ddt, J=9.6, 6.6, 3.3 Hz, 1H), 4.40-4.34 (m, 2H), 4.22 (dd, J=9.9, 3.6 Hz, 1H), 4.20-4.13 (m, 1H), 3.72-3.66 (m, 1H), 2.83-2.76 (m, 1H), 2.68-2.54 (m, 1H), 2.50 (s, 3H), 1.25-1.18 (m, 2H), 1.16-1.05 (m, 2H).
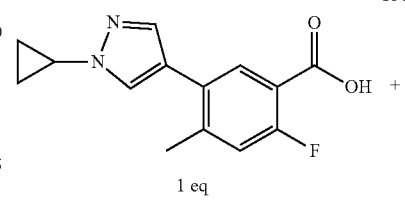

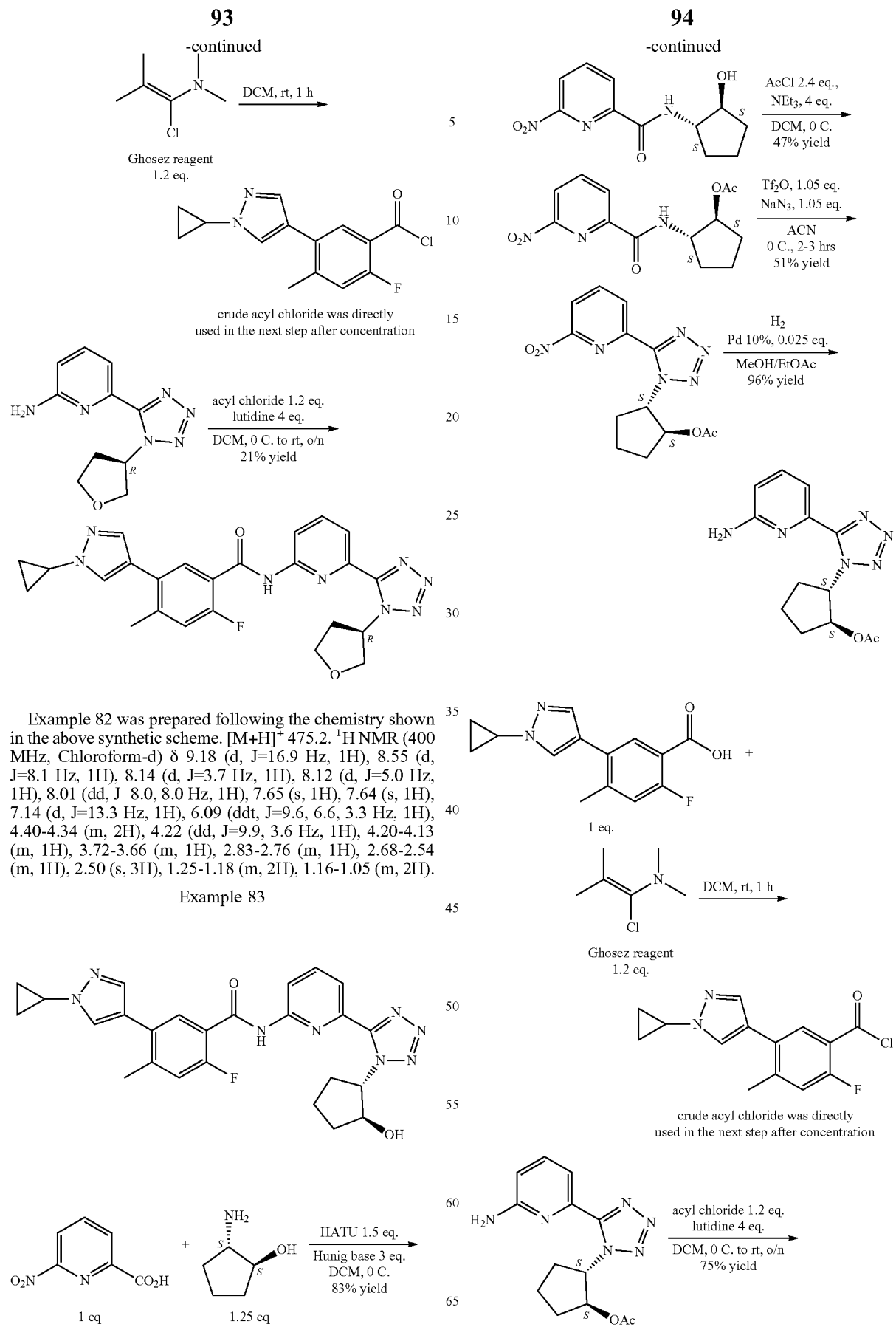
Example 82 was prepared following the chemistry shown in the above synthetic scheme. [M+H]+ 475.2. ¹H NMR (400 MHz, Chloroform-d) δ 9.18 (d, J=16.9 Hz, 1H), 8.55 (d, J=8.1 Hz, 1H), 8.14 (d, J=3.7 Hz, 1H), 8.12 (d, J=5.0 Hz, 1H), 8.01 (dd, J=8.0, 8.0 Hz, 1H), 7.65 (s, 1H), 7.64 (s, 1H), 7.14 (d, J=13.3 Hz, 1H), 6.09 (ddt, J=9.6, 6.6, 3.3 Hz, 1H), 4.40-4.34 (m, 2H), 4.22 (dd, J=9.9, 3.6 Hz, 1H), 4.20-4.13 (m, 1H), 3.72-3.66 (m, 1H), 2.83-2.76 (m, 1H), 2.68-2.54 (m, 1H), 2.50 (s, 3H), 1.25-1.18 (m, 2H), 1.16-1.05 (m, 2H).
Example 83

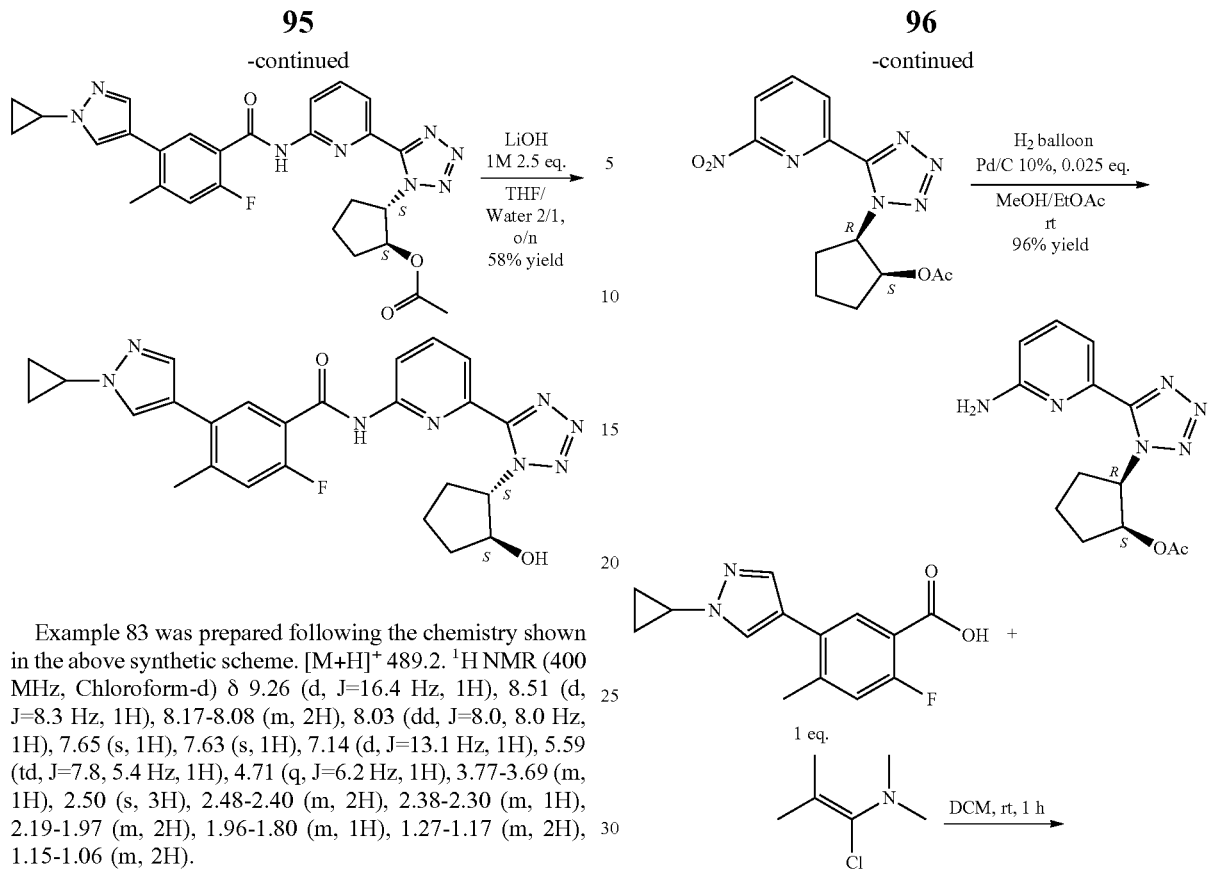
Example 83 was prepared following the chemistry shown in the above synthetic scheme. [M+H]+ 489.2. 1H NMR (400 MHz, Chloroform-d) δ 9.26 (d, J=16.4 Hz, 1H), 8.51 (d, J=8.3 Hz, 1H), 8.17-8.08 (m, 2H), 8.03 (dd, J=8.0, 8.0 Hz, 1H), 7.65 (s, 1H), 7.63 (s, 1H), 7.14 (d, J=13.1 Hz, 1H), 5.59 (td, J=7.8, 5.4 Hz, 1H), 4.71 (q, J=6.2 Hz, 1H), 3.77-3.69 (m, 1H), 2.50 (s, 3H), 2.48-2.40 (m, 2H), 2.38-2.30 (m, 1H), 2.19-1.97 (m, 2H), 1.96-1.80 (m, 1H), 1.27-1.17 (m, 2H), 1.15-1.06 (m, 2H).
Example 84
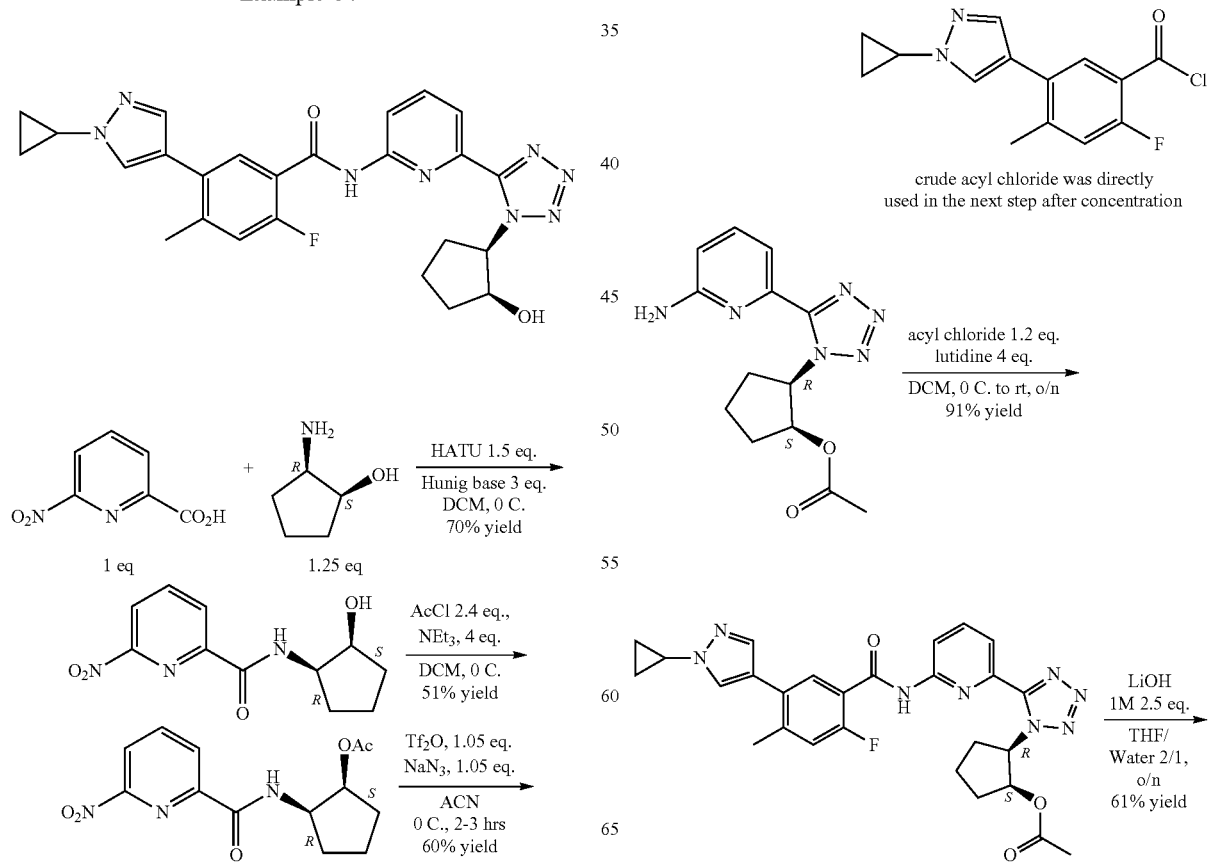

-continued

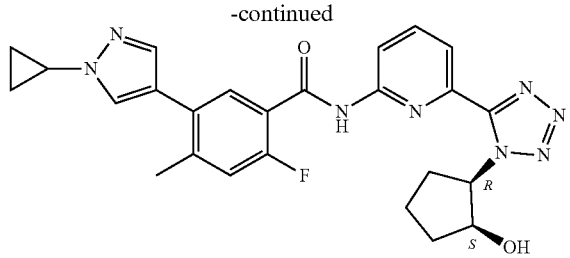

Example 84 was prepared following the chemistry shown in the above synthetic scheme. [M+H]⁺ 489.2. ¹H NMR (400 MHz, Chloroform-d) δ 9.17 (d, J=17.4 Hz, 1H), 8.52 (d, J=8.3 Hz, 1H), 8.14 (d, J=8.3 Hz, 1H), 8.12-8.08 (m, 1H), 8.03 (dd, J=8.0, 8.0 Hz, 1H), 7.65 (d, J=0.8 Hz, 1H), 7.63 (s, 1H), 7.14 (d, J=13.2 Hz, 1H), 5.64-5.49 (m, 1H), 4.64 (q, J=5.9 Hz, 1H), 3.73-3.69 (m, 1H), 2.67-2.57 (m, 1H), 2.50 (s, 2H), 2.40-2.34 (m, 1H), 2.32-2.26 (m, 1H), 2.22-2.11 (m, 1H), 2.10-1.96 (m, 1H), 1.90-1.78 (m, 1H), 1.26-1.18 (m, 2H), 1.14-1.06 (m, 2H).

Assays

The ability (IC$_{50}$) of compounds to inhibit ASK1 kinase activity was determined by HTRF® KinEASE™ Assay System. ASK1 was purchased from Thermofisher (Catalogue #PV4011), ATP was purchased from Sigma (Catalogue #A7699), HTRF® KinEASE™ Assay System was obtained from Cisbio (Bedford, Mass.). ½ Area plate was purchased from Perkin Elmer (Catalogue ##6005560). HTRF® KinEASE™-STK is a generic method for measuring serine/threonine kinase activities using a time-resolved fluorescence resonance energy transfer (TR-FRET) immunoassay. The IC$_{50}$ value for each compound was determined in the presence of compound (various concentration from 0 to 10 μM) and a fixed amount of ATP and peptide substrates. The test compound, 1 uM STK3 peptide substrate, and 5 nM of ASK1 kinase are incubated with kinase reaction buffer containing 50 mM HEPES pH 7.5, 0.01% BRIJ-35, 10 mM MgCl2, and 1 mM EGTA for 30 minutes. 100 uM ATP is added to start kinase reaction and incubated for 3 hours. The STK3-antibody labeled with Eu$^{3+}$-Cryptate and 125 nM streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. IC$_{50}$ was determined by XLfit 5.3. By using above method, the inhibition of ASK1 was tested for the compound of formula (I). IC$_{50}$ ranges are as follows: A<1 nM; 1 nM<B<10 nM; 10 nM<C<100 nM; 100 nM<D<1 μM; E>1 μM.

TABLE 1

| Example | IC$_{50}$ | Example | IC$_{50}$ | Example | IC$_{50}$ |
|---|---|---|---|---|---|
| 1 | C | 2 | C | 3 | C |
| 4 | C | 5 | C | 6 | B |
| 7 | B | 8 | C | 9 | B |
| 10 | B | 11 | C | 12 | B |
| 13 | B | 14 | C | 15 | C |
| 16 | B | 17 | C | 18 | B |
| 19 | B | 20 | B | 21 | C |
| 22 | B | 23 | C | 24 | E |
| 25 | B | 26 | B | 27 | B |
| 28 | B | 29 | B | 30 | C |

TABLE 1-continued

| Example | IC$_{50}$ | Example | IC$_{50}$ | Example | IC$_{50}$ |
|---|---|---|---|---|---|
| 31 | E | 32 | B | 33 | C |
| 34 | E | 35 | B | 36 | C |
| 37 | B | 38 | C | 39 | B |
| 40 | C | 41 | B | 42 | B |
| 43 | B | 44 | C | 45 | B |
| 46 | B | 47 | B | 48 | B |
| 49 | B | 50 | B | 51 | B |
| 52 | B | 53 | B | 54 | B |
| 55 | C | 56 | D | 57 | B |
| 58 | C | 59 | E | 60 | C |
| 61 | C | 62 | E | 63 | C |
| 64 | D | 65 | B | 66 | C |
| 67 | C | 68 | D | 69 | C |
| 70 | B | 71 | C | 72-A/B | C |
| 73 | B | 74 | B | 75 | A |
| 76 | A | 77 | A | 78 | B |
| 79 | C | 80 | A | 81 | B |
| 82 | B | 83 | B | 84 | B |

While this invention has been particularly shown and described with references to preferred embodiments thereof, it will be understood by those skilled in the art that various changes in form and details may be made therein without departing from the scope of the invention encompassed by the appended claims.

We claim:

1. A compound represented by Formula I or a pharmaceutically acceptable salt or ester thereof:

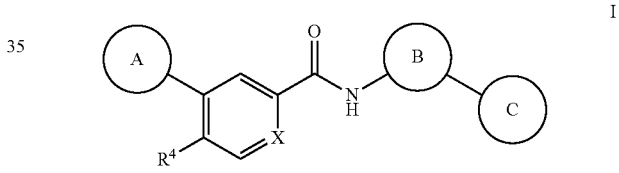

wherein

is selected from the groups below

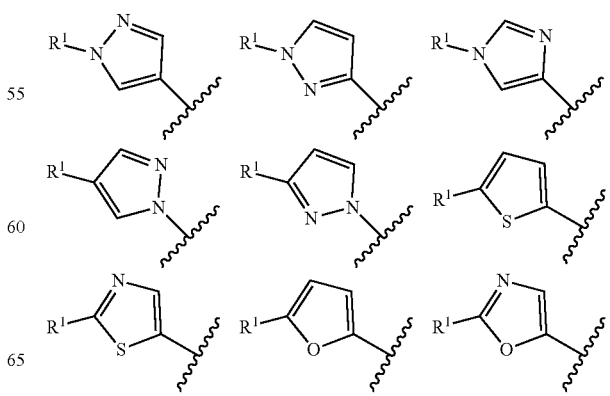

99

-continued

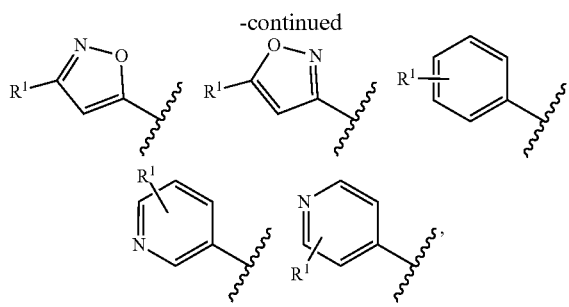

B is

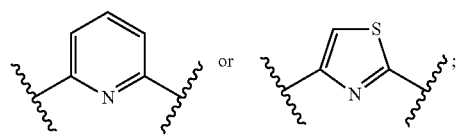 [SMILES: *c1cccc(*)n1 ; *c1csc(*)n1]

C is

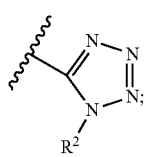

$R^1$ is selected from the group consisting of:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted aryl;
7) Optionally substituted arylalkyl;
8) Optionally substituted 3- to 8-membered heterocycloalkyl;
9) Optionally substituted heteroaryl; and
10) Optionally substituted heteroarylalkyl;

$R^2$ is

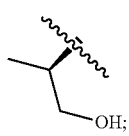

100

X is N or C—$R^3$;
$R^3$ is selected from the group consisting of:
1) Hydrogen;
2) Halogen;
3) Optionally substituted —$C_1$-$C_8$ alkyl; and
4) Optionally substituted —$C_1$-$C_8$ alkoxyl;

$R^4$ is selected from the group consisting of:
1) Hydrogen;
2) Halogen;
3) Optionally substituted —$C_1$-$C_8$ alkyl;
4) Optionally substituted —$C_2$-$C_8$ alkenyl;
5) Optionally substituted —$C_2$-$C_8$ alkynyl;
6) Optionally substituted —$C_3$-$C_8$ cycloalkyl;
7) Optionally substituted aryl;
8) Optionally substituted arylalkyl;
9) Optionally substituted 3- to 8-membered heterocycloalkyl;
10) Optionally substituted heteroaryl;
11) Optionally substituted heteroarylalkyl; and
12) —N($R^5$)($R^6$);

wherein $R^5$ and $R^6$ are independently selected from the group consisting of hydrogen, —$C_1$-$C_8$ alkyl, cycloalkyl, heterocycloalkyl, aryl, and heteroaryl, wherein the —$C_1$-$C_8$ alkyl, cycloalkyl, heterocycloalkyl, aryl, or heteroaryl is optionally substituted with 1-3 substituents independently selected from halo, alkyl, alkylamino, dialkylamino, alkylC(O)NH—, arylC(O)NH—, heteroarylC(O)NH—, —CN, alkoxy, —$CF_3$, aryl, and heteroaryl; alternatively, $R^5$ and $R^6$ are taken together with the nitrogen atom to which they are attached to form an optionally substituted heterocyclic.

2. The compound of claim 1, represented by one of Formulas (II-a), (II-c), (II-e), and (II-g), or a pharmaceutically acceptable salt thereof:

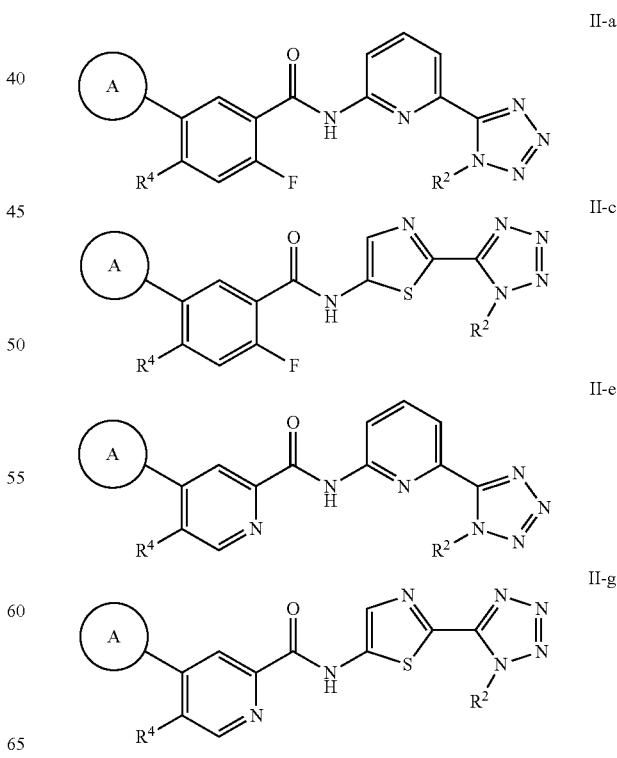

wherein
,
R² and R⁴ are as defined in claim 1.
3. The compound of claim 1, represented by one of Formulas (III-a) ~(III-n), or a pharmaceutically acceptable salt thereof:
III-a
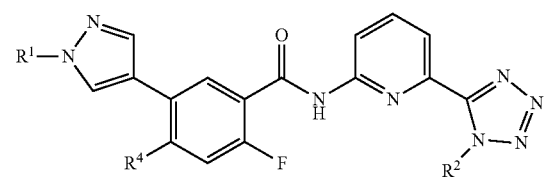
III-b
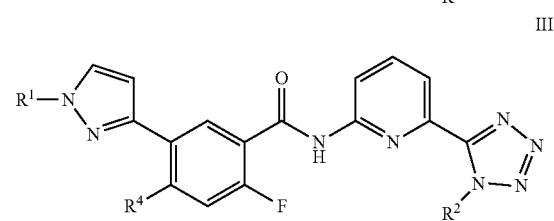
III-c
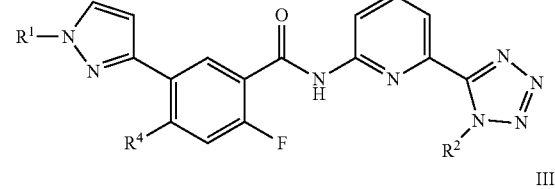
III-d
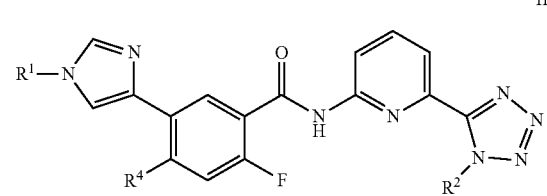
III-e
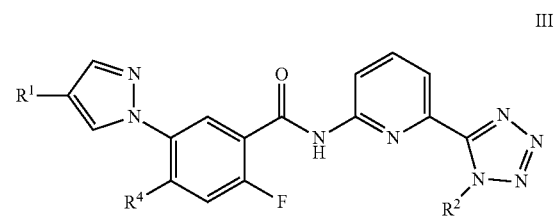
III-f
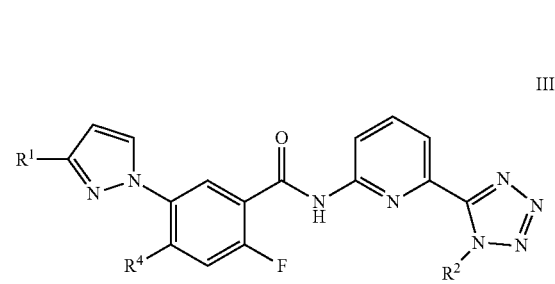
III-g
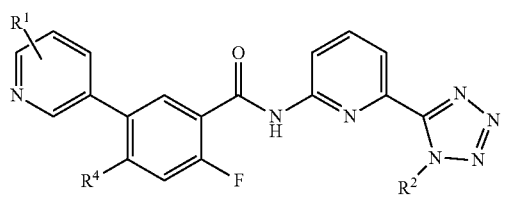
III-h
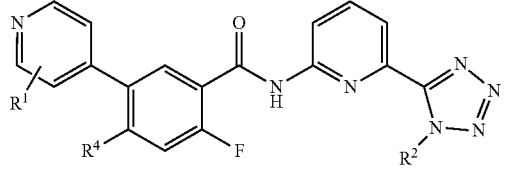
III-i
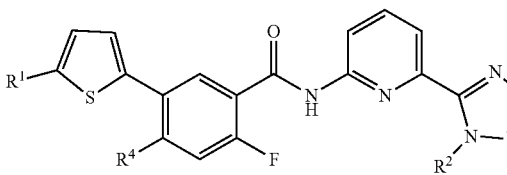
III-j
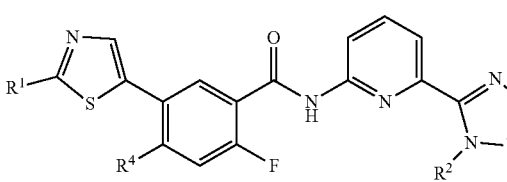
III-k
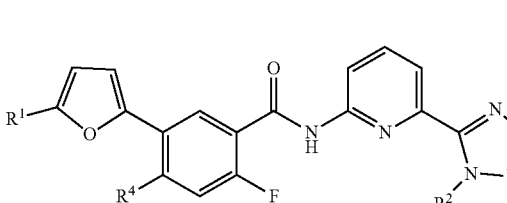
III-l
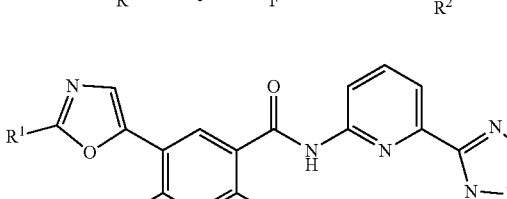
III-m
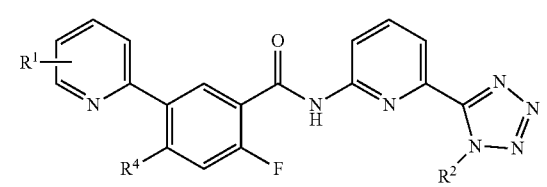
III-n
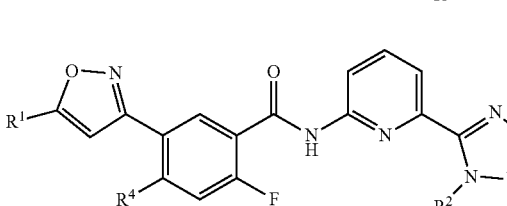
wherein R¹, R² and R⁴ are as defined in claim 1.

4. The compound of claim 1, represented by one of Formulas (IV-a) ~(IV-n), or a pharmaceutically acceptable salt thereof:

IV-a
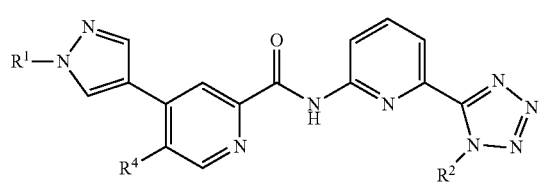

IV-b
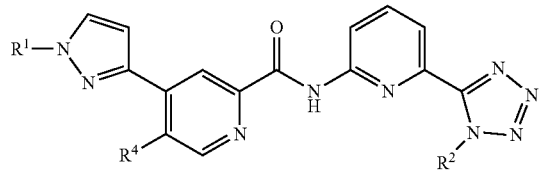

IV-c
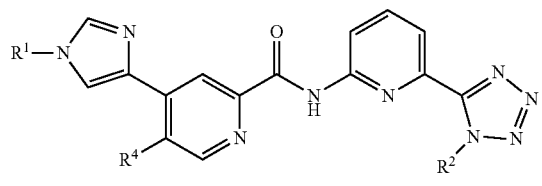

IV-d
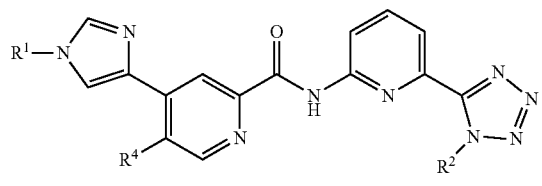

IV-e
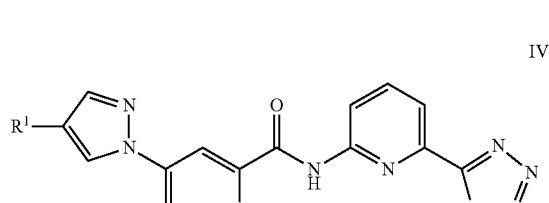

IV-f
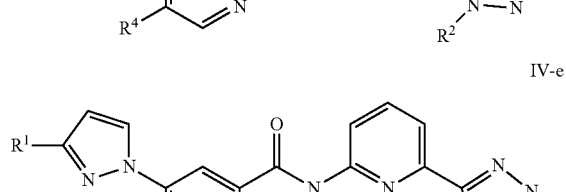

IV-g
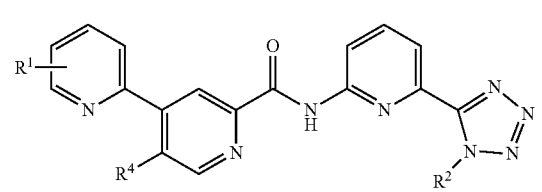

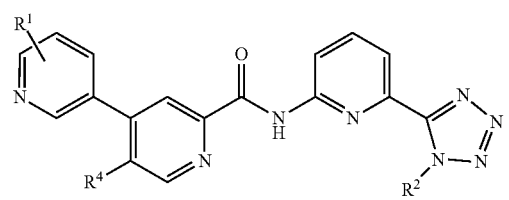

-continued

IV-h
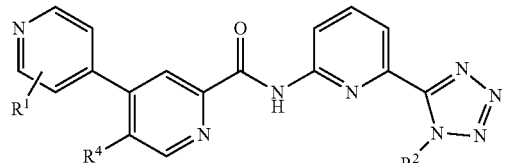

IV-i
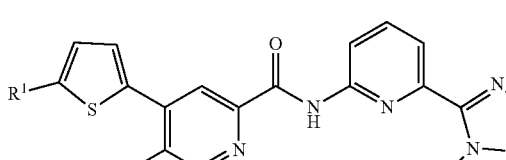

IV-j
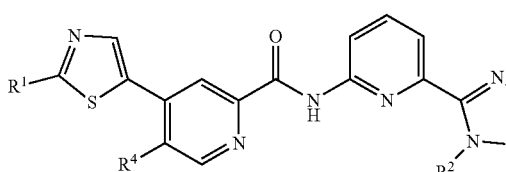

IV-k
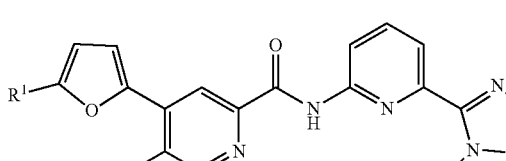

IV-l
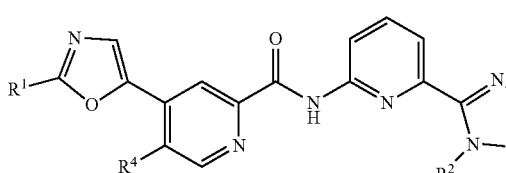

IV-m

IV-n
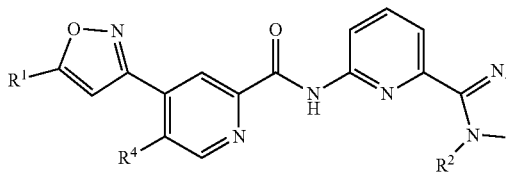

wherein $R^1$, $R^2$ and $R^4$ are as defined in claim 1.

5. A pharmaceutical composition comprising a compound of claim 1 and a pharmaceutically acceptable carrier or excipient.

6. The compound of claim 1, selected from the compounds set forth below or a pharmaceutically acceptable salt thereof:

| Compound | Structure | Compound | Structure |
|---|---|---|---|
| 13 | 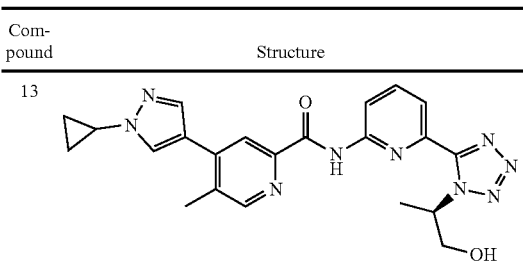 | 16 | 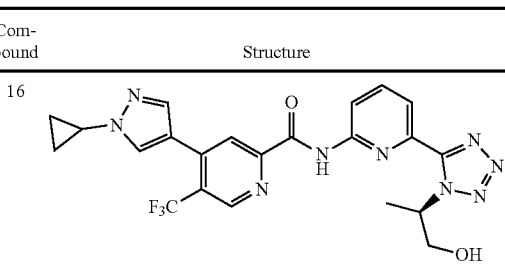 |
| 22 | 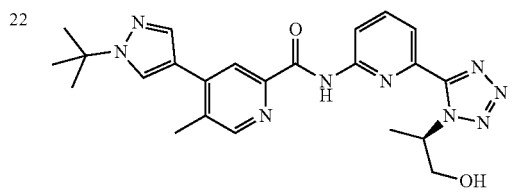 | 25 | 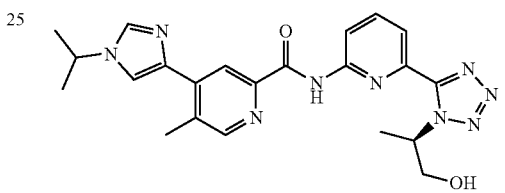 |
| 28 | 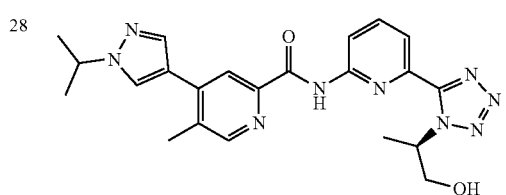 | 29 | 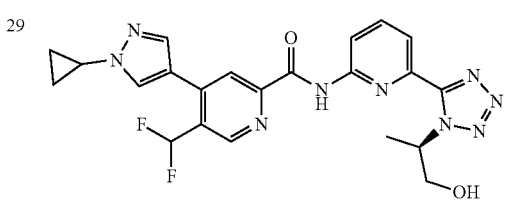 |
| 32 | 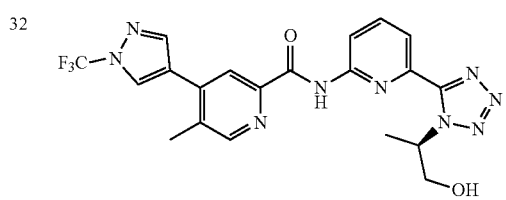 | 35 | 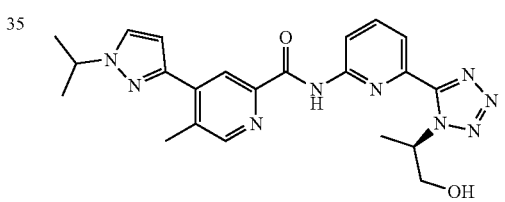 |
| 41 | 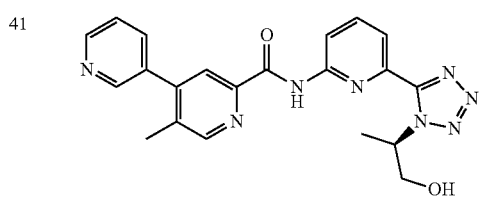 | 43 | 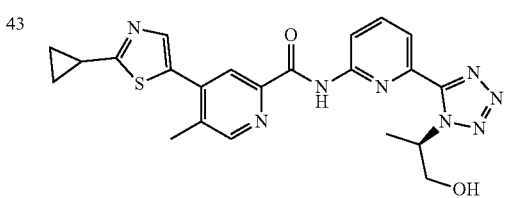 |
| 45 | 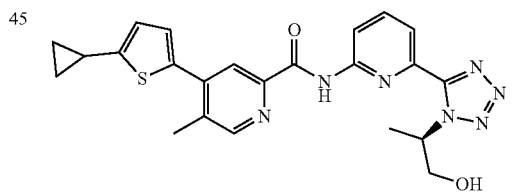 | 47 | 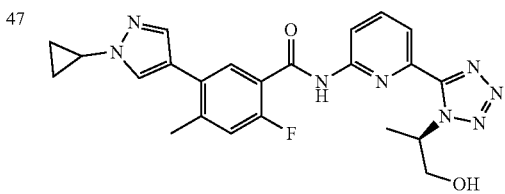 |
| 50 | 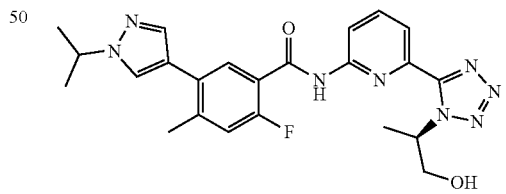 | 54 | 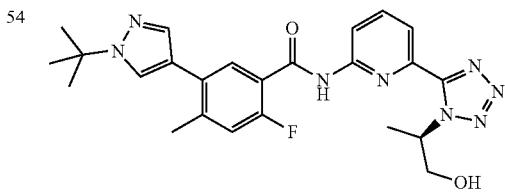 |
| 57 | 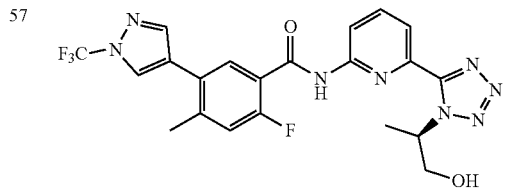 | 60 | 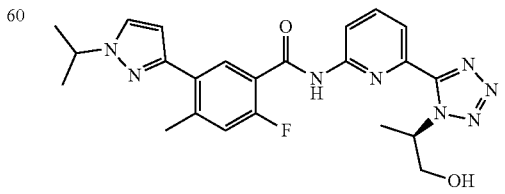 |

-continued
| Compound | Structure | Compound | Structure |
|---|---|---|---|
| 63 | 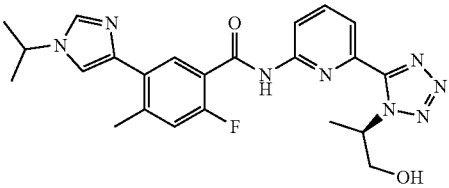 [SMILES: Cc1cc(F)c(C(=O)Nc2cccc(-c3nnnn3[C@H](C)CO)n2)cc1-c1cn(C(C)C)cn1] | 70 | 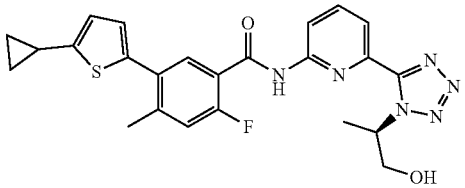 [SMILES: Cc1cc(F)c(C(=O)Nc2cccc(-c3nnnn3[C@H](C)CO)n2)cc1-c1ccc(C2CC2)s1] |
| 77 | 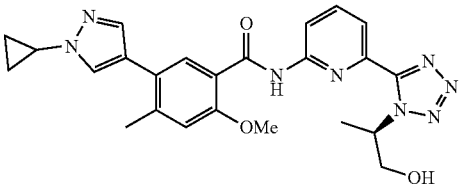 [SMILES: COc1cc(C)c(-c2cnn(C3CC3)c2)cc1C(=O)Nc1cccc(-c2nnnn2[C@H](C)CO)n1] | 80 | 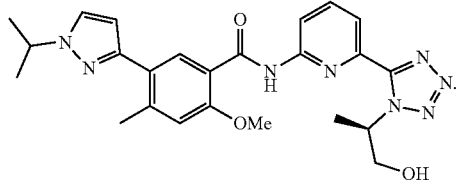 [SMILES: COc1cc(C)c(-c2ccn(C(C)C)n2)cc1C(=O)Nc1cccc(-c2nnnn2[C@H](C)CO)n1] |
* * * * *

UNITED STATES PATENT AND TRADEMARK OFFICE
CERTIFICATE OF CORRECTION

PATENT NO.      : 11,008,304 B2
APPLICATION NO. : 16/400529
DATED           : May 18, 2021
INVENTOR(S)     : Guoqiang Wang et al.

It is certified that error appears in the above-identified patent and that said Letters Patent is hereby corrected as shown below:

In the Claims

<u>At Column 99</u>

In Claim 1, Line 5, delete " 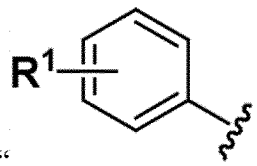 " and insert -- 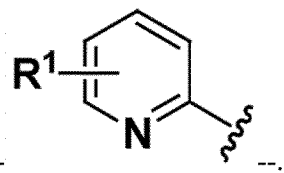 --.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*